US009511952B1

(12) United States Patent
Schneider et al.

(10) Patent No.: US 9,511,952 B1
(45) Date of Patent: Dec. 6, 2016

(54) METHODS FOR TRANSFERRING DISCRETE ARTICLES

(71) Applicant: The Procter & Gamble Company, Cincinnati, OH (US)

(72) Inventors: Uwe Schneider, Cincinnati, OH (US); Clifford Theodore Papsdorf, Loveland, OH (US); Daniel Patrick Findley, Finneytown, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/747,296

(22) Filed: Jun. 23, 2015

(51) Int. Cl.
*B65G 17/32* (2006.01)
*B65G 47/244* (2006.01)
*B65G 29/02* (2006.01)
*A61F 13/15* (2006.01)

(52) U.S. Cl.
CPC ....... *B65G 47/244* (2013.01); *A61F 13/15764* (2013.01); *B65G 29/02* (2013.01); *A61F 2013/15821* (2013.01)

(58) Field of Classification Search
CPC ....... B65G 29/00; B65G 29/02; B65G 47/244; B65G 47/846; B65G 47/847; B65G 47/848
USPC ... 198/377.01–377.1, 469.1–487.1; 271/314, 264, 275, 276, 3.21, 3.22
See application file for complete search history.

(56) References Cited

U.S. PATENT DOCUMENTS

| 231,145 | A | | 8/1880 | Brady |
| 916,702 | A | | 3/1909 | Hartt |
| 1,746,544 | A | | 2/1930 | Malm |
| 2,660,088 | A | | 11/1953 | Vinto |
| 3,029,655 | A | | 4/1962 | Morrow |
| 3,304,791 | A | | 2/1967 | Robert |
| 3,618,935 | A | * | 11/1971 | Howatt .................. B31B 21/00 198/377.04 |
| 3,705,072 | A | | 12/1972 | Rosvold |
| 3,728,191 | A | | 4/1973 | Wierzba |

(Continued)

FOREIGN PATENT DOCUMENTS

| CH | 678616 | 10/1991 |
| DE | 3323919 | 7/1983 |

(Continued)

OTHER PUBLICATIONS

International Search Report and Written Opinion, PCT/US2016/038288, date of mailing Sep. 28, 2016.

*Primary Examiner* — William R Harp
(74) *Attorney, Agent, or Firm* — Christian M. Best

(57) ABSTRACT

The present disclosure provides a method of transferring discrete articles from a transfer assembly to an apparatus comprising a head. The transfer assembly comprises a frame defining a first rotation axis and a transfer member. The method comprises rotating the transfer member about the first rotation axis and maintaining a transfer surface of the transfer member at a substantially constant minimum distance away from a surface of the head at a point of discrete article transfer. The transfer surface is moved at a first substantially constant tangential velocity at the point of discrete article transfer. The method further comprises rotating the head of the apparatus about a second rotation axis. The surface of the head is moved at a second substantially constant tangential velocity at the point of discrete article transfer. The second tangential velocity of the head is greater than the first tangential velocity of the transfer surface.

21 Claims, 38 Drawing Sheets

(56) References Cited

U.S. PATENT DOCUMENTS

| | | |
|---|---|---|
| 3,963,557 A | 6/1976 | Patterson |
| 4,181,555 A | 1/1980 | Hoffmann |
| 4,220,237 A | 9/1980 | Mohn |
| 4,275,807 A | 6/1981 | Mohn et al. |
| 4,297,157 A | 10/1981 | Van Vliet |
| 4,333,790 A | 6/1982 | Schaffron |
| 4,425,695 A | 1/1984 | Tokuno |
| 4,429,781 A | 2/1984 | Holzhauser |
| 4,456,114 A | 6/1984 | Mohn |
| 4,487,650 A | 12/1984 | Mohn et al. |
| 4,574,022 A | 3/1986 | Johnson et al. |
| 4,578,133 A | 3/1986 | Oshefsky et al. |
| 4,608,115 A | 8/1986 | Schroth et al. |
| 4,610,751 A | 9/1986 | Eschler |
| 4,617,082 A | 10/1986 | Oshefsky et al. |
| 4,632,721 A | 12/1986 | Hoffmann et al. |
| 4,642,150 A | 2/1987 | Stemmler |
| 4,648,928 A | 3/1987 | Ales |
| 4,685,342 A | 8/1987 | Brackett |
| 4,688,902 A | 8/1987 | Gardam |
| 4,722,432 A | 2/1988 | Staton |
| 4,726,874 A | 2/1988 | Van Vliet |
| 4,726,876 A | 2/1988 | Tomsovic, Jr. |
| 4,738,348 A | 4/1988 | Sillner |
| 4,758,293 A | 7/1988 | Samida |
| 4,767,487 A | 8/1988 | Tomsovic, Jr. |
| 4,786,046 A | 11/1988 | Freeman et al. |
| 4,813,946 A | 3/1989 | Sabee |
| 4,821,638 A | 4/1989 | Uithoven |
| 4,834,741 A | 5/1989 | Sabee |
| 4,838,969 A | 6/1989 | Nomura et al. |
| 4,838,982 A | 6/1989 | Klaeser et al. |
| 4,863,542 A | 9/1989 | Oshefsky et al. |
| 4,880,102 A | 11/1989 | Indrebo |
| 4,908,247 A | 3/1990 | Baird et al. |
| 4,911,285 A | 3/1990 | Rogall et al. |
| 4,917,013 A | 4/1990 | Katz |
| 4,921,387 A | 5/1990 | Bennington |
| 4,925,520 A | 5/1990 | Beaudoin et al. |
| 4,940,464 A | 7/1990 | Van Gompel et al. |
| 4,941,939 A | 7/1990 | Nomura et al. |
| 4,960,186 A | 10/1990 | Honda |
| 4,968,313 A | 11/1990 | Sabee |
| 4,995,928 A | 2/1991 | Sabee |
| 5,025,910 A | 6/1991 | Lasure et al. |
| 5,046,272 A | 9/1991 | Vogt et al. |
| 5,091,039 A | 2/1992 | Ujimoto et al. |
| 5,092,861 A | 3/1992 | Nomura et al. |
| 5,092,862 A | 3/1992 | Muckenfuhs et al. |
| 5,104,116 A | 4/1992 | Pohjola |
| 5,116,452 A | 5/1992 | Eder |
| 5,143,679 A | 9/1992 | Weber et al. |
| 5,149,392 A | 9/1992 | Plaessmann |
| 5,156,793 A | 10/1992 | Buell et al. |
| 5,167,897 A | 12/1992 | Weber et al. |
| 5,177,841 A | 1/1993 | Hamuro et al. |
| 5,188,212 A | 2/1993 | Munsch |
| 5,224,405 A | 7/1993 | Pohjola |
| 5,235,515 A | 8/1993 | Ungpiyakul et al. |
| 5,246,433 A | 9/1993 | Hasse et al. |
| 5,275,676 A | 1/1994 | Rooyakkers et al. |
| 5,305,653 A | 4/1994 | Ohtani et al. |
| 5,360,420 A | 11/1994 | Cook et al. |
| 5,380,381 A | 1/1995 | Otruba |
| 5,389,173 A | 2/1995 | Merkatoris et al. |
| 5,413,651 A | 5/1995 | Otruba |
| 5,429,694 A | 7/1995 | Herrmann |
| 5,500,075 A | 3/1996 | Herrmann |
| 5,556,504 A | 9/1996 | Rajala et al. |
| 5,569,234 A | 10/1996 | Buell et al. |
| 5,582,668 A | 12/1996 | Kling |
| 5,584,954 A | 12/1996 | Van der Klugt |
| 5,591,297 A | 1/1997 | Ahr |
| 5,591,298 A | 1/1997 | Goodman et al. |
| 5,599,335 A | 2/1997 | Goldman et al. |
| 5,643,396 A | 7/1997 | Rajala et al. |
| 5,643,588 A | 7/1997 | Roe et al. |
| 5,660,657 A | 8/1997 | Rajala et al. |
| 5,660,664 A | 8/1997 | Herrmann |
| 5,660,665 A | 8/1997 | Jalonen |
| 5,674,216 A | 10/1997 | Buell et al. |
| 5,684,344 A | 11/1997 | Takei |
| 5,693,165 A | 12/1997 | Schmitz |
| 5,693,195 A | 12/1997 | Saito et al. |
| 5,695,963 A | 12/1997 | McKnight et al. |
| 5,702,551 A | 12/1997 | Huber et al. |
| 5,709,770 A | 1/1998 | Asghar et al. |
| 5,716,478 A | 2/1998 | Boothe et al. |
| 5,735,996 A | 4/1998 | Asghar et al. |
| 5,759,340 A | 6/1998 | Boothe et al. |
| 5,766,406 A | 6/1998 | Bohn et al. |
| 5,776,289 A | 7/1998 | Steidinger |
| 5,783,032 A | 7/1998 | O'Callaghan et al. |
| 5,837,087 A | 11/1998 | Ahr |
| 5,849,143 A | 12/1998 | Ingalls |
| 5,850,711 A | 12/1998 | Takahashi et al. |
| 5,888,343 A | 3/1999 | Olson |
| 5,895,555 A | 4/1999 | Van Den Bergh |
| 5,897,545 A | 4/1999 | Kline et al. |
| 5,901,530 A | 5/1999 | Draghetti et al. |
| 5,932,039 A | 8/1999 | Popp et al. |
| 5,957,908 A | 9/1999 | Kline et al. |
| 5,965,963 A | 10/1999 | Chitayat |
| 5,968,025 A | 10/1999 | Roe et al. |
| 5,994,798 A | 11/1999 | Chitayat |
| 6,022,443 A | 2/2000 | Rajala et al. |
| 6,059,710 A | 5/2000 | Rajala et al. |
| 6,074,333 A | 6/2000 | Rajala et al. |
| 6,086,694 A | 7/2000 | Winter et al. |
| 6,107,537 A | 8/2000 | Elder et al. |
| 6,118,041 A | 9/2000 | Roe et al. |
| 6,120,487 A | 9/2000 | Ashton |
| 6,120,489 A | 9/2000 | Johnson et al. |
| 6,139,004 A | 10/2000 | Couillard et al. |
| 6,149,755 A | 11/2000 | McNichols et al. |
| 6,153,209 A | 11/2000 | Vega et al. |
| 6,165,306 A | 12/2000 | Rajala |
| 6,170,636 B1 | 1/2001 | Een et al. |
| 6,250,357 B1 | 6/2001 | Niedermeyer |
| 6,254,714 B1 | 7/2001 | Niedermeyer |
| 6,284,081 B1 | 9/2001 | Vogt et al. |
| 6,287,409 B1 | 9/2001 | Stephany |
| 6,319,347 B1 | 11/2001 | Rajala et al. |
| 6,322,547 B1 | 11/2001 | Hansson |
| 6,325,201 B1 | 12/2001 | Bailey et al. |
| 6,350,070 B1 | 2/2002 | Tasma |
| 6,375,769 B1 | 4/2002 | Quereshi et al. |
| 6,410,129 B2 | 6/2002 | Zhang et al. |
| 6,422,375 B1 | 7/2002 | Hellman et al. |
| 6,426,444 B2 | 7/2002 | Roe et al. |
| 6,431,241 B1 | 8/2002 | Gonzalo |
| 6,440,246 B1 | 8/2002 | Vogt et al. |
| 6,450,321 B1 | 9/2002 | Blumenthal et al. |
| 6,471,036 B1 | 10/2002 | Schlisio |
| 6,520,236 B1 | 2/2003 | Rajala |
| 6,527,902 B1 | 3/2003 | Rajala |
| 6,533,879 B2 | 3/2003 | Quereshi et al. |
| 6,540,857 B1 | 4/2003 | Coenen et al. |
| 6,544,375 B1 | 4/2003 | Schmitz |
| 6,550,517 B1 | 4/2003 | Hilt et al. |
| 6,569,275 B1 | 5/2003 | Popp et al. |
| 6,585,841 B1 | 7/2003 | Popp et al. |
| 6,586,652 B1 | 7/2003 | Roe et al. |
| 6,590,136 B1 | 7/2003 | Young et al. |
| 6,604,623 B2 | 8/2003 | Sumi et al. |
| 6,613,033 B1 | 9/2003 | Popp et al. |
| 6,617,016 B2 | 9/2003 | Zhang et al. |
| 6,617,490 B1 | 9/2003 | Chen et al. |
| 6,620,276 B1 | 9/2003 | Kuntze et al. |
| 6,627,787 B1 | 9/2003 | Roe et al. |
| 6,635,041 B1 | 10/2003 | Popp et al. |
| 6,648,122 B1 | 11/2003 | Hirsch et al. |
| 6,652,504 B1 | 11/2003 | Olson et al. |
| 6,656,312 B1 | 12/2003 | Schmitz et al. |

(56) References Cited

U.S. PATENT DOCUMENTS

| | | |
|---|---|---|
| 6,689,115 B1 | 2/2004 | Popp et al. |
| 6,692,196 B1 | 2/2004 | Simm et al. |
| 6,692,603 B1 | 2/2004 | Lindsay et al. |
| 6,705,453 B2 | 3/2004 | Blumenthal et al. |
| 6,722,494 B2 | 4/2004 | Nakakado |
| 6,748,996 B2 | 6/2004 | Nakakado et al. |
| 6,758,109 B2 | 7/2004 | Nakakado |
| 6,766,217 B1 | 7/2004 | Hamada |
| 6,766,843 B2 | 7/2004 | Hilt et al. |
| 6,808,582 B2 | 10/2004 | Popp et al. |
| 6,811,019 B2 | 11/2004 | Christian et al. |
| 6,814,217 B2 | 11/2004 | Blumenthal et al. |
| 6,820,671 B2 | 11/2004 | Clavert |
| 6,825,393 B2 | 11/2004 | Roe et al. |
| 6,832,679 B2 | 12/2004 | Berndtsson |
| 6,848,566 B2 | 2/2005 | Harnish et al. |
| 6,860,531 B2 | 3/2005 | Sherwin |
| 6,861,571 B1 | 3/2005 | Roe et al. |
| 6,866,137 B2 | 3/2005 | Ohiro et al. |
| 6,895,649 B2 | 5/2005 | Kojo et al. |
| 6,899,780 B2 | 5/2005 | Rajala et al. |
| 6,918,485 B2 | 7/2005 | Holston et al. |
| 6,942,086 B2 | 9/2005 | Bridges et al. |
| 7,013,941 B2 | 3/2006 | Schneider et al. |
| 7,045,031 B2 | 5/2006 | Popp et al. |
| 7,093,705 B2 | 8/2006 | Ohiro et al. |
| 7,134,258 B2 | 11/2006 | Kalany et al. |
| 7,179,343 B2 | 2/2007 | VanEperen et al. |
| 7,195,684 B2 | 3/2007 | Satoh |
| 7,216,685 B2 | 5/2007 | Nakakado et al. |
| 7,252,131 B2 | 8/2007 | Draghetti et al. |
| 7,278,203 B2 | 10/2007 | Aoyama et al. |
| 7,341,087 B2 | 3/2008 | Tabor et al. |
| 7,398,870 B2 | 7/2008 | McCabe |
| 7,533,709 B2 | 5/2009 | Meyer |
| 7,543,697 B2 | 6/2009 | Legallais |
| 7,587,966 B2 | 9/2009 | Nakakado et al. |
| 7,643,904 B2 | 1/2010 | Aoyama et al. |
| 7,721,872 B2 | 5/2010 | Aoyama et al. |
| 7,770,712 B2 | 8/2010 | McCabe |
| 7,841,633 B2 | 11/2010 | Nankervis et al. |
| 7,975,584 B2 | 7/2011 | McCabe |
| 8,281,918 B2 * | 10/2012 | Piantoni ........... A61F 13/15764 198/459.8 |
| 8,430,226 B2 | 4/2013 | Tokunaga et al. |
| 8,607,959 B2 * | 12/2013 | Papsdorf ........... A61F 13/15764 198/377.04 |
| 8,720,666 B2 * | 5/2014 | Papsdorf ........... A61F 13/15764 198/377.01 |
| 8,820,513 B2 * | 9/2014 | Papsdorf ........... A61F 13/15764 198/470.1 |
| 8,833,542 B2 | 9/2014 | Papsdorf et al. |
| 8,944,235 B2 | 2/2015 | Papsdorf et al. |
| 9,221,621 B2 | 12/2015 | Papsdorf et al. |
| 9,227,794 B2 | 1/2016 | Papsdorf et al. |
| 9,266,684 B2 | 2/2016 | Papsdorf et al. |
| 9,283,121 B1 | 3/2016 | Papsdorf et al. |
| 2002/0112939 A1 | 8/2002 | Sumi et al. |
| 2002/0125105 A1 | 9/2002 | Nakakado |
| 2003/0079330 A1 | 5/2003 | Stopher et al. |
| 2003/0233082 A1 | 12/2003 | Kline et al. |
| 2004/0089516 A1 | 5/2004 | Christian et al. |
| 2004/0144619 A1 | 7/2004 | Ohiro et al. |
| 2004/0144620 A1 | 7/2004 | Ohiro et al. |
| 2004/0154161 A1 | 8/2004 | Aoyama et al. |
| 2004/0245069 A1 | 12/2004 | Hook et al. |
| 2004/0262127 A1 | 12/2004 | Harnish et al. |
| 2005/0082141 A1 | 4/2005 | Dombek |
| 2006/0185135 A1 | 8/2006 | Yamamoto et al. |
| 2007/0040301 A1 | 2/2007 | Jackson |
| 2007/0074953 A1 | 4/2007 | McCabe |
| 2007/0227858 A1 | 10/2007 | Aoyama et al. |
| 2008/0005895 A1 | 1/2008 | Aoyama et al. |
| 2008/0023296 A1 | 1/2008 | Aoyama et al. |
| 2008/0196564 A1 | 8/2008 | McCabe |
| 2008/0276439 A1 | 11/2008 | Andrews et al. |
| 2009/0312739 A1 | 12/2009 | Umebayahi et al. |
| 2010/0012458 A1 | 1/2010 | Giuliani et al. |
| 2010/0258240 A1 | 10/2010 | Mccabe et al. |
| 2010/0270126 A1 | 10/2010 | Piantoni et al. |
| 2010/0300838 A1 | 12/2010 | McCabe |
| 2010/0326796 A1 | 12/2010 | Walsh |
| 2011/0287918 A1 | 11/2011 | Ogasawara et al. |
| 2012/0012439 A1 | 1/2012 | Yamamoto |
| 2013/0091998 A1 | 4/2013 | Yamamoto et al. |
| 2013/0152360 A1 | 6/2013 | Schoultz et al. |
| 2013/0153365 A1 | 6/2013 | Schoultz |
| 2014/0110052 A1 | 4/2014 | Findley et al. |
| 2014/0110226 A1 | 4/2014 | Findley et al. |
| 2014/0174883 A1 | 6/2014 | Papsdorf et al. |
| 2014/0202830 A1 | 7/2014 | Papsdorf et al. |
| 2014/0346010 A1 | 11/2014 | Papsdorf et al. |

FOREIGN PATENT DOCUMENTS

| | | |
|---|---|---|
| EP | 0812789 | 12/1997 |
| EP | 0997123 | 5/2000 |
| JP | 01131372 | 5/1989 |
| JP | 2005212149 | 8/2005 |
| WO | WO-9519752 | 7/1995 |
| WO | WO-2010-071069 | 6/2010 |
| WO | WO-2010-078572 | 7/2010 |
| WO | WO-2011-118491 | 9/2011 |

* cited by examiner

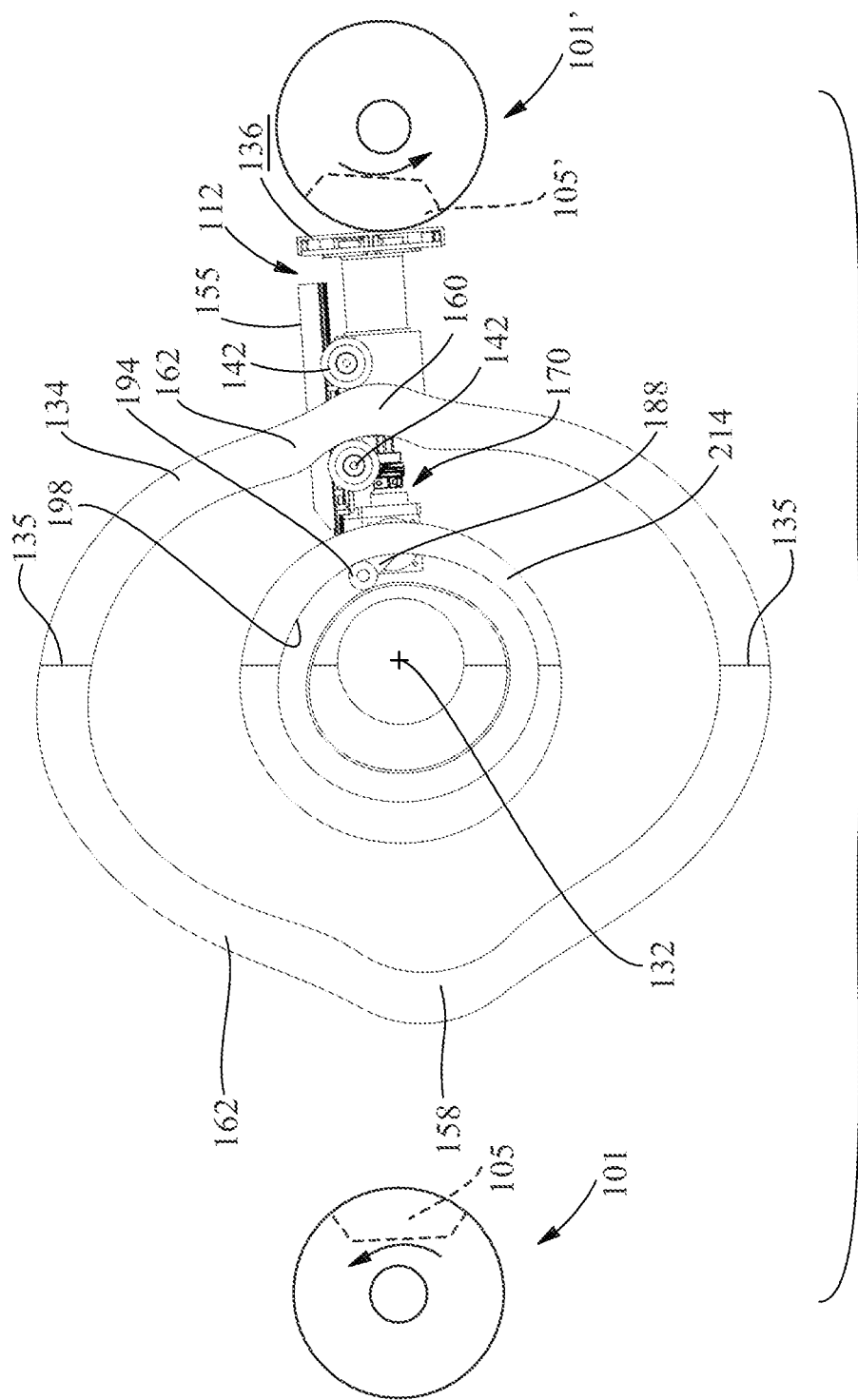

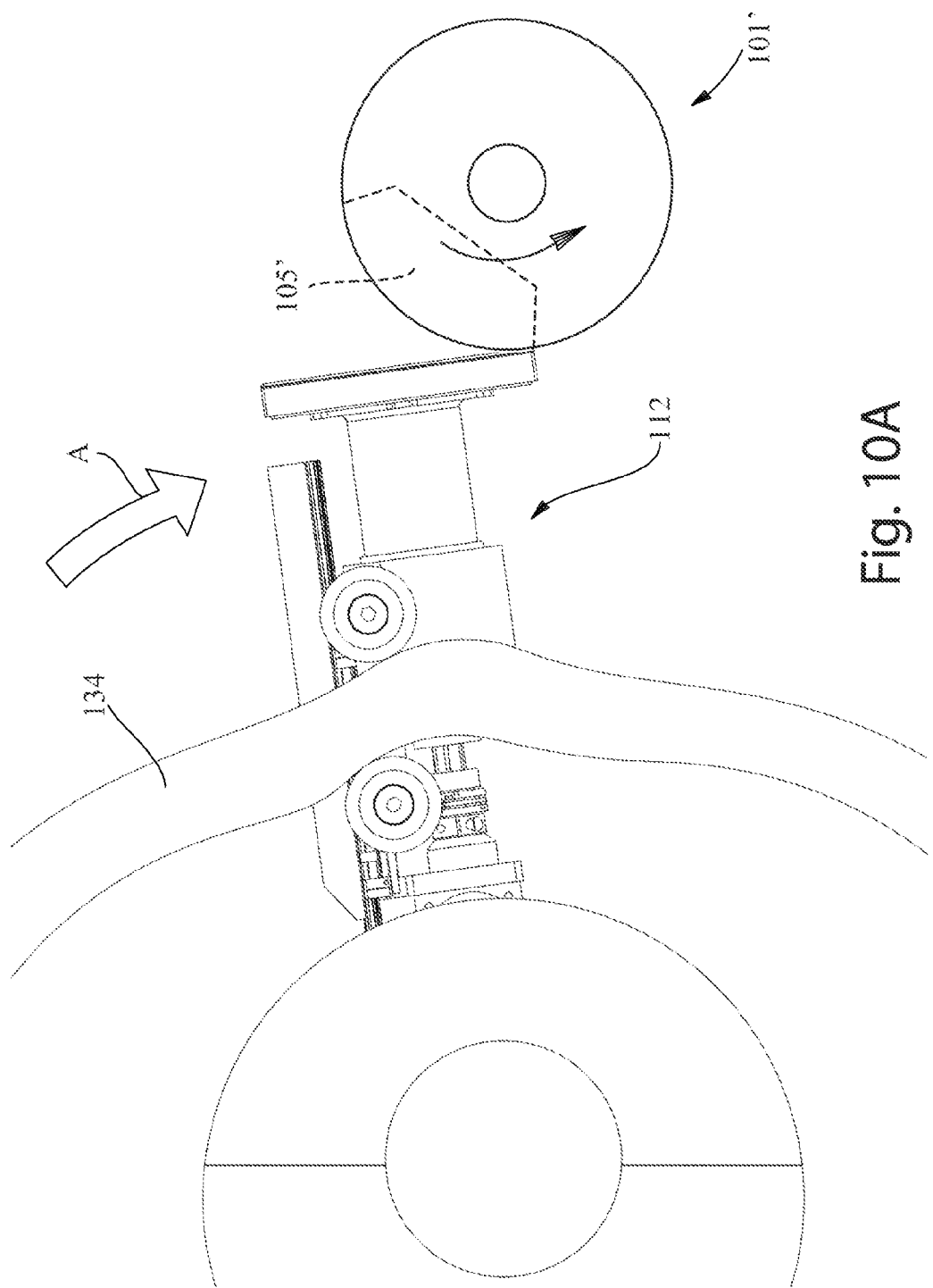

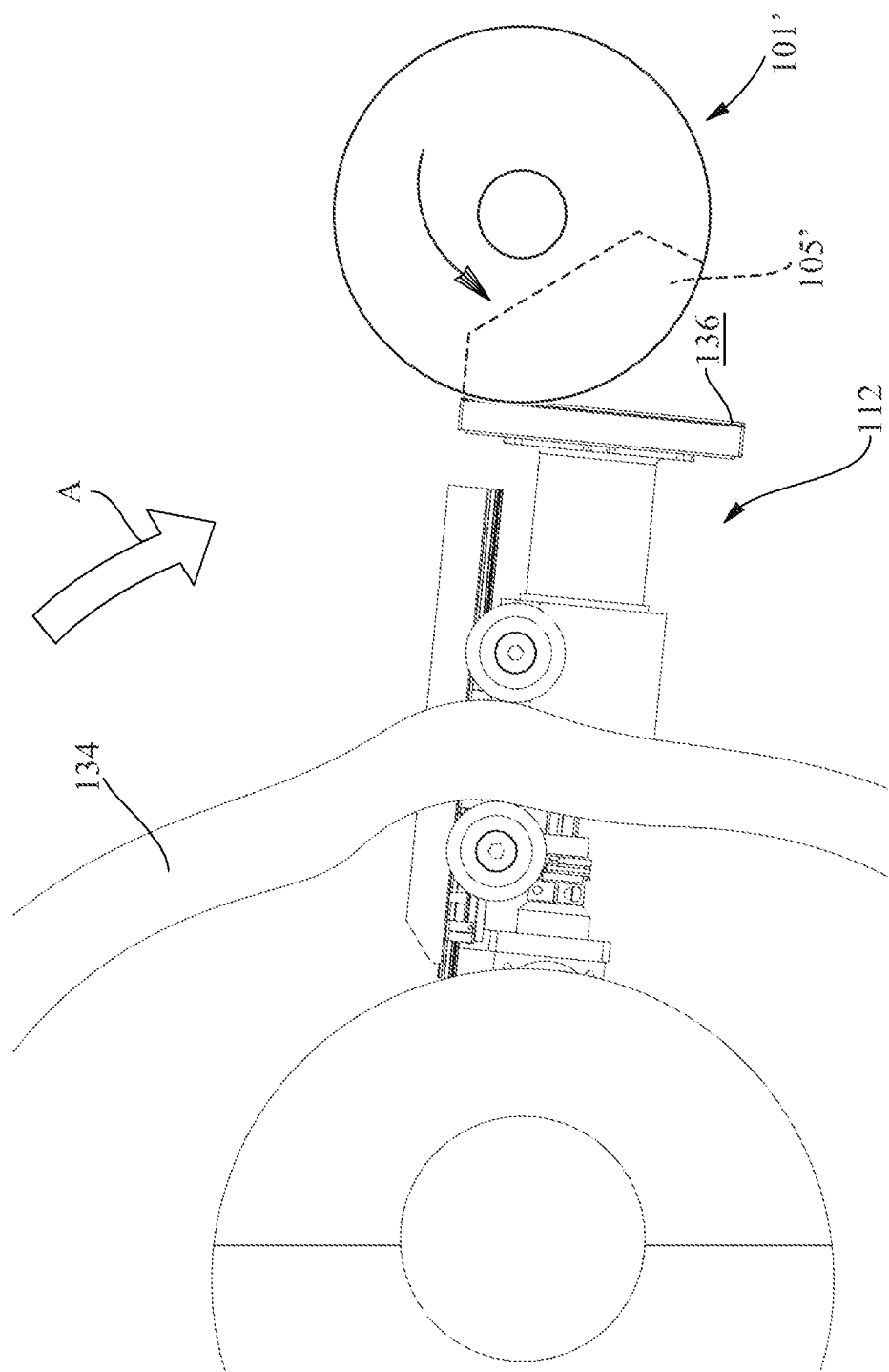

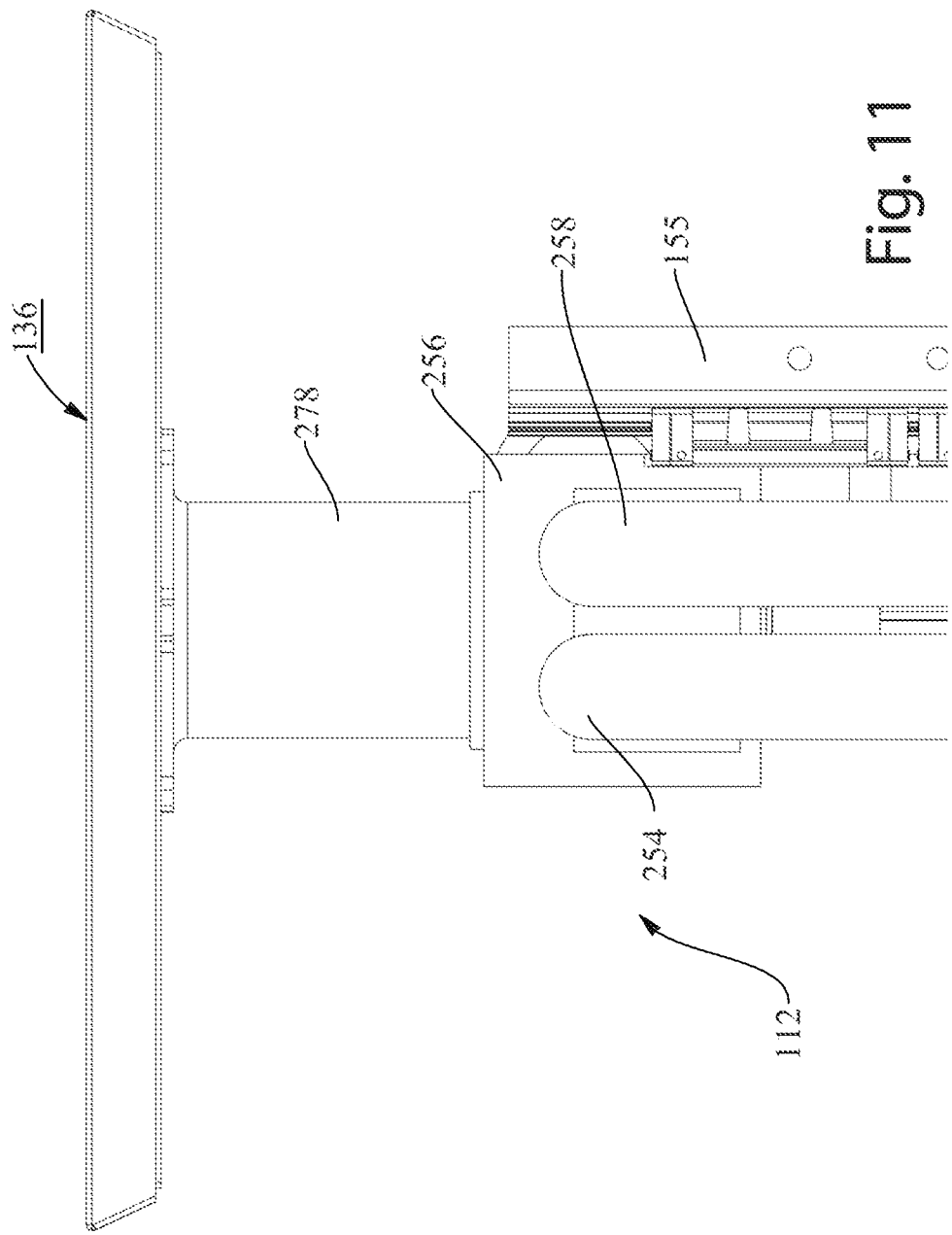

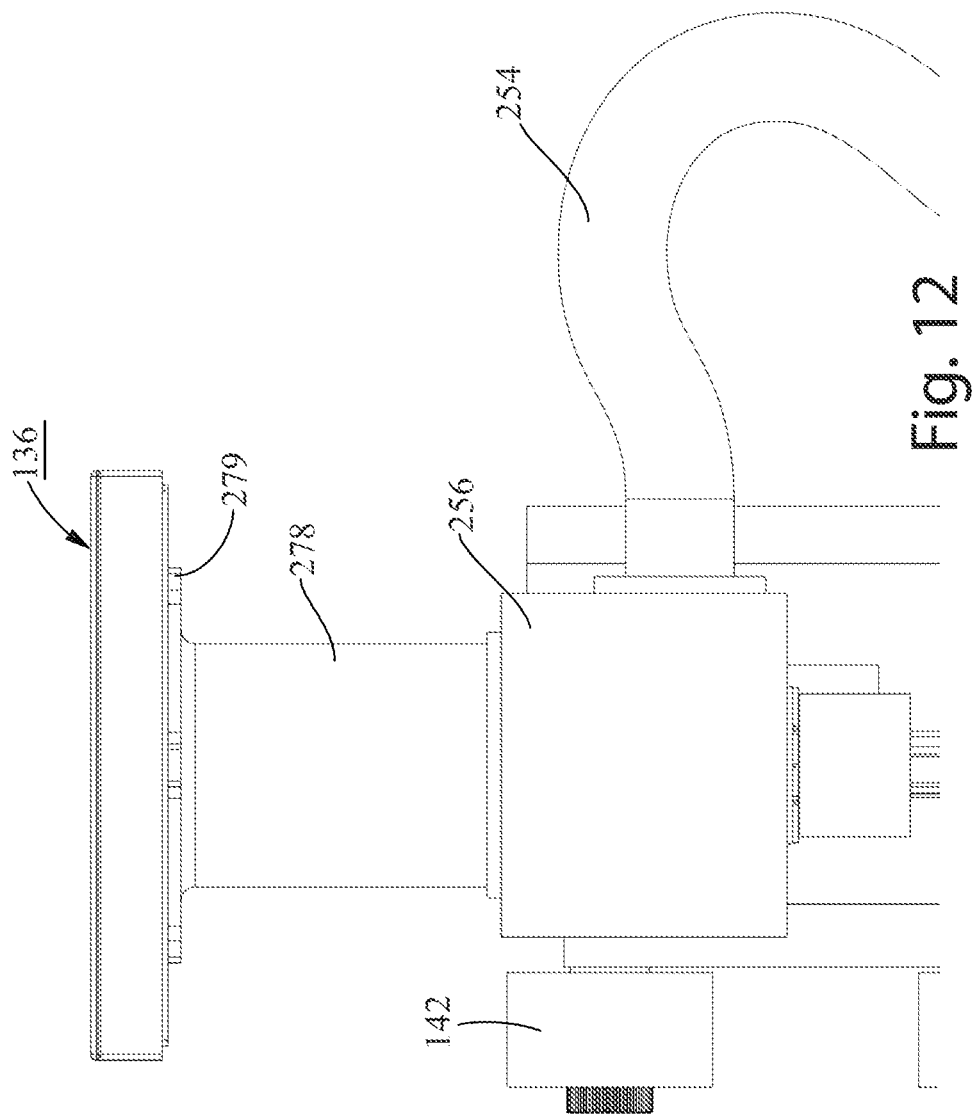

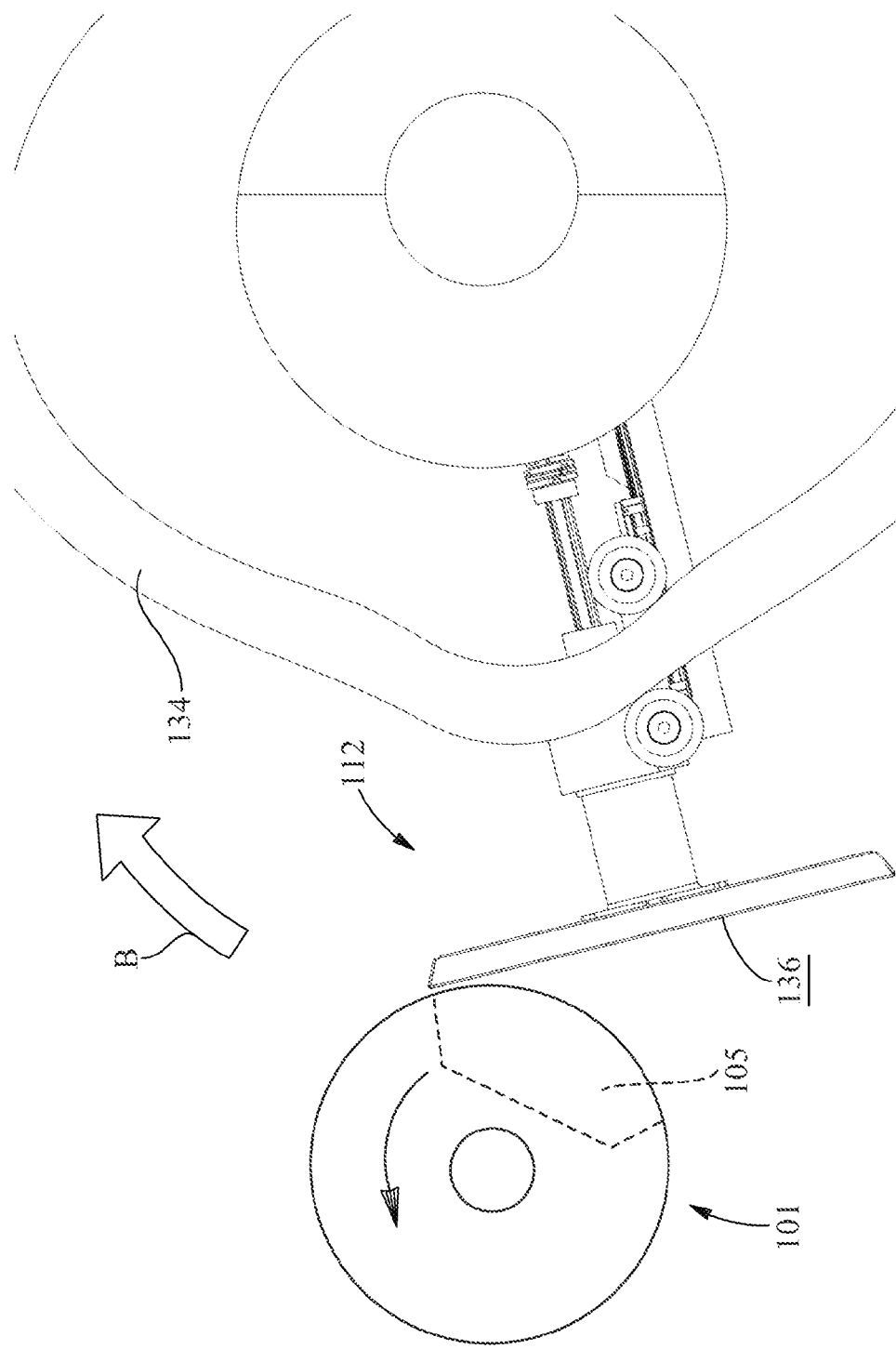

METHODS FOR TRANSFERRING DISCRETE ARTICLES

FIELD

The present disclosure generally relates to methods for transferring discrete articles and, more particularly, relates to methods for transferring discrete articles to or from an apparatus comprising one or more heads.

BACKGROUND

Absorbent articles, such as taped diapers or pant diapers, for example, may be manufactured by a process where discrete articles, such as a chassis of a taped diaper or a pant diaper comprising a topsheet, a backsheet, and an absorbent core, for example, are applied to one or more moving webs of components, such as webs of front and rear belt portions, for example. To achieve this, a transfer assembly may be provided that comprises one or more transfer members and a frame defining a rotation axis. The transfer member(s) may orbit about the rotation axis. Each of the transfer members may comprise a transfer surface that is configured to engage one or more of the discrete articles. The transfer members may pick up the discrete articles at a pick-up location and place the discrete articles at a drop-off location within the orbit. In certain instances, the transfer assembly may rotate the discrete articles about 90 degrees, or other suitable angles, between the pick-up location and the drop-off location about a second rotation axis that is perpendicular, or substantially perpendicular, to the rotation axis. Transfer assemblies that rotate and transfer discrete articles are known in the art as "turn and repitch" units because the units turn the discrete articles and repitch them (i.e., change the spacing or "pitch" between them) between the pick-up location and the drop-off location. The repitching capability of these units, however, is somewhat limited and frequent change-outs of the entire transfer assemblies, or portions thereof, typically must be done to transfer discrete articles having different sizes (e.g., different MD widths and/or different CD lengths). This is owing to the fact that the transfer members of typical transfer assemblies orbit about the rotation axis at a constant angular velocity, thereby reducing or eliminating any pitch variation at the drop-off location. Differently sized discrete articles may require different drop off pitches at the drop-off location.

What is needed are methods for transferring discrete articles that overcome the repitching limitations and frequent change-outs of related art discrete article transfer methods.

SUMMARY

The present disclosure provides for transfer assemblies that transfer discrete articles to or from an apparatus comprising one or more heads. The transfer assemblies may comprise a frame defining a rotation axis and one or more transfer members. Each transfer member is configured to orbit about the rotation axis at a constant, or substantially constant, angular velocity. The transfer members each comprise a transfer surface configured to receive one or more of the discrete articles. The transfer surface may be flat, substantially flat, or may comprise a portion that is flat or substantially flat. The transfer assembly may transfer the discrete articles to and/or from the apparatus comprising the one or more heads. Stated another way, the apparatus comprising the one or more heads may be positioned on the input side of the transfer assembly, on the output side of the transfer assembly, or on both the input and output sides of the transfer assembly. The one or more heads of the apparatus rotate about a rotation axis of the apparatus at a variable angular velocity or at a plurality of angular velocities. By rotating the heads at a variable angular velocity, a significantly expanded range of input or output pitches of the discrete articles are provided by the combination of the transfer assembly and the apparatus(es) compared to only using the related art transfer assemblies. By providing such an apparatus(es) in combination with a transfer assembly that rotates its transfer members at a constant angular velocity, the transfer assembly does not need to be changed out as frequently and can run more than one size of discrete articles because of the increased pitch range that the combination provides.

In a form, the present disclosure is directed, in part, to a method of transferring discrete articles between a transfer assembly and an apparatus comprising one or more heads. The transfer assembly may comprise a frame defining a first rotation axis and at least one transfer member each comprising a transfer surface configured to receive one of the discrete articles. The method may comprise rotating the at least one transfer member of the transfer assembly about the first rotation axis at a constant, or substantially constant, angular velocity, maintaining the transfer surface at a substantially constant minimum distance away from a surface of the head at a point or zone of discrete article transfer, and rotating the at least one head of the apparatus about a second rotation axis at a plurality of angular velocities. A first angular velocity of the head may be constant, or substantially constant, at the point or zone of discrete article transfer.

In another form, the present disclosure is directed, in part, to a method of transferring discrete articles between a transfer assembly and an apparatus comprising one or more heads. The transfer assembly may comprise a frame defining a first rotation axis and at least one transfer member each comprising a transfer surface configured to receive one or more of the discrete articles. The method may comprise rotating the at least one transfer member of the transfer assembly about the first rotation axis at a constant, or substantially constant, angular velocity and maintaining the at least one transfer surface at a constant, or substantially constant, minimum distance away from a surface of the at least one head at a point or zone of discrete article transfer. A tangential velocity of the at least one transfer surface may be constant, or substantially constant, at the point or zone of discrete article transfer. The method may further comprise rotating the at least one head of the apparatus about a second rotation axis at a variable angular velocity. A first angular velocity of the at least one head may be constant, or substantially constant, at the point or zone of discrete article transfer. A tangential velocity of the surface of the head may be substantially the same as the constant, or substantially constant, tangential velocity of the at least one transfer surface at the point or zone of discrete article transfer.

In still another form, the present disclosure is directed, in part, to a method of transferring discrete articles between a transfer assembly and an apparatus comprising one or more heads. The transfer assembly may comprise a frame defining a first rotation axis and at least one transfer member each comprising a transfer surface configured to receive one of the discrete articles. The transfer surface may be flat, substantially flat, or may comprise a flat, or substantially flat, portion. The method may comprise rotating the at least one transfer member of the transfer assembly about the first rotation axis at a constant, or substantially constant, angular velocity, maintaining the transfer surface at a constant, or substantially constant, minimum distance away from a surface of the at least one head at a point or zone of discrete article transfer, and rotating the at least one head of the apparatus about a second rotation axis at a variable angular velocity.

In still another form, the present disclosure is directed, in part, to a method of transferring discrete articles from a transfer assembly to an apparatus comprising one or more heads. The transfer assembly may comprise a frame defining a first rotation axis and at least one transfer member each comprising a transfer surface configured to receive one or more of the discrete articles. The method may comprise rotating the at least one transfer member of the transfer assembly about the first rotation axis and maintaining the transfer surface at a constant, or substantially constant, minimum distance away from a surface of the at least one head at a point or zone of discrete article transfer. The transfer surface may be moved at a first constant, or substantially constant, tangential velocity at the point or zone of discrete article transfer. The method may further comprise rotating the at least one head of the apparatus about a second rotation axis. The surface of the at least one head may be moved at a second constant, or substantially constant, tangential velocity at the point or zone of discrete article transfer. The second, constant, or substantially constant, tangential velocity of the head may be greater than the first substantially constant tangential velocity of the transfer surface to tension the discrete articles being transferred at the point or zone of discrete article transfer.

In yet another form, the present disclosure is directed, in part, to a method of transferring discrete articles from a transfer assembly to an apparatus comprising one or more heads. The transfer assembly may comprise a frame defining a first rotation axis and one or more transfer members each comprising a transfer surface configured to receive one of the discrete articles. The method may comprise rotating the at least one transfer member of the transfer assembly about the first rotation axis at a constant, or substantially constant, angular velocity and maintaining the transfer surface at a constant, or substantially constant, minimum distance away from a surface of the at least one head at a point or zone of discrete article transfer. The transfer surface may be moved at a first constant, or substantially constant, tangential velocity at the point or zone of discrete article transfer. The method may further comprise rotating the at least one head of the apparatus about a second rotation axis at a variable angular velocity. The surface of the at least one head may be moved at a second constant, or substantially constant, tangential velocity at the point or zone of discrete article transfer. The second constant, or substantially constant, tangential velocity of the head may be greater than the first constant, or substantially constant, tangential velocity of the transfer surface.

In yet another form, the present disclosure is directed, in part, to a method of transferring discrete articles from a transfer assembly to an apparatus comprising one or more heads. The transfer assembly may comprise a frame defining a first rotation axis and at least one transfer member each comprising a transfer surface configured to receive one or more of the discrete articles. The transfer surface may be substantially flat, flat, or may comprise a flat portion. The method may comprise rotating the at least one transfer member of the transfer assembly about the first rotation axis and maintaining the transfer surface at a constant, or substantially constant, minimum distance away from a surface of the at least one head at a point or zone of discrete article transfer. The transfer surface may be moved at a first constant, or substantially constant, tangential velocity at the point or zone of discrete article transfer. The method may further comprise rotating the at least one head of the apparatus about a second rotation axis. The surface of the at least one head may be moved at a second constant, or substantially constant, tangential velocity at the point or zone of discrete article transfer. The second constant, or substantially constant, tangential velocity of the at least one head may be greater than the first constant, or substantially constant, tangential velocity of the transfer surface to tension the discrete articles being transferred at the point or zone of discrete article transfer.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein:

FIG. 10 is a rear view of two tracks, a transfer member and a rotation assembly movably engaged with the two tracks, and portions of two apparatuses comprising heads in accordance with the present disclosure;

FIGS. 10A-10C are rear views of a portion of the transfer assembly having a transfer member and transfer surface, wherein the progression of movement of the transfer surface relative to a second apparatus comprising a head is illustrated, in accordance with the present disclosure;

FIG. 11 is a side view of a portion of transfer member comprising a flat, or substantially flat, transfer surface in accordance with the present disclosure;

FIG. 12 is a front view of the portion of the transfer member of FIG. 11 having the flat, or substantially flat, transfer surface in accordance with the present disclosure;

FIGS. 13A-13C are rear views of a portion of the transfer assembly having a transfer member and transfer surface, wherein the progression of movement of the transfer surface relative to a first apparatus comprising a head is illustrated, in accordance with the present disclosure;

DETAILED DESCRIPTION

Figure 1:
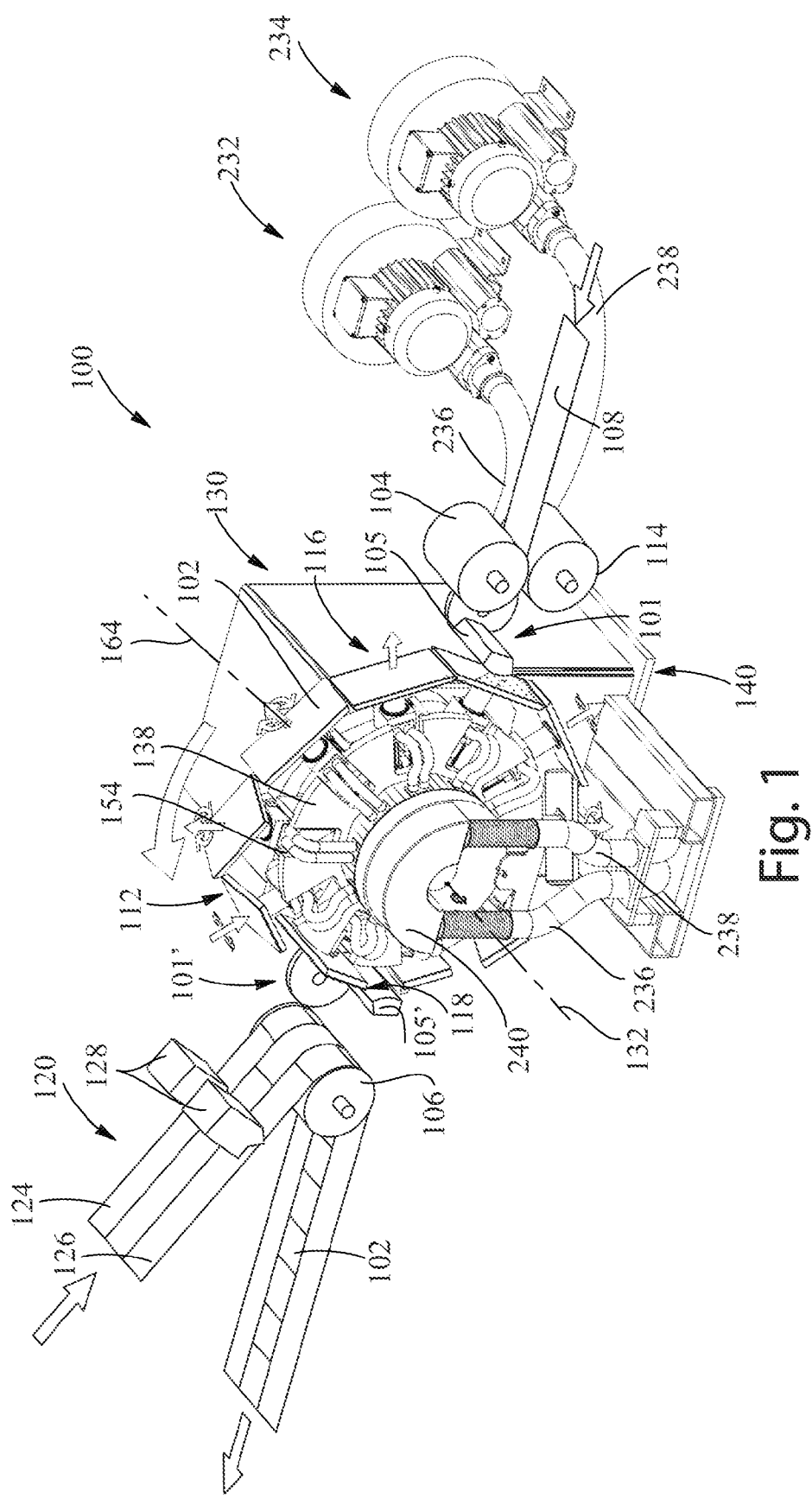
FIG. 1 is a front perspective view of a transfer assembly configured to transfer a discrete article from a first apparatus comprising a head to a second apparatus comprising a head in accordance with the present disclosure.

Various non-limiting forms of the present disclosure will now be described to provide an overall understanding of the principles of the structure, function, manufacture, and use of the methods for transferring discrete articles disclosed herein. One or more examples of these non-limiting forms are illustrated in the accompanying drawings. Those of ordinary skill in the art will understand that the methods for transferring discrete articles described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

The term "absorbent article(s)" refers herein to consumer products whose primary function is to absorb and retain bodily exudates and wastes. Absorbent articles as used herein may refer to pants, taped diapers, and/or sanitary napkins (e.g., feminine hygiene products). The term "absorbent articles" also specifically includes adult incontinence products, in any form. In some instances, absorbent articles may comprise or be formed into pants, taped diapers, or sanitary napkins. The terms "diaper" and "pants" are used herein to refer to absorbent articles generally worn by infants, children, and/or incontinent persons about the lower torso.

The term "disposable" is used herein to describe absorbent articles which generally are not intended to be laundered or otherwise restored or reused as an absorbent article (e.g., they are intended to be discarded after a single use and may also be configured to be recycled, composted, or otherwise disposed of in an environmentally compatible manner).

The term "nonwoven" or "nonwoven material" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) refers herein to the primary direction of material, web, or article flow through a process. In various manufacturing and converting processes, such as a bi-fold process, it may be possible to have more than one machine direction when an article is undergoing simultaneous processes. In other words, a manufacturing line may have an overall machine direction, but a material or an article may travel in directions other than the overall machine direction as it passes through various processes along the manufacturing line. For example, a discrete article having a trailing end portion and a leading end portion, each portion being attached to the surface of a different roll and/or conveyor may travel in two different directions simultaneously. In this example, both directions of travel may be considered the machine direction.

The term "cross direction" (CD) refers herein to a direction that is perpendicular to the machine direction.

The term "taped diaper" refers herein to disposable absorbent articles having an initial front waist region and an initial rear waist region that are not fastened, pre-fastened, or connected to each other as packaged, prior to being applied to the wearer. A taped diaper may be folded about its lateral central axis with the interior of one waist region in surface to surface contact with the interior of the opposing waist region without fastening or joining the waist regions together. Example taped diapers in various configurations are disclosed in U.S. Pat. Nos. 5,167,897, 5,360,420, 5,599, 335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571.

The term "pant" refers herein to disposable absorbent articles having a continuous perimeter waist opening and continuous perimeter leg openings designed for infant, child, or adult wearers. A pant may be configured with a continuous or closed waist opening and at least one continuous, closed, leg opening prior to the article being applied to the wearer. A pant may be preformed by various techniques including, but not limited to, joining together portions of the absorbent article using any refastenable and/or permanent closure member (e.g., seams, heat bonds, pressure welds, adhesives, cohesive bonds, mechanical fasteners, etc.). A pant may be preformed anywhere along the circumference of the absorbent article in the waist region (e.g., side fastened or seamed, front waist fastened or seamed, rear waist fastened or seamed). A pant may be opened about one or both of the side seams and then refastened. Example pants in various configurations are disclosed in U.S. Pat. Nos. 5,246,433, 5,569,234, 6,120,487, 6,120,489, 4,940,464, 5,092,861, 5,897,545, 5,957,908, and U.S. Patent Publication No. 2003/0233082.

The term "discrete article(s)" refers herein to absorbent articles, pants, taped diapers, sanitary napkins, bandages, medical pads and dressings, and any other suitable articles, in any industry, capable of being transferred using the transfer apparatuses and methods of the present disclosure. Discrete articles may also refer herein to portions of the absorbent articles, pants, taped diapers, sanitary napkins, bandages, medical pads and dressings, and other suitable articles. The discrete articles may be flexible. In one example, discrete articles may refer herein to a chassis of a taped diaper or a pant. The chassis may comprise a topsheet, a backsheet, an optional single or dual layer acquisition system, and an absorbent core disposed between at least a portion of the topsheet and the backsheet. The chassis may also comprise stretched elastic elements such as leg elastics and inner barrier leg cuff elastics, for example.

In various forms, referring to FIG. 1, the present disclosure provides, in part, transfer assemblies (e.g., 100) and transfer members associated with the transfer assemblies, in combination with one or more apparatuses 101 and 101' each comprising one or more heads, for transferring discrete articles and/or flexible discrete articles. A transfer assembly and at least one of the apparatuses may be referred to herein as the "overall transfer apparatus." An apparatus comprising one or more heads may be positioned at the input side of the transfer assembly (on the side of element 104), at the output side of the transfer assembly (on the side of element 106), or at both the input and output sides. The one or more heads of the apparatuses may be rotated at variable angular velocities about a rotation axis of the apparatuses such that the apparatuses may provide a greater input pitch range and/or a greater output pitch range to the overall transfer apparatus, as is described in further detail herein. By providing an apparatus at the input and/or output sides of the transfer assembly, the same transfer assembly may be used to transfer an increased size range (e.g., MD and CD sizes) of discrete articles without frequently and costly change-outs of the transfer assemblies. Typically, transfer members of transfer assemblies have a constant angular velocity, thereby limiting their input and output pitch ranges. By providing an apparatus comprising one or more heads in combination with the transfer assembly greater input and output pitch ranges can be achieved at a pick-up location or a drop-off location.

The present disclosure also provides, in part, methods for transferring the discrete articles using the transfer assemblies and the one or more apparatuses each comprising one or more heads. A chassis of a pant or a taped diaper, for example, may be picked up by a transfer member of the transfer assembly at a pick-up location while moving at a first speed and may be transferred to a head of an apparatus. The apparatus may then place the chassis onto a moving or rotating carrier member, a linear conveyor, or another head at drop-off location at a second speed that is different than or the same as the first speed. Alternatively, a head of an apparatus may provide the chassis to a transfer member of the transfer assembly at the pick-up location at a first speed and the transfer member may then place the chassis onto a moving or rotating carrier member at a drop-off location at a second, different speed. Again alternatively, a head of an apparatus may provide the chassis to a transfer member at the pick-up location. The transfer member may then place the discrete article onto a head of another apparatus and the head may then place the discrete article onto a moving or rotating carrier member, a linear conveyor, other type of conveyor, or another head, at a drop-off location. As discussed above, by providing the apparatus on the input and/or output sides of the transfer assembly, the input and/or output pitch ranges can be significantly increased compared to using only a transfer assembly and two moving or rotating carrier members. These increased pitch ranges are at least partially contributable to the variable angular velocity of the heads of the apparatuses.

The discrete articles may be transferred from the pick-up location (e.g., output of roll 104) to the drop-off location (e.g., input of roll 106) by the overall transfer apparatus to change the speed and/or pitch of the discrete articles and/or to turn the discrete articles, for example. Components, such as webs of front and rear belts or discrete front and rear belts, either of which may be configured to together form a portion of a belt in a pant, for example, may be moving over a moving or rotating carrier member, a linear conveyor, or other conveyor in the drop-off location. The moving or rotating carrier member or linear conveyor in the drop-off location may have a first portion carrying the web of front belts and a second portion carrying a web of rear belts. In other instances, the moving or rotating carrier member or linear conveyor may comprise two separate moving or rotating carrier members or linear conveyor; one carrying the web of front belts and the other carrying the web of rear belts. If webs of front and rear belts are provided on the moving or rotating carrier member or the linear conveyor, the chassis may be placed on the transfer member (either from moving carrier member 104 or head of the apparatus 101, if present), turned, then transferred to a head of the apparatus 101'. The apparatus 101' may then apply the chassis to the moving or rotating carrier member or linear conveyor in the drop-off location so as to apply the waist regions of the chassis to the first and second webs of front and rear belts. A first waist region of the chassis may be applied to the web of first belts and a second waist region of the chassis may be applied to the web of second belts to form an intermediate absorbent article that can be formed into a pant or a taped diaper, for example. The waist regions of the chassis may be glued to the webs of belts or otherwise attached to the webs of belts. Further details regarding this example transfer are provided herein.

The overall transfer apparatus of the present disclosure may be able to turn the discrete articles intermediate the pick-up location and the drop-off location for placement onto one or more webs of components or discrete components traveling over the moving or rotating carrier member or linear conveyor (hereafter sometimes referred to as a "moving carrier member") or onto the moving carrier member without being placed on discrete components. In one example, a portion of a transfer member of a transfer assembly may receive a discrete article, such as a taped diaper or pant chassis, for example, from a moving carrier member and turn it between a first position and a second position (e.g., a 90 degree turn to the discrete article). Then, the discrete article may be transferred by the transfer member to a head of the apparatus 101'. After which, the apparatus 101' may apply the discrete article onto webs of front and rear belts traveling on the moving carrier member to form an absorbent article that may be formed into a taped diaper or a pant, for example.

As discussed above, the overall transfer apparatuses may also be configured to repitch the discrete articles between the pick-up location and the drop-off location. This "repitching" is changing the machine direction spacing between midpoints of the discrete articles relative to each other. In an instance, the machine direction pitch of the discrete articles in the pick-up location may be smaller or larger than the machine direction pitch of the discrete articles in the drop-off location. The apparatus (or apparatuses) comprising the head(s) of the present disclosure aids in providing an overall transfer apparatus that may provide a greater range of input and/or output pitches compared to transfer assemblies used without the apparatus. This is owing to the variable angular velocity of the heads. In other instances, the pitch of the discrete articles may not be changed between the pick-up and drop-off locations. In various forms, the overall transfer apparatus of the present disclosure may not turn the discrete articles between the pick-up and drop-off locations, although they may have the ability to do so. In other instances, the overall transfer apparatuses may not have the ability to turn the discrete articles during a transfer between the pick-up and drop-off locations.

It is to be appreciated that the methods and apparatuses of the present disclosure may also be suitable for any other uses that require transfer of a discrete article or a discrete component from a pick-up location to a drop-off location, regardless of the desired speed of the discrete articles at the pick-up location and at the drop-off location, and regardless of whether the discrete articles or discrete components need to be turned and/or repitched. These other uses may comprise various manufacturing processes for any product, or intermediate product, in any industry.

Figure 2:
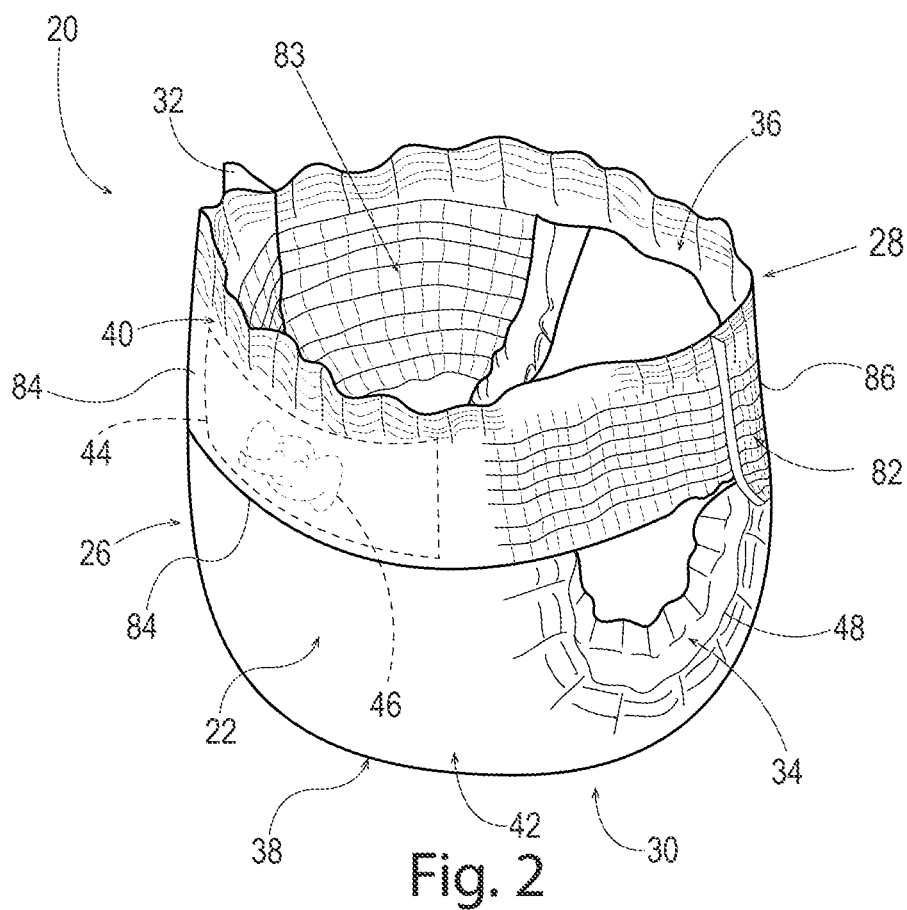
FIG. 2 is a perspective view of a pant in accordance with the present disclosure.
Figure 3:
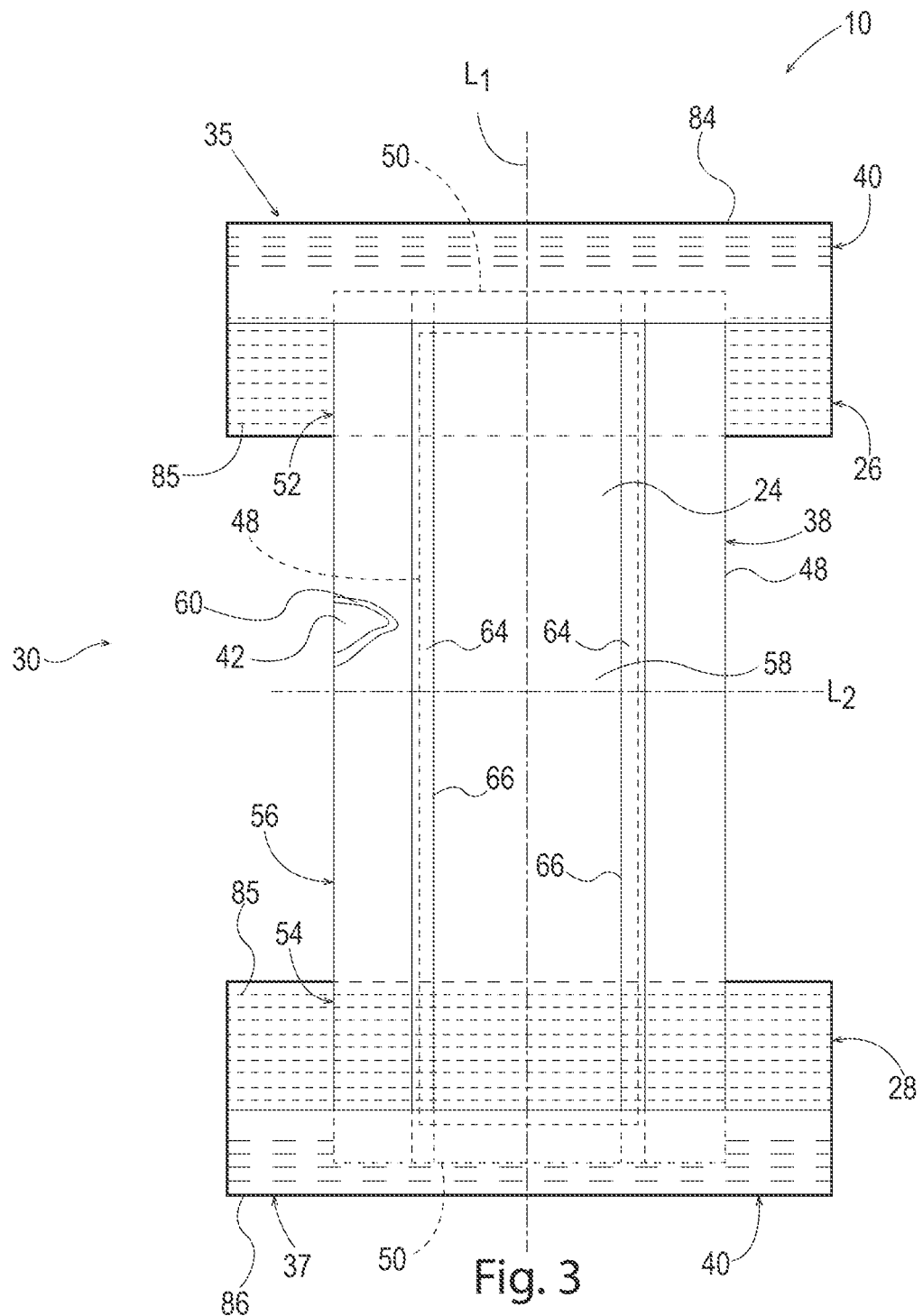
FIG. 3 is a schematic illustration of an absorbent article capable of being formed into the pant of FIG. 2 in accordance with the present disclosure.

FIG. 2 illustrates an example of a pant 20 that may be at least partially formed or manufactured using the overall transfer apparatuses of the present disclosure. FIG. 3 illustrates an absorbent article 10 that can be formed into the pant 20 of FIG. 2. Those of skill in the art will recognize that FIGS. 2 and 3 are merely examples of one absorbent article that may be formed, or at least partially manufactured, using the overall transfer apparatuses of the present disclosure. Many other products, including other absorbent articles, pants, taped diapers, sanitary napkins, cleaning pad or substrates, dusting pads or substrates, wipes, or portions thereof, may be formed, or at least partially manufactured, using the overall transfer apparatuses of the present disclosure. The absorbent article 10 has a longitudinal central axis L1 and a lateral central axis L2 (see FIG. 3). The pant 20 has an outer surface 22, an inner surface 24 opposed to the outer surface 22, a front waist region 26, a rear waist region 28, a crotch region 30, and seams 32 which join the front waist region 26 and the rear waist region 28 to form two leg openings 34 and a waist opening 36. The seams 32 may be permanent or refastenable. When referring to "pant 20" herein, it will be understood that the absorbent article 10, although not yet formed into the pant 20, may be considered a "pant". It will be understood that the pant 20 is disclosed as an example, but that a taped diaper may also be formed from the absorbent article 10 merely by adding fastening elements and/or landing zones to one or both of the front and rear belts 84 and 86. Referring to FIGS. 2 and 3, the pant 20 may comprise an absorbent chassis 38 to cover a crotch region of a wearer and a belt 40 extending transversely about the waist opening 36. The pant 20 may also optionally comprise an outer cover layer 42 to cover the chassis 38. The belt 40 may define the waist opening 36 in the pant 20. The belt 40, the chassis 38, and/or the outer cover layer 42 may jointly define the leg openings 34. In some circumstances, the pant 20 may have a patch sheet 44 printed with a graphic 46 thereon, which may be disposed in the front waist region 26, the rear waist region 28, or any other suitable portion of the pant 20. The belt 40 may be formed from a front belt 84 in the front waist region 26 and a rear belt 86 in the rear waist region 28. The front belt 84 may form a front waist edge 35 in the front waist region 26 and the rear belt 86 may form a rear waist edge 37 in the rear waist region 28. The front and rear waist edges 35 and 37 may be laterally opposed about the lateral central axis L2. The belt 40 may form a portion of an outer surface 22 or an inner surface 24 of the pant 20. In other instances, the belt 40, or portions thereof, may be disposed intermediate other layers of the chassis 38, such as a topsheet and a backsheet, for example.

The absorbent chassis 38 may absorb and contain body exudates or wastes disposed on the chassis 38. Referring to FIG. 3, the chassis 38 may have a generally rectangular shape having left and right longitudinally extending side edges 48 (hereinafter may be referred to as "longitudinal side edge") and front and rear laterally extending end edges 50 (hereinafter may be referred to as "lateral end edge"). The chassis may also have any other suitable shape, such as an hourglass shape. The chassis 38 may also comprise waist panels (i.e., a front waist panel 52 positioned in the front waist region 26 and a rear waist panel 54 positioned in the rear waist region 28) and a crotch panel 56 in the crotch region 30 between the front and rear waist panels 52, 54.

The pant 20 may comprise front and rear belts 84 and 86 intended to encircle at least a portion of the waist of the wearer. The front and rear belts 84 and 86 together form at least a portion of, or all of, the belt 40 when joined. The front and rear belts 84 and 86 may be connected by the chassis 38 forming the crotch region 30 of the pant 20. The front and rear belts 84 and 86 may each be formed from a first belt layer 82 possibly forming a portion of the outer surface 22 of the pant 20 and a second belt layer 83 possibly forming a portion of the inner surface 24 of the pant 20. The first and second belt layers 82 and 83 may be comprised of any known materials. Various suitable materials may comprise films, plastic films, apertured plastic films, woven or nonwoven webs of natural materials (e.g., wood or cotton fibers), synthetic fibers (e.g., polyolefins, polyamides, polyester, polyethylene, or polypropylene fibers), or a combination of natural and/or synthetic fibers, stretchable nonwovens, or coated woven or nonwoven webs. The belt 40 may comprise an inner hydrophobic, nonwoven material and an outer hydrophobic, nonwoven material. The front and rear belts 84 and 86 may also comprise a plurality of elastic elements 85 disposed at least partially between the first and second belt layers 82 and 83 thereof and attached to at least one of the first and second belt layers 82 and 83 using adhesives or bonding, for example. The elastic elements 85 may comprise one or more elastic strands, elastic materials, elastomeric films, elastomeric ribbons, elastomeric nonwovens, elastomeric filaments, elastomeric adhesives, elastomeric foams, scrims, or combinations thereof.

The chassis 38 of the pant 20 may comprise a portion of the outer surface 22, a backsheet 60, a portion of the inner surface 24, a topsheet 58, and an absorbent core 62 disposed between at least a portion of the topsheet 58 and the backsheet 60. In addition, the chassis 38 may comprise elasticized barrier leg cuffs 64 disposed at or adjacent the side edges 48 of the chassis 38. The barrier leg cuffs 64 may provide improved containment of liquids and other body exudates or wastes in the crotch region 30 and may comprise a single layer of material which may be folded to form a barrier leg cuff having two layers. The barrier leg cuffs 64 may extend from the side of the chassis 38 at or adjacent the longitudinal side edge 48 toward the longitudinal central axis L1. The barrier leg cuffs 64 may be folded along the folding lines 66 back toward the longitudinal side edges 48. The front and rear belts 84 and 86 may overlap at least a portion of the chassis 38 and one or both of the front and rear belts 84 and 86 may be disposed on the outer surface 22 of the chassis 38, on the inner surface 24 of the chassis 38, or disposed intermediate various portions of the chassis 38.

A portion of, or the whole of, the chassis 38 may be made extensible to a degree greater than the inherent extensibility of the material or materials from which the chassis 38 is made, e.g., the backsheet 60. The additional extensibility may be desirable in order to allow the chassis 38 to conform to the body of a wearer during movement by the wearer and or to provide adequate body coverage. The additional extensibility may also be desirable, for example, in order to allow the user of a pant including the chassis 38 having a particular size before extension to extend the front waist region 26, the rear waist region 28, or both of the waist regions of the chassis 38 to provide additional body coverage for wearers of differing size, i.e., to tailor the pant to the individual wearer. Such extension of the waist region or regions may give the chassis 38 a generally hourglass shape, so long as the crotch region 30 is extended to a relatively lesser degree than the waist region or regions, and may impart a tailored appearance to the pant 20 when it is donned or worn. In addition, the additional extensibility may be desirable in order to minimize the cost of the pant 20. For example, an amount of material that would otherwise be sufficient only to make a relatively smaller pant lacking this extensibility may be used to make an article capable of being extended to adequately cover a wearer that is larger than the unextended smaller pant would fit.

A portion of the chassis 38, for example, a portion of the chassis 38 in one or both of the waist regions 26 and 28 may be made laterally extensible to a maximum extensibility greater than a maximum extensibility of another portion of the chassis 38 in the crotch region 30 such that a lateral extension of each of the portions to its maximum extensibility imparts an hourglass shape to the chassis 38. The portion of the chassis 38 underlying, overlying, and/or immediately adjacent one or both of the front and rear extensible belts 84 and 86 may be made laterally extensible to a maximum extensibility greater than a maximum extensibility of another portion of the chassis 38, for example the crotch region 30, such that a lateral extension of each of the portions to its maximum extensibility facilitates application of the pant 20 onto the body of a wearer by enabling the waist regions 26 and 28 to be extended to fit over the wearer's hips and in addition, opening and orienting the leg openings enabling the wearer to place the legs through the openings more effectively.

The liquid pervious topsheet 58 may be positioned adjacent the body-facing surface of the absorbent core 62 and may be joined thereto and/or to the backsheet 60 by any attachment methods known to those of skill in the art. The liquid impervious backsheet 60 may generally be that portion of the pant 20 positioned adjacent the garment-facing surface of the absorbent core 62 and may prevent, or at least inhibit, the bodily exudates and wastes absorbed and contained in the absorbent core 62 from soiling garments that may contact the outer surface 22 of the pant 20.

The topsheet 58, the backsheet 60, and the absorbent core 62 may be manufactured of any known materials. Suitable topsheet materials may comprise porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Suitable backsheet materials may include breathable materials that permit vapors to escape from the pant 20 while still preventing, or at least inhibiting, bodily exudates or wastes from passing through the backsheet 60. Such materials may include nonwoven materials, woven materials, films, and/or laminates comprising a combination of one or more of these materials. In one embodiment, the backsheet 60 may be a film and nonwoven laminate, wherein the nonwoven of the laminate forms the outer cover layer 42.

A suitable absorbent core 62 for use in the pant 20 may comprise any absorbent material which is generally compressible, conformable, non-irritating to the wearer's skin, and capable of absorbing and retaining liquids such as urine and other certain body exudates. Absorbent material may comprise a superabsorbent material, a cellulosic material, or combinations thereof. In some instances, the absorbent core may comprise one or more adhesives and a superabsorbent material and may be free of, or at least mostly free of, a cellulosic material. In addition, the configuration and construction of the absorbent core 62 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). In some forms, the absorbent core 62 may comprise a fluid acquisition component, a fluid distribution component, and/or a fluid storage component. An example of a suitable absorbent core having a fluid acquisition component, a fluid distribution component, and a fluid storage component is described in U.S. Pat. No. 6,590,136.

The outer cover layer 42 may be disposed on the outer surface 22 of the pant 20 and may cover the crotch panel 56 of the absorbent chassis 38. The outer cover layer 42 may extend into and cover the front waist panel 52 and the rear waist panel 54 of the chassis 38. The outer cover layer 42 may form a portion of the backsheet 60 and/or the chassis 38. In a form, the outer cover layer 42 may be directly joined to and cover a portion of, or all of, the liquid impervious backsheet 60 of the chassis 38. The outer cover layer 42 may be disposed between the front and rear belts 84 and 86.

The outer cover layer 42 may comprise a material separate from the first and second belt layers 82 and 83 forming the belts 84 and 86. The outer cover layer 42 may comprise two or more layers of materials of any known materials including the materials used for the first and second belt layers 82 and 83. The outer cover layer 42 may comprise a single layer of a nonwoven web of synthetic fibers. The outer cover layer 42 may comprise a single layer of hydrophobic, non-stretchable nonwoven material. In some instances, the outer cover layer 42 may comprise a film, a foam, a nonwoven, a woven material, or the like and/or combinations thereof such as a laminate of a film and a nonwoven.

The belt 40 may be at least partially formed, or fully formed, when the front and rear belts 84 and 86 are permanently or refastenably connecting together to form the seams 32. Any suitable seams may be formed, as known to those of skill in the art. The belt 40 may be ring-like and elastic. The ring-like elastic belt 40 may extend about the waist opening 36 of the pant 20 and act to dynamically create fitment forces and to distribute the forces dynamically generated during wear.

Figure 4:
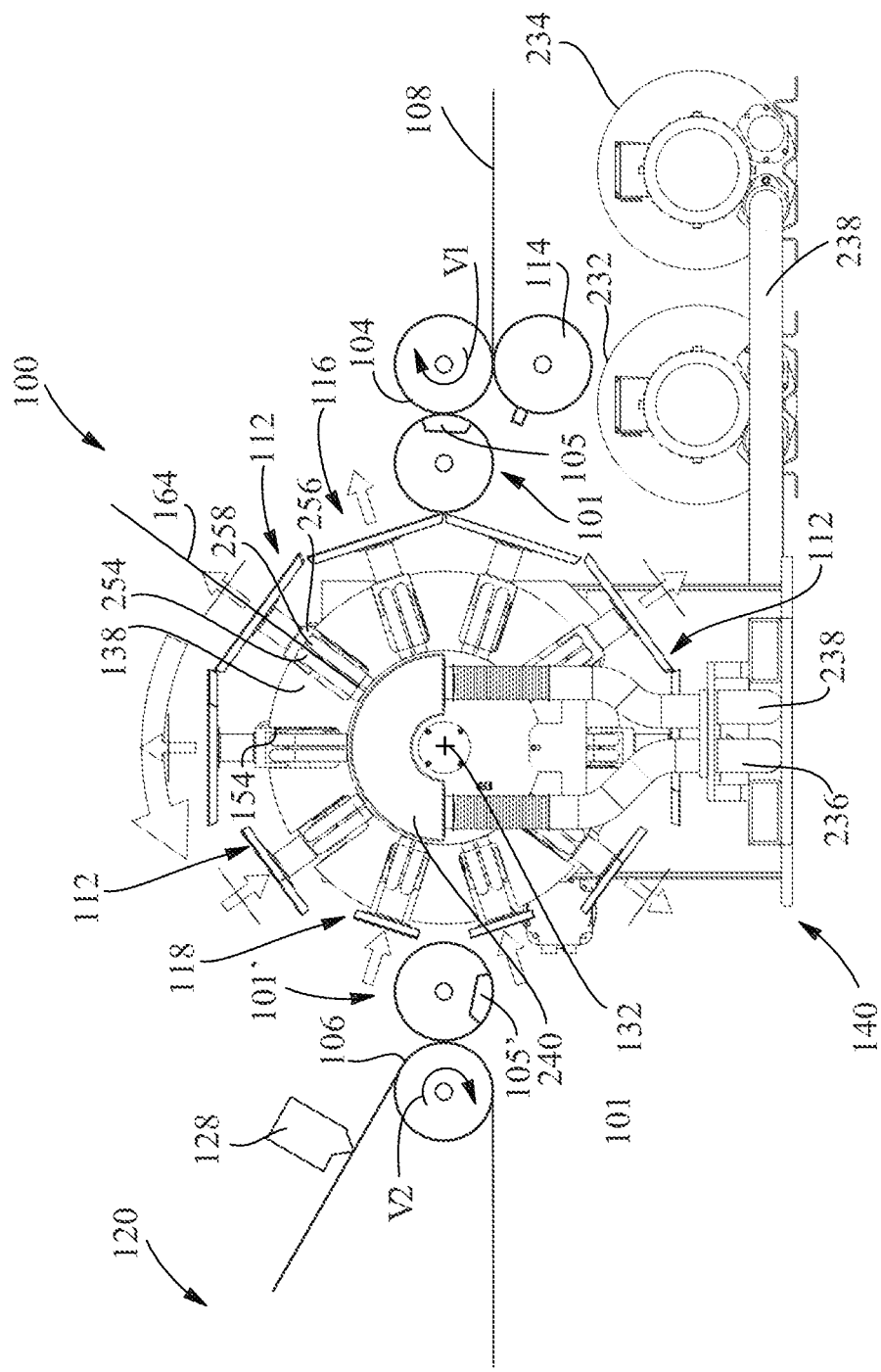
FIG. 4 is a front view of the transfer assembly and the apparatuses comprising the heads of FIG. 1 in accordance with the present disclosure.
Figure 5:
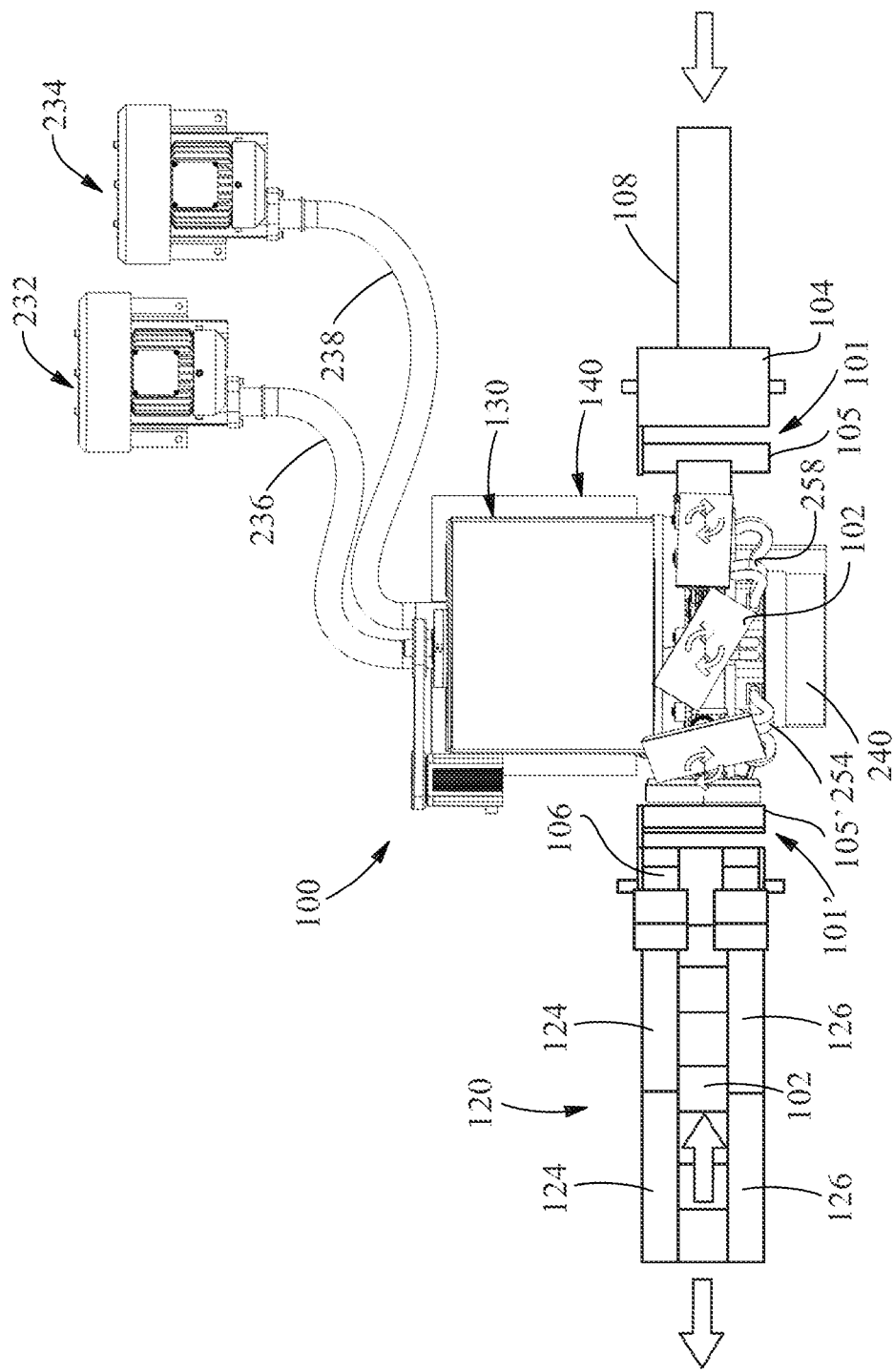
FIG. 5 is a top view of the transfer assembly and the apparatuses comprising the heads of FIG. 1 in accordance with the present disclosure.
Figure 6:
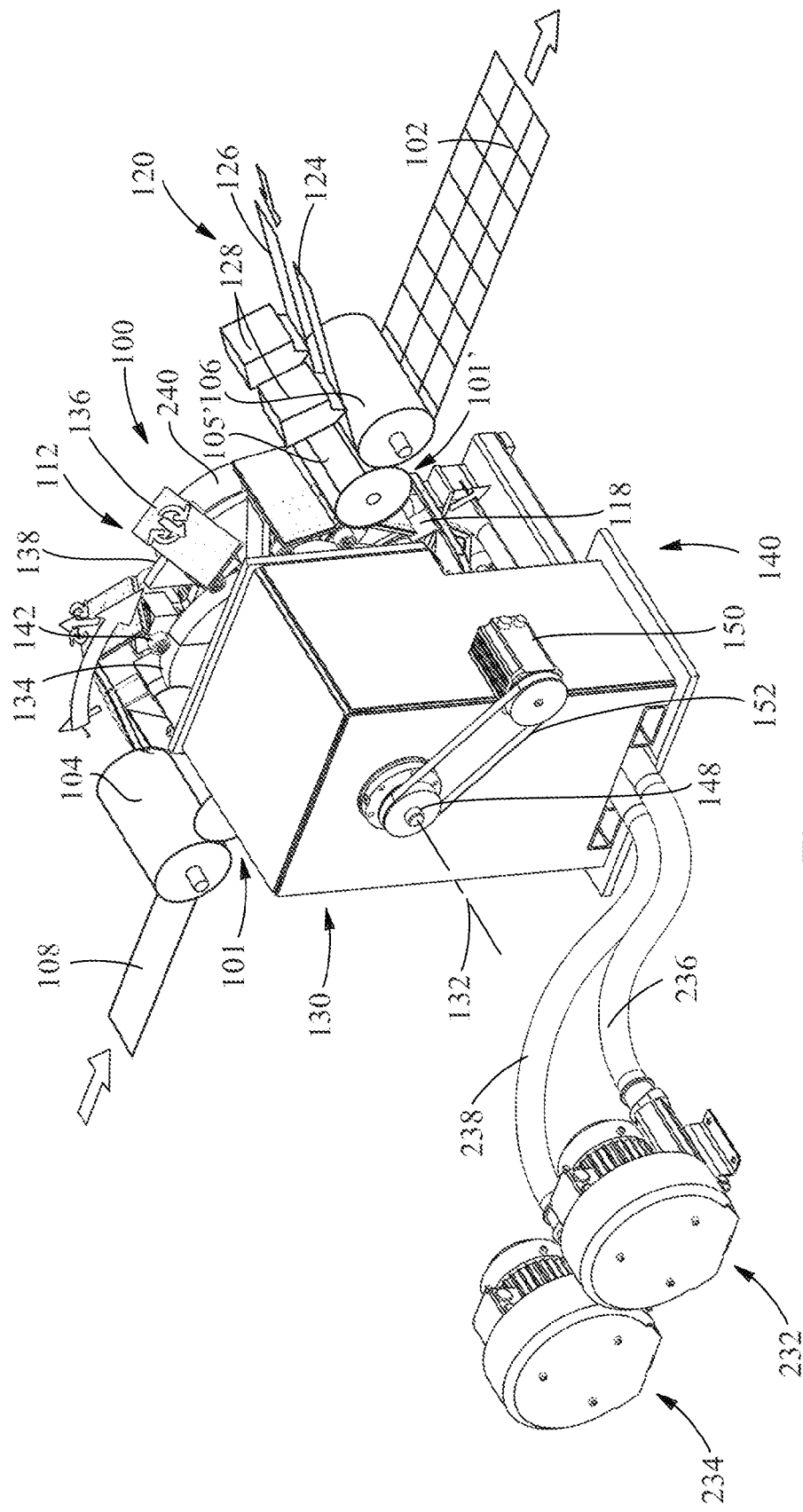
FIG. 6 is a rear perspective view of the transfer assembly and the apparatuses comprising the heads of FIG. 1 in accordance with the present disclosure.

Referring to FIGS. 1 and 4-6, an overall transfer apparatus comprising a transfer assembly 100 and at least one apparatus 101 or 101' comprising at least one head 105 or 105' is illustrated. As explained above, an apparatus may be provided on the input and output sides of the transfer assembly 100 or may only be provided on the input side or on the output side of the transfer assembly 100. An apparatus on the input side of the transfer assembly is labeled 101 and an apparatus on the output side is labeled 101' (with its various components also being numbered with primes). The apparatus 101 may be the same or different than the apparatus 101'. The differences may be in size, shape, and/or speed, for example. The overall transfer assembly is configured to transfer discrete articles from a pick-up location to a drop-off location, as explained herein. FIG. 1 is a front perspective view of the overall transfer apparatus comprising the transfer assembly 100, the apparatus 101, and the apparatus 101'. FIG. 4 is a front view of the overall transfer apparatus of FIG. 1. FIG. 5 is a top view of the overall transfer apparatus of FIG. 1. FIG. 6 is a rear perspective view of the overall transfer apparatus of FIG. 1. The overall transfer apparatus may transfer discrete articles 102 from a first moving carrier member 104 to a second moving carrier member 106. The moving carrier members 104 and 106 from and to which the discrete articles 102 may be transferred may be rolls, drums, curved conveyors, linear conveyors, and/or discrete heads following a curvilinear path, for example. The moving carrier members may be rotating carrier members, such as rolls or cylindrical rolls. The output side of the first moving carrier member 104 may represent the pick-up location and the input side of the second moving carrier member 106 may represent the drop-off location in certain instances. An apparatus 101 may be provided intermediate the transfer assembly 100 and the first moving carrier member 104, and likewise, an apparatus 101' may be provided intermediate the transfer assembly 100 and the second moving carrier member 106. The first and second moving carrier members 104 and 106 may be moving at a different surface velocity or at the same surface velocity. Surfaces of the first and second moving carrier members 104 and 106 may have different or the same tangential velocities. Typically, surfaces of the first and second moving carrier members 104 and 106 have constant, or substantially constant, tangential velocities, but the tangential velocities may also be variable in certain instances. A transfer member 112 of the transfer assembly 100 or the head 105 of the apparatus 101 (if the apparatus is provided on the input side of the transfer assembly 100) may pick up the discrete article 102 at a first velocity, V1, from the first moving carrier member 104. The transfer member 112 will then convey the discrete article 102 to the output side of the transfer assembly 100. Next, the transfer member 112 or the head 105' of the apparatus 101' (if the apparatus is provided on the output side) may apply the discrete article 102 at a second velocity, V2, to the second moving carrier member 106. The first velocity, V1, and the second velocity, V2, at the point or zone of discrete article transfer to and from the first and second moving carrier members 104 and 106 may be tangential or linear velocities.

A continuous web of articles 108 may be fed on a roll or other conveying mechanism toward the first moving carrier member 104 and, optionally, the apparatus 101. Once a portion of the web of discrete articles 108 long enough to form a discrete article 102 is engaged with the first moving carrier member 104, is engaged with a portion of a transfer member 112 of the transfer assembly 100, or optionally, is engaged with a portion of a head 105 of the apparatus 101, a knife integral to the first moving carrier member 104 may cut the web 108 into discrete articles 102 against an anvil roll 114. The knife may be a flex knife, a die cutter, a shear knife, or any other suitable knife or cutting device or mechanism. Knife and anvil roll technology is generally known in the art. In other instances, previously cut discrete articles 102 may be fed on a conveyor toward the first moving carrier member 104. In some instances, discrete articles 102 may be engaged directly with the head 105 of the apparatus 101 directly without the moving carrier member 104 and anvil roll 114 being present.

Portions of the transfer members 112 of the present disclosure may also turn between a first position 116 and at least a second position 118 when transferring the discrete articles 102 from an input side of the transfer assembly 100 to an output side of the transfer assembly 100. As a result, the discrete articles 102 may be turned between a first position 116 and a second position 118. The portions of the transfer members 112 may be turned using rotation assemblies engaged with a portion of each transfer member 112, as described in further detail below. The discrete articles 102 may be turned between about 30 degrees and about 180 degrees, between about 40 degrees and about 150 degrees, between about 60 degrees and about 120 degrees, between about 75 degrees and about 105 degrees, about 45 degrees (e.g., +/−5 degrees), about 90 degrees (e.g., +/−5 degrees), 45 degrees, 90 degrees, about 180 degrees (e.g., +/−5 degrees), or 180 degrees, specifically reciting each 0.5 degree increment within the above-recited ranges and all ranges formed therein or thereby. Optionally, the discrete articles 102 may also not be turned at all and the transfer assembly may be used for conveying and/or repitching the discrete articles 102 without turning them.

Again referring to FIGS. 1 and 4-6, continuous webs of components 120 may be moving towards, over, and away from the second moving carrier member 106 on a roller, conveyor, or other mechanism. In one example, these webs of components 120 may be front belts 124 and rear belts 126, although in other examples, the webs of components 120 may be various other components or even discrete components that have been previously cut from a continuous web. An adhesive may be applied to the webs of components 120 or discrete components using adhesive dispensers 128. The adhesive dispensers 128 are optional in some circumstances. The adhesive may be applied to portions of the webs of components 120 prior to those portions being moved over the second moving carrier member 106. As a result, a discrete article 102 being transferred to the second moving carrier member 106, by either a transfer member 112 or a head 105' of the apparatus 101', may be adhesively attached to the webs of components 120 when transferred onto the second moving carrier member 106. In one example, the discrete article 102 may be a chassis 38 and the front waist panel 52 of the chassis 38 may be adhesively attached to the continuous web of front belts 124 and the rear waist panel 54 of the chassis 38 may be adhesively attached to the continuous web of rear belts 126. This may form a web of absorbent articles. The web of absorbent articles may then be cut or separated into discrete absorbent articles, such as the absorbent article 10 of FIG. 2.

Figure 7:
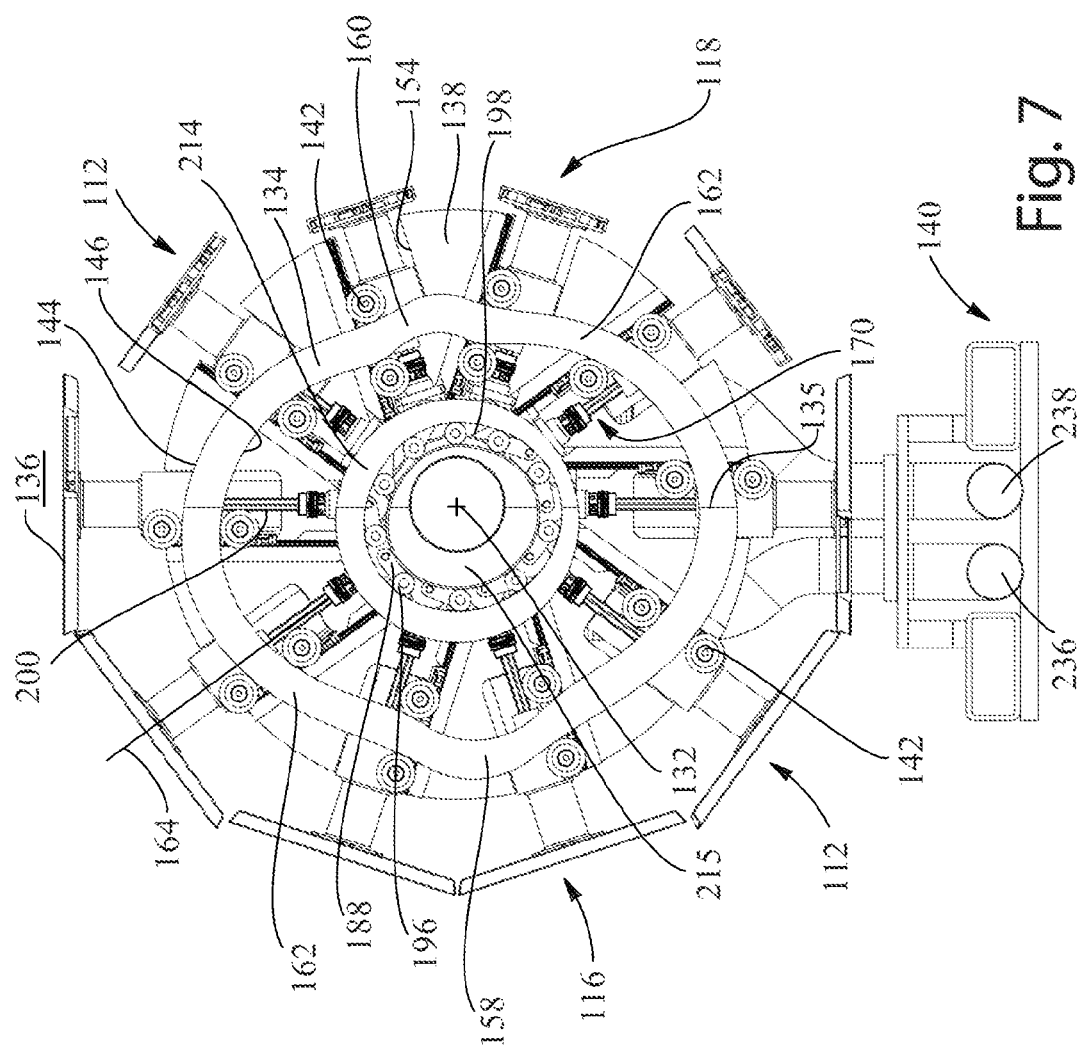
FIG. 7 is a rear view of a portion of the transfer assembly of FIG. 1 in accordance with the present disclosure.
Figure 8:
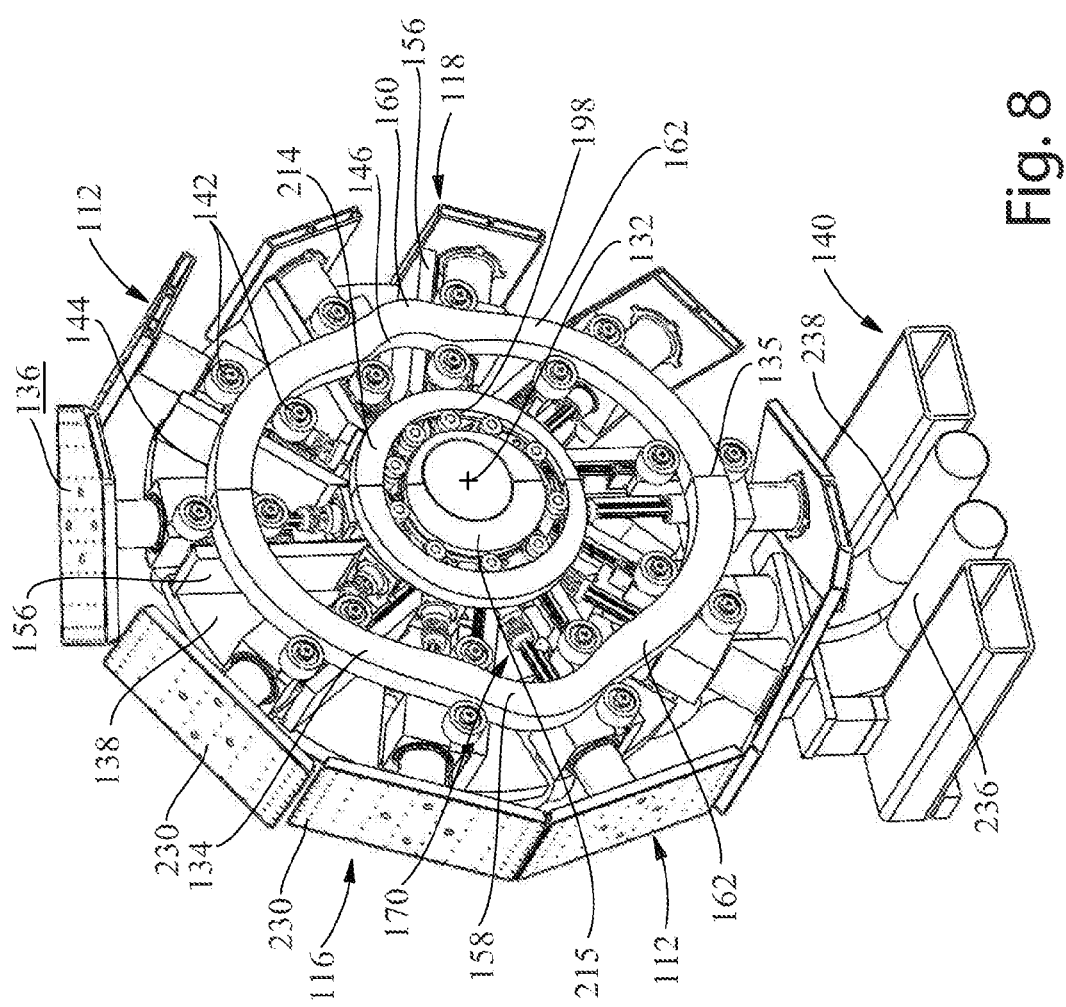
FIG. 8 is a rear perspective view of a portion of the transfer assembly of FIG. 1 in accordance with the present disclosure.
Figure 9:
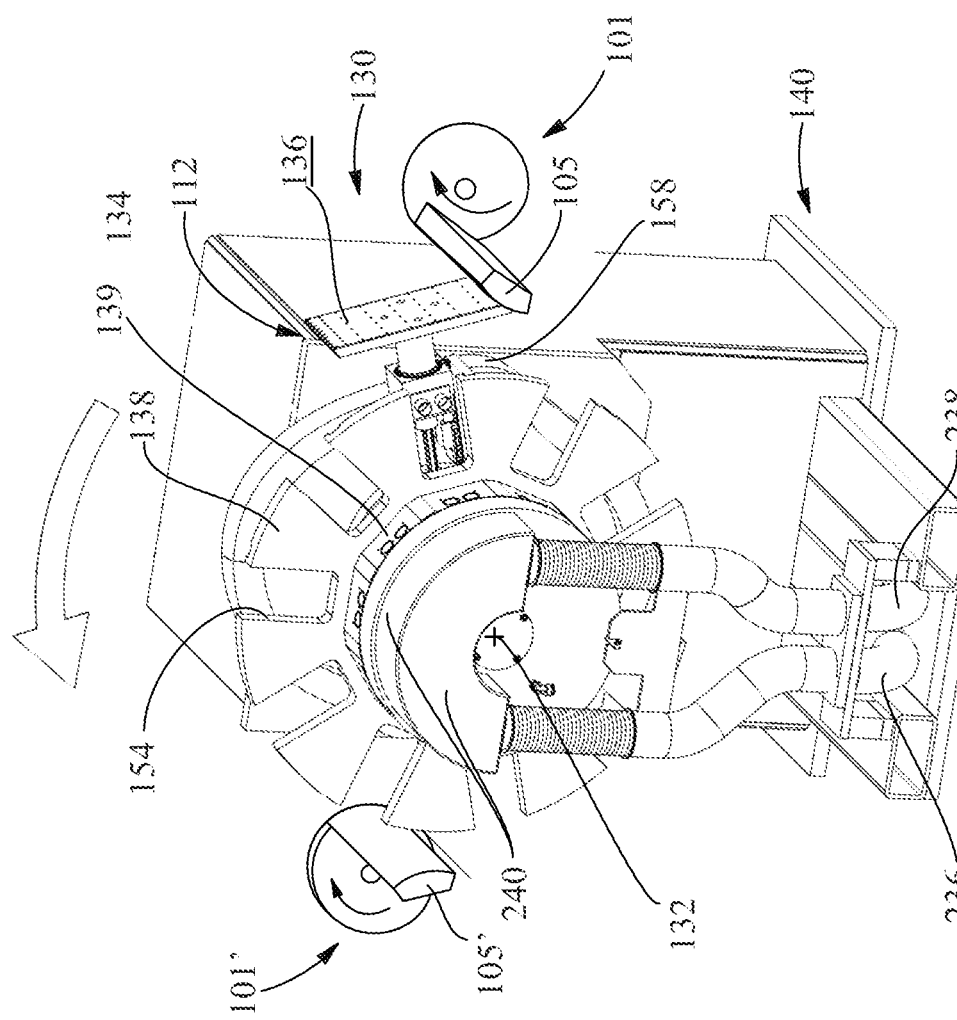
FIG. 9 is a simplified, front perspective view of a transfer assembly and portions of apparatuses comprising heads for transferring discrete articles in accordance with the present disclosure.

Referring to FIGS. 1 and 4-10, the transfer assembly 100 may comprise a frame 130 defining a rotation axis 132 and a track 134 (also referred to herein as a first track or the outer track) having a circumferential shape surrounding the rotation axis 132. FIG. 7 is a partial rear perspective cross-sectional view of the transfer assembly 100 and FIG. 8 is a partial rear perspective cross-sectional view of the transfer assembly 100. In both of FIGS. 7 and 8, the frame 130 and various other components have been removed to more clearly illustrate various features. FIG. 9 is a front perspective view of the transfer assembly 100 with multiple transfer members 112 removed for clarity in illustration. FIG. 10 is a rear view of portions of the transfer assembly 100 illustrating the track 134, the transfer member 112, and other components for clarity. The apparatuses 101 and 101' are also illustrated in FIGS. 1, 4-6, 9, and 10. The distance between the rotation axis 132 and various points on the track 134 may vary. The track 134 may be a cam track. The track 134 may comprise one or more separation points 135 in the event the track 134 needs to be disassembled for maintenance or other reasons. The transfer assembly 100 may comprise one or more transfer members 112 movably, rollably, and/or slidably engaged with the track 134. Each transfer member 112 may comprise a transfer surface 136 on an end of the transfer member 112 most distal from the rotation axis 132. The transfer surface 136 may be configured to receive one or more of the discrete articles 102. The transfer surfaces 136 of the transfer members 112 may be configured to retain the discrete articles 102 thereto using a fluid pressure, such as vacuum, magnets, or an adhesive, for example. The transfer assembly 100 may also comprise a wheel 138 supported by the frame 130 and configured to rotate about the rotation axis 132. The wheel 138 may or may not be round about its perimeter. The wheel 138 may be engaged with portions of the transfer members 112 such that as the wheel 138 rotates about the rotation axis 132, the transfer members 112 circumnavigate about a path about the rotation axis 132 in correspondence with the track 134. The shape of the track 134 may cause the transfer members 112 to move radially inwardly and radially outwardly relative to the rotation axis 132 while the transfer surfaces 136 are maintained a constant or a substantially constant distance or minimum distance away from the first and second moving carrier members 104 and 106 or surfaces of the heads 105 and 105' of the apparatuses 101 and 101' at the point or zone of discrete article transfer onto and off of the transfer surfaces 136. The substantially constant minimum distance or minimum distance may vary typically from 0-6 mm or may have a tolerance of typically +/−0.1 to 1 mm, although a wide range of targets are achievable. In an instance, the minimum distance may be constant, then not constant, then constant again at the point or zone of discrete article transfer as the transfer surface 136 is moved past the point or zone of discrete article transfer. Such a profile may be employed if, for instance, it is desired to only maintain the substantially constant gap at the leading and/or trailing edge of the discrete article transfer. The profile may also be adjusted to account for thickness variations in the discrete article being transferred. In some cases, the gap or minimum distance may be profiled to be larger in the region with the absorbent core, for example.

Referring again to FIGS. 1 and 4-10, the frame 130 may be mounted to a base or stand 140 for the transfer assembly 100. The apparatuses 101 and 101' may also be mounted to a base or stand. The track 134 may be formed with or in the frame 130 or be mounted to the frame 130. The track 134 may be a projection that extends from a plane of the frame 130 or may be a groove (not illustrated) defined in the frame 130. The track 134 may have a constant, or substantially constant, width, or a varying width, regardless of whether it is a projection or a groove. In the event the track 134 is a groove, a follower member 142 extending from each of the one or more transfer members 112 may be movably, slidably, and/or rollably engaged with the groove. The follower member 142 may be biased toward the track 134. In the event the track 134 is a projection as illustrated, a follower member 142 extending from each of the one or more transfer members 112, or portions thereof, may be movably, slidably, and/or rollably engaged with a surface of the projection that extends generally perpendicular to a front planer surface of the frame 130 from which the projection extends. In an instance, when the track 134 is a projection, two or more follower members 142 may extend from each transfer member 112, or portions thereof, such that one follower member 142 engages a first surface 144 of the projection and another follower member 142 engages the opposite surface 146 of the projection. The follower members 142 may be rollers or cam followers that slide or roll about the track 134 as the transfer member 112 circumnavigates about a path around the rotation axis 132. The follower members 142 may comprise materials such as metals, plastics, and/or polymers, for example, or coatings thereof, to permit rolling or sliding movement between the follower members 142 and the track 134.

In the event that the track 134 is a groove, the follower members 142 may comprise two stacked concentric cylindrical cam followers, each following one side of the groove. This may constrain the cam followers to rotate in one direction and eliminate, or at least inhibit, the issue of cam follower reversal as with a single cam follower following a groove. The stacked cam followers may also be configured with eccentricity between the axes of their rotation. Adjusting the eccentric may adjust the clearance between the cam groove and the cam followers. An elastic element, such as a spring or pneumatic cylinder, for example, may also be used to keep the cam follower loaded against one surface of the groove. This has the potential to only use one surface of the groove.

In the event that the track 134 is a projection, the follower members 142 may comprise two conjugate cylindrical follower members on each side of the track projection 134. This arrangement may naturally cause each follower member to rotate in one direction. The axis of rotation of one of the follower members may be adjusted to control the clearance between the follower members and the track projection 134. A single follower member may be employed in conjunction with an elastic or inertial force to keep the follower member in contact with the track projection 134. The follower member may be spring loaded or loaded by pneumatic cylinder, for example.

Figure 16:
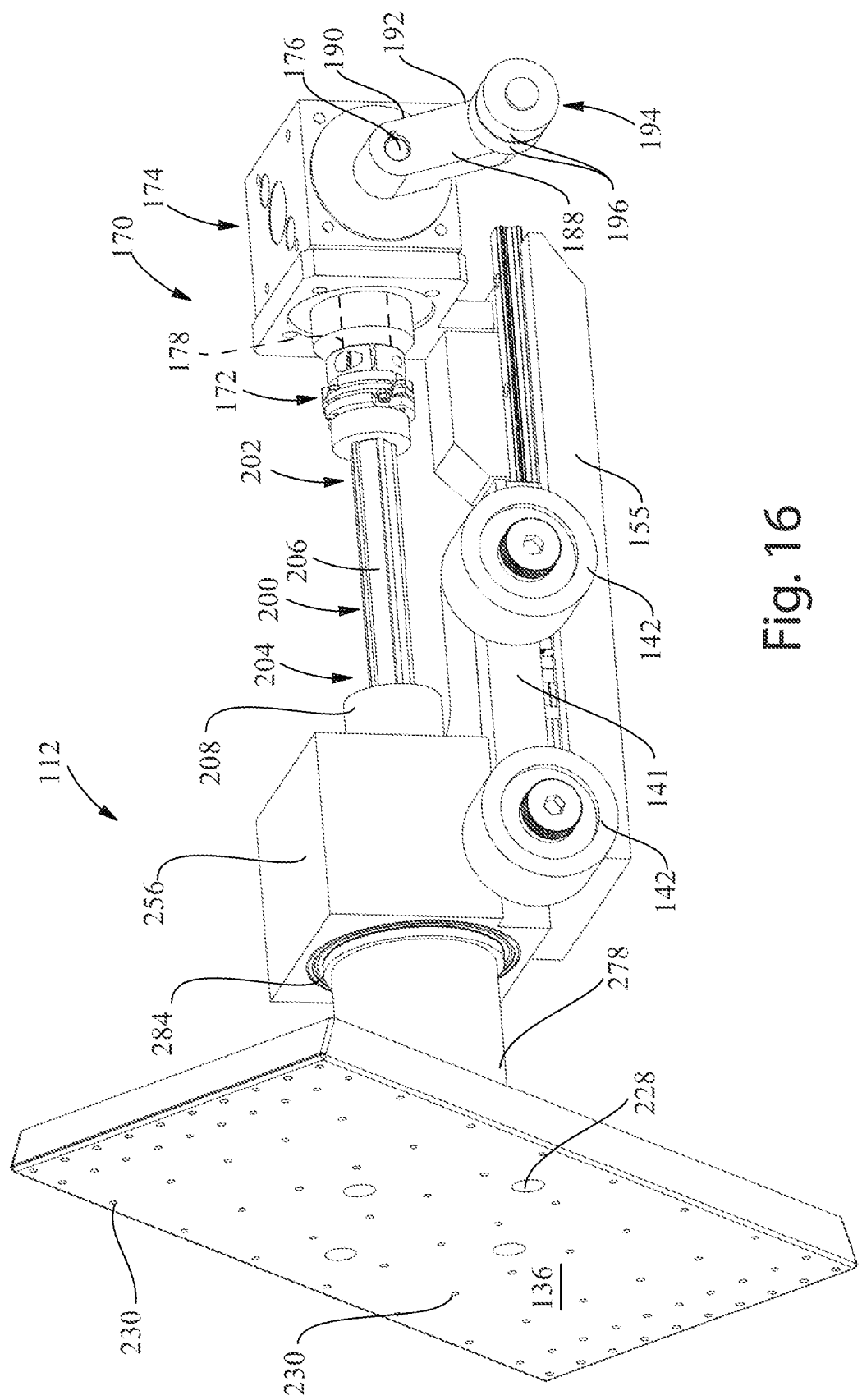
FIGS. 16-18 are perspective views of a transfer member engaged with a rotation assembly in accordance with the present disclosure.
Figure 17:
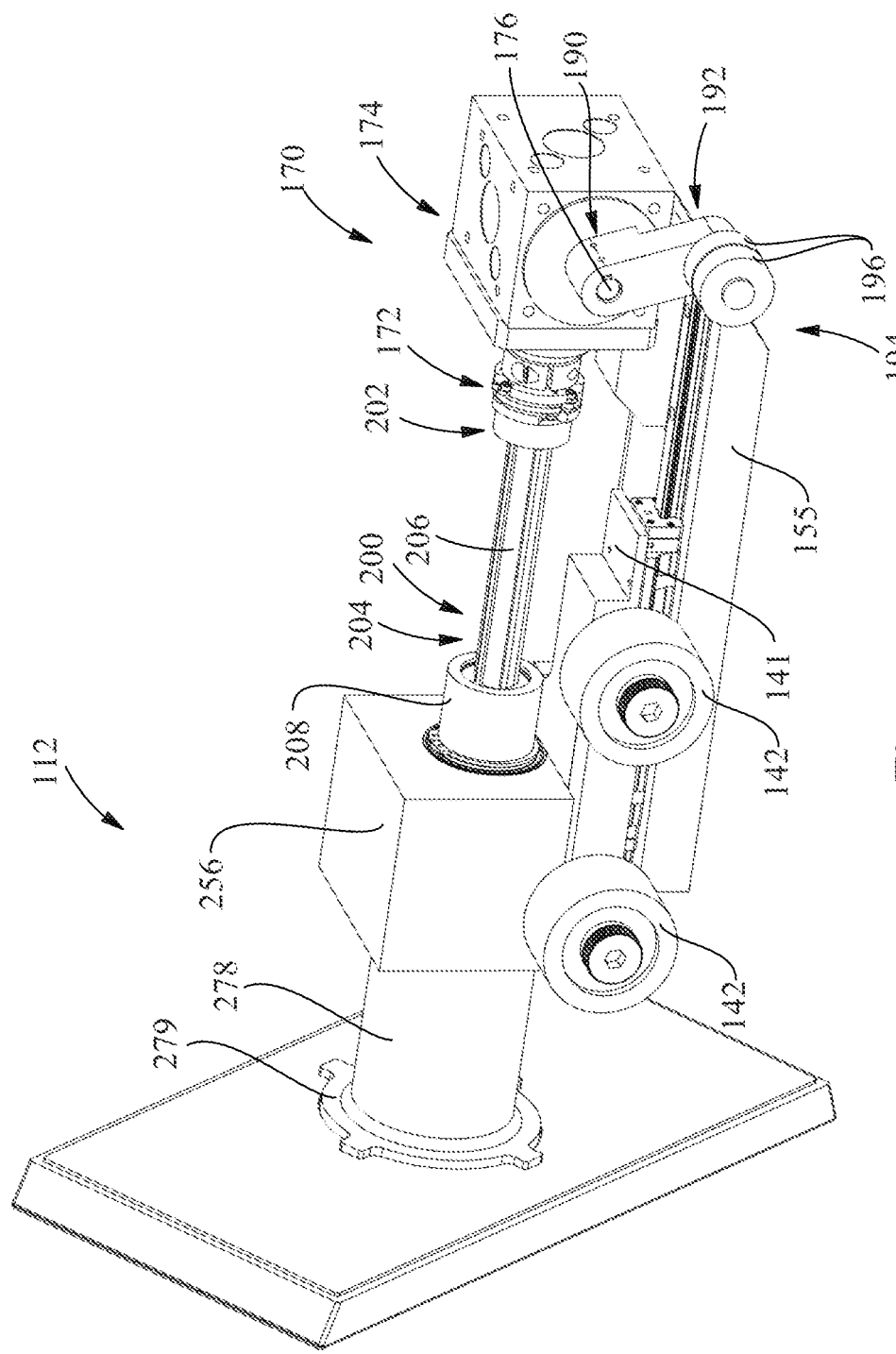
Figure 18:
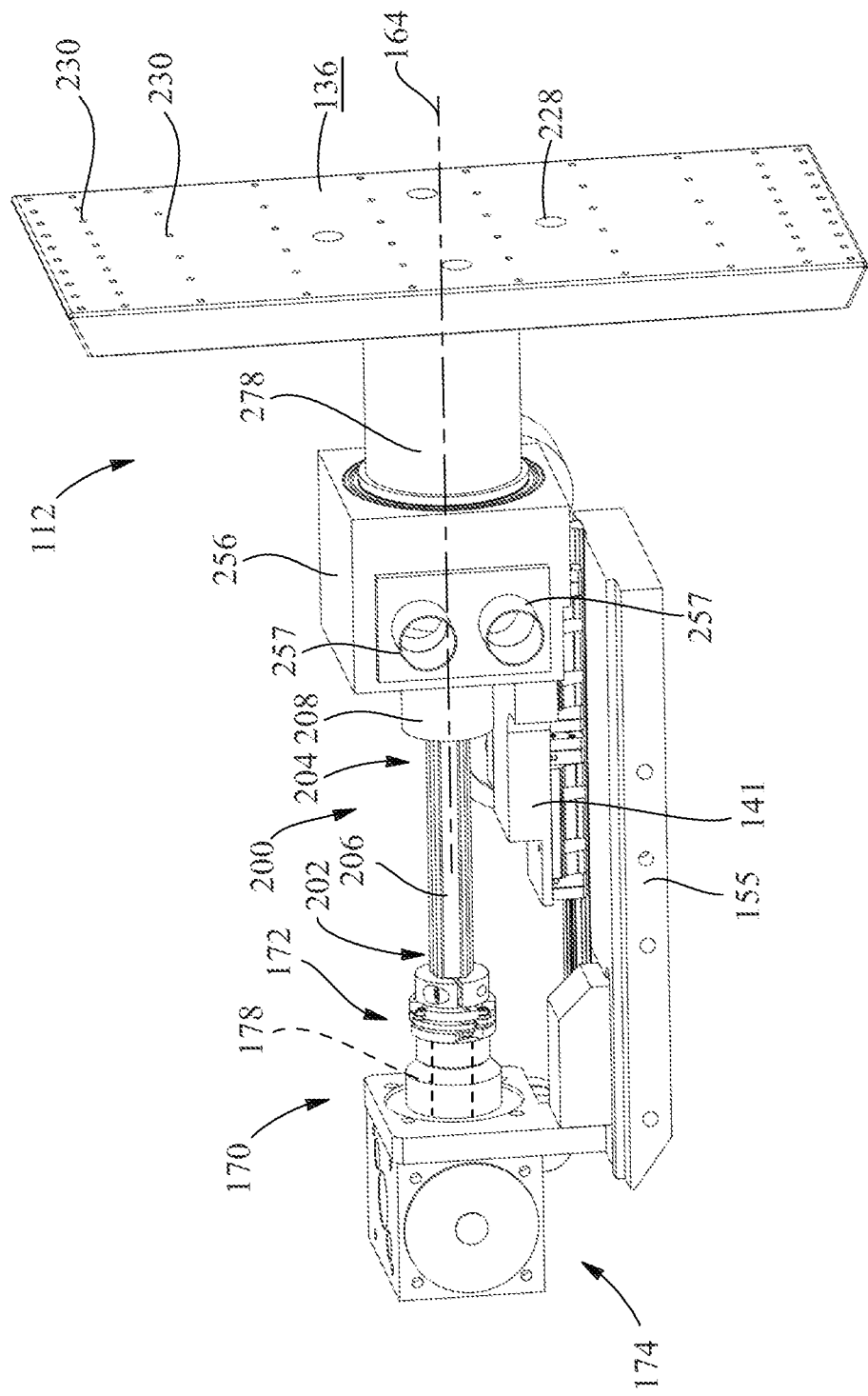

Referring to FIGS. 16-18 for clarity, the transfer members 112 may comprise a fluid manifold attached to or formed with a base 141 and the follower members 142 may be mounted, or rotatably mounted, to the base 141. The base 141 may be slidably or movably engaged with a plate 155 such that the transfer members 112 may be moved radially relative to the wheel 138 and the plate 155 by the track 134. The plate 155 may be used to mount portions of the transfer members 112 and portions of the rotation assembly (as described below) to projections 156 on the wheel 138, as described in further detail herein.

Referring to FIGS. 1 and 4-10, the wheel 138 may be engaged with the frame 130 such that the wheel 138 is permitted to rotate relative to the frame 130 about the rotation axis 132. The frame 130 may locate bearings that support the drive shaft 148 and/or the wheel 138. This permits rotation of wheel 138 and the drive shaft 148 about the first rotation axis 132. This also locates the axial position of the wheel 138 and the drive shaft 148. The first rotation axis 132 may be located generally centrally, although not necessarily at the midpoint of the track 134, within the circumference of the track 134. A drive shaft 148 that has a rotation axis common to the rotation axis 132 may be driven by one or more actuators 150 through the use of a drive belt or chain 152, for example. The drive shaft 148 may be engaged with the wheel 138 to cause the wheel 138 to rotate. Other methods of rotating the drive shaft 148 will be envisioned by those of skill in the art and will not be discussed in detail for brevity. The one or more actuators 150 may cause the drive shaft 148 to rotate in either the clockwise or counter-clockwise direction. The drive shaft 148 may rotate in either direction and at any speed about the rotation axis 132 to drive or rotate the wheel 138. The wheel 138 may rotate in a direction generally parallel with the plane of the frame 130 from which the track 134 extends or is defined in. The wheel 138 may be fixedly attached to the drive shaft 148 such that upon activation of the one or more actuators 150, the drive shaft 148 and, thereby, the wheel 138 may rotate.

The wheel 138 may have one or more recesses 154 defined in a perimeter thereof. Fluid conduits and/or other components may extend through the recesses 154 to portions of the transfer members 112. Also, by providing the recesses 154 in the wheel 138, the wheel 138 may be lighter and have less rotational inertia.

Referring again to FIGS. 1 and 4-10, the wheel 138 may be engaged with one or more of the transfer members 112 through the use of the plate 155. The wheel 138 may have projections 156 extending therefrom in a direction toward the frame 130. Portions of the plate 155 extending intermediate a portion of the transfer member 112 and a torque transmitting assembly (as discussed below), for example, may be mounted to the projections 156 on the wheel 138 to provide support to the rotating assembly which includes the transfer member 112. The plate 155 may be movably engaged with the base 141 as described in greater detail herein. Portions of the transfer members 112 may also be engaged with shafts or shaft assemblies comprising a spline, for example, to allow the transfer members 112 to be movable in radial directions relative to the first rotation axis 132. The shaft or shaft assemblies may also allow portions of the transfer members 112 to be turned relative to the wheel 138 about a second rotation axis 164 that may be positioned generally perpendicular, or transverse, to first rotation axis 132. The shaft or shaft assemblies and the transfer members 112 may rotate with the wheel 138. Transfer members 112 may have a constant relative angular position about the first rotation axis 132 and may share the same angular velocity about the first rotation axis 132. Stated another way, the transfer members 112 may orbit about the rotation axis 132 at a constant angular velocity or a substantially constant angular velocity.

The wheel 138 may be engaged with one to sixteen or more transfer members 112, for example. All or some of the transfer members 112 may be used to transfer discrete articles 102 in various manufacturing operations. In some instances, every other, or every third, transfer member 112 may be used to transfer discrete articles 102 in a particular manufacturing operation, for example.

Referring to FIGS. 7, 8, 10, and 16, the one or more follower members 142 may extend from the base 141 or other portion of the transfer members 112 such that they may engage the track 134 and move the transfer members 112 radially. The follower members 142 may be attached to portions of the transfer members 112 or may be formed with the transfer members 112. The "transfer members 112" may refer to not only the portion comprising the transfer surface 136 but all of the radially movable assembly at the second end 204 of the shaft or shaft assembly 200. Radially moving assemblies comprise the fluid manifold, the spline receiving member, the base 141, the follower members 142, the housing, and the transfer surface 136, for example. Some of these components are discussed in more detail below. The shaft, the spline, and the second end of the shaft (as are all discussed below) may not be radially moving. In certain instances, more than two follower members 142 may be desired on a particular track 134 or if more than one track 134 is provided on the frame 130. In an example, two tracks (not illustrated) for the follower members 142 may be provided on a frame and one or more follower members may be movably engaged with each of the tracks. The follower members 142 being movably engaged with the track 134 causes the transfer members 112 to circumnavigate about a path about the rotation axis 132 in correspondence with the track 134.

The shape of the track 134 may be such that it causes the follower members 142 and, thereby, the transfer members 112, and the transfer surfaces 136 of the transfer members 112, to be moved radially inwardly and outwardly when the transfer members 112 are rotating about the path of the rotation axis 132 in correspondence with the track 134. This path can be seen in FIGS. 7, 8, and 10, for example. The path may be said to be about the rotation axis 132. The track 134 may comprise a first projection 158 extending radially outwardly from the rotation axis 132 proximate to the first moving carrier member 104 and a second projection 160 extending radially outwardly from the rotation axis 132 proximate to the second carrier member 106. This radial extension of the projections 158 and 160 is discussed with reference to a non-projection portion 162 of the track 134. The projections 158 and 160 may have any suitable shape which generally extends radially outwardly from the rotation axis 132. The shape of the projections 158 and 160, among other things, may dictate the tangential velocity of a portion of the transfer surface 136 at the point or zone of discrete article transfer from or to one of the moving carrier members 104 and 106 or from or to one of the heads 105 and 105' of the apparatuses 101 and 101'. The shape of the projections 158 and 160 may also contribute to or cause the gap between the transfer surfaces 136 and surfaces of the first and second moving carrier members 104 and 106 or the surfaces of the heads 105 and 105' of the apparatuses 101 and 101' to remain constant or substantially constant at the point or zone of discrete article transfer. These projections 158 and 160 may be positioned at any locations on the track 134 that are proximate to an incoming first moving carrier member 104 or incoming head 105 or an outgoing moving second carrier member 106 or an outgoing head 105'. The track 134 may only have one projection 158 or 160 positioned proximate to one of the moving carrier members 104 and 106 or one of the heads 105 and 105'. The first projection 158 may be generally across the track 134 from the second projection 160 or otherwise situated relative to the second projection 160 depending on the positioning of the incoming first moving carrier member 104 or incoming head 105 and the outgoing second moving carrier member 106 or the outgoing head 105'. The radius of the track 134 relative to the rotation axis 132 may increase and decrease about the track 134, even in the non-projection portions 162 of the track 134. In an instance, the radius of the track 134 may increase at least when portions of the transfer members 112 are partially rotated between the first position 116 and the second position 118 to allow two adjacently positioned transfer surfaces of the transfer members 112 to clear each other (i.e., not contact each other) during rotation of the transfer members 112 about the second rotation axis 164. The increased radius of the track 134 at these locations forces the transfer members 112 radially outwardly relative to the rotation axis 132, thereby providing adequate clearance of a first transfer surface 136 and an adjacent second transfer surface 136 to rotate between the first position 116 and the second position 118. The second rotation axis 164 may be perpendicular, substantially perpendicular, or transverse to the rotation axis 132. In other instances, the rotation axis 132 may extend in a first direction and the second rotation axis 164 may extend in a second, different direction. The second, different direction may be parallel or substantially parallel (e.g., +/−0.5 to fifteen degrees) to a plane of the frame 130 from which the rotation axis 132 extends, wherein the plane extends generally perpendicular to the rotation axis 132. The rotation of the portions of the transfer members 112 and an example rotation assembly configured to accomplish this rotation will be discussed in further detail below.

The track 134 may not increase the radial distance of the transfer members 112 from the rotation axis 132 during movement of the transfer surfaces 136 between a first position and a second position. In such an instance, the transfer surfaces 136 may be shaped (e.g., ovate, round) or spaced such that they can be turned between the first position and the second position without contacting each other.

Referring to FIGS. 1 and 4-12, the transfer members 112 may each comprise the transfer surface 136 on the distal most portion thereof relative to the rotation axis 132, as referenced above. The transfer surface 136 may be flat, substantially flat, or may comprise one or more flat portions in one or more directions. FIG. 11 illustrates the flat, or substantially flat, transfer surface in a first direction, while FIG. 12 illustrates the flat, or substantially flat, surface in a second direction. Substantially flat, as used herein, means the transfer surface 136 used to support and transport a discrete article 102 conforms to a plane within about 0-10 mm, and alternatively about 0-5 mm, not including fluid ports and bolt holes, as discussed below. Example transfer surfaces 136 are illustrated as rectangular, but it is to be understood that other transfer surfaces for use with the transfer members 112 of the present disclosure may be formed of other suitable shapes, such as squares, circles, or ovals, for example. A portion of each transfer surface 136 may be flat, or substantially flat, while other portions may be arcuate. Although not illustrated, some of the transfer surfaces of the transfer members of a transfer assembly may be flat, or substantially flat, while other transfer surfaces may be arcuate. The portions of the transfer members 112 supporting the transfer surfaces 136 (e.g., the portions attached to the distal end of the housing 278 as described below) may be flat, substantially flat, or arcuate. In some instances, the transfer members 112 may be arcuate in one or more directions.

By providing flat, or substantially flat, transfer surfaces 136, a significant advantage may be achieved in that the flatness of the transfer surfaces 136 is the same, or substantially the same, whether the transfer surface 136 is in the first position 116 or rotated into the second position 118 about the second rotation axis 164. In an instance, a transfer surface 136 may have a flat, or substantially flat leading portion, an arcuate middle portion, and a flat, or substantially flat, trailing portion. This geometry of a transfer surface 136 may be employed for substantially constant gap transfer at the leading and trailing portions (and not the middle portion), for example. On related art transfer assemblies, having arcuate transfer surfaces with the arc extending generally in the longitudinal direction of the transfer surface, once the transfer member is rotated into the second position (a position which is generally 90 degrees from the first position), transfer of the discrete articles may become an issue because of the arc being in the wrong direction for transfer to a second moving carrier member 106 or a head 105' of the apparatus 101'. Stated another way, if the arc is suitable for picking up a discrete article from a first moving carrier member 104 or a head 105 of the apparatus 101, it generally may not be suitable for dropping off a discrete article onto a second moving carrier member 106 or the head 105' of the apparatus 101' because the outer edges of the transfer surface may be more distal from the second moving carrier member 106 or the head 105' of the apparatus 101', potentially leading to inefficient transfers. The flat, or substantially flat, transfer surface 136 solves that problem by providing the same, or substantially the same, distance or gap between all or most portions of the transfer surface 136 and the second moving carrier member 106 or heads 105' after the transfer surface 136 is rotated from the first position 116 into the second position 118 about the second rotation axis 164. This can lead to improved discrete article transfers and increased speed of the transfers.

One problem that may arise, however, in related art transfer assemblies using flat, or substantially flat, transfer surfaces that do not have the ability to move their transfer members radially inwardly and radially outwardly with respect to the rotation axis of the transfer assemblies, may be that there will be a significant gap at the point of discrete article transfer while portions of the flat, or substantially flat, transfer surface pass through the discrete article transfer point or transfer zone. In such an instance, the leading edges and trailing edges of the flat transfer surface may be positioned quite close to the moving carrier member or head, while the middle portion of the transfer surface, owing to its flat, or substantially flat, configuration, may be positioned more distal from the moving carrier member or heads. This gap between the middle portion of the flat, or substantially flat, transfer member and a moving carrier member or head and/or gap variation may result in poor or unacceptable transfers, especially during high speed transfers, which are desired in absorbent article manufacturing. The poor transfer may result in folding of portions of the discrete article over itself, for example.

Figure 10B:
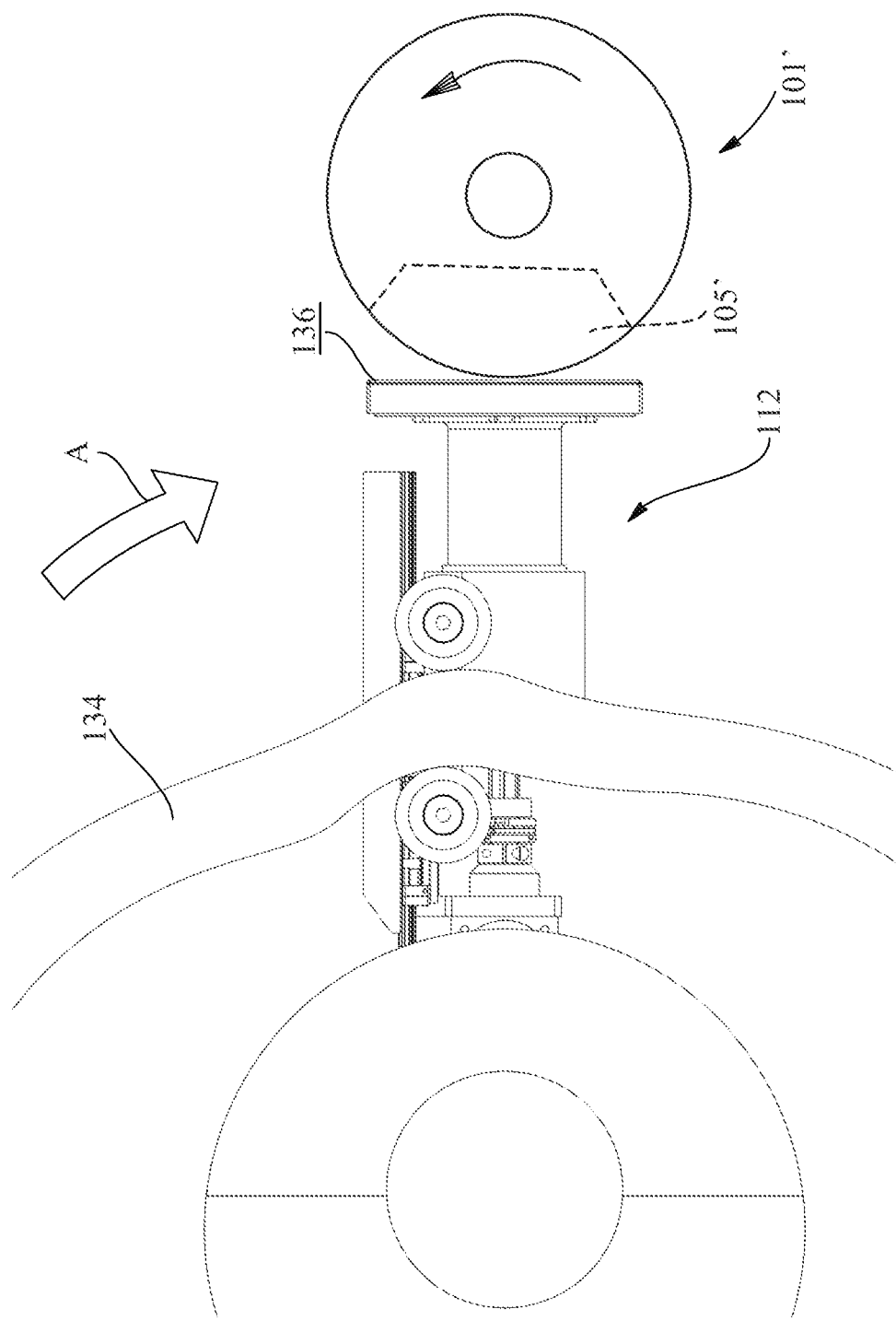
Figure 13:
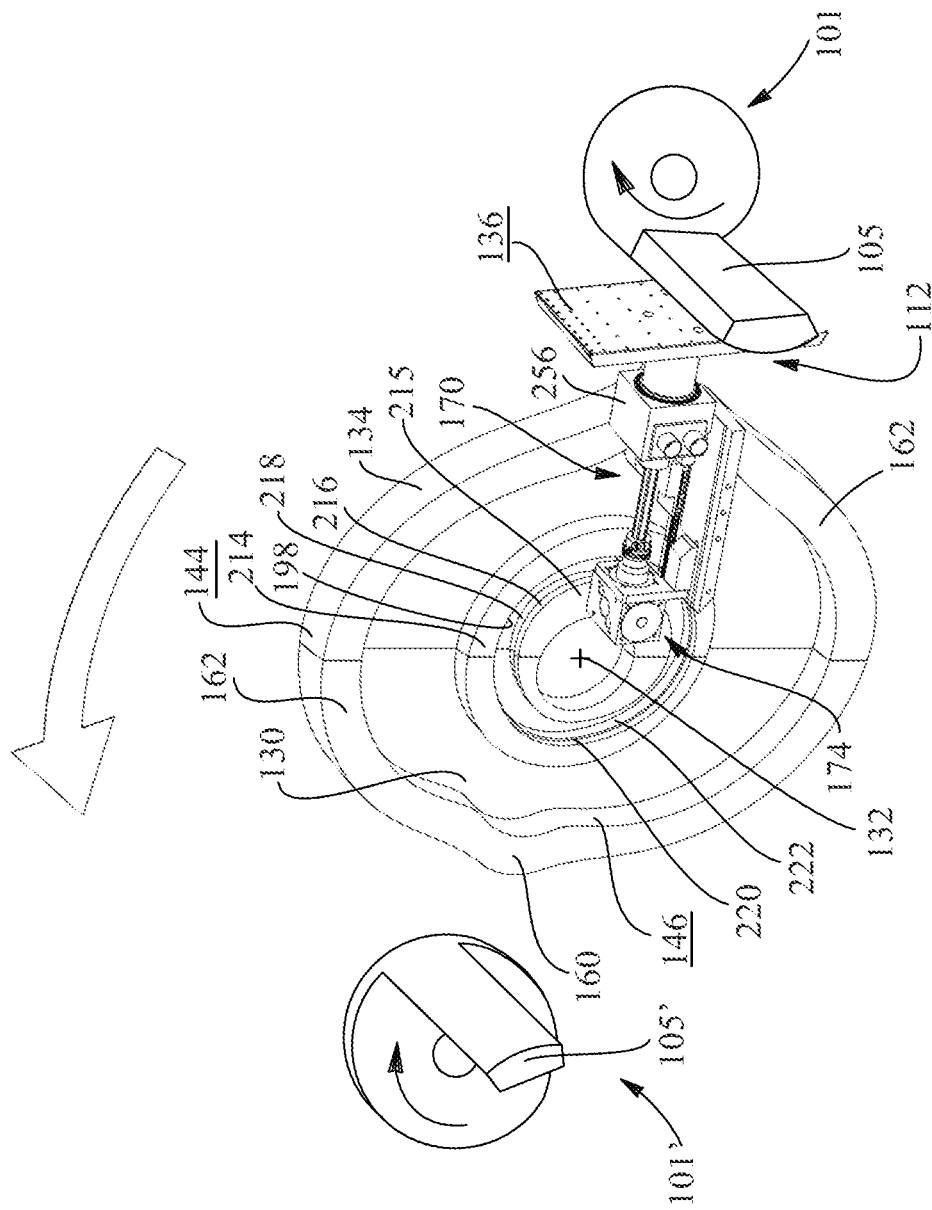
FIG. 13 is a front perspective view of two tracks, a rotation assembly, the apparatuses comprising heads, and a transfer member in a pick-up zone, with a transfer surface in a first position, in accordance with the present disclosure.
Figure 13B:
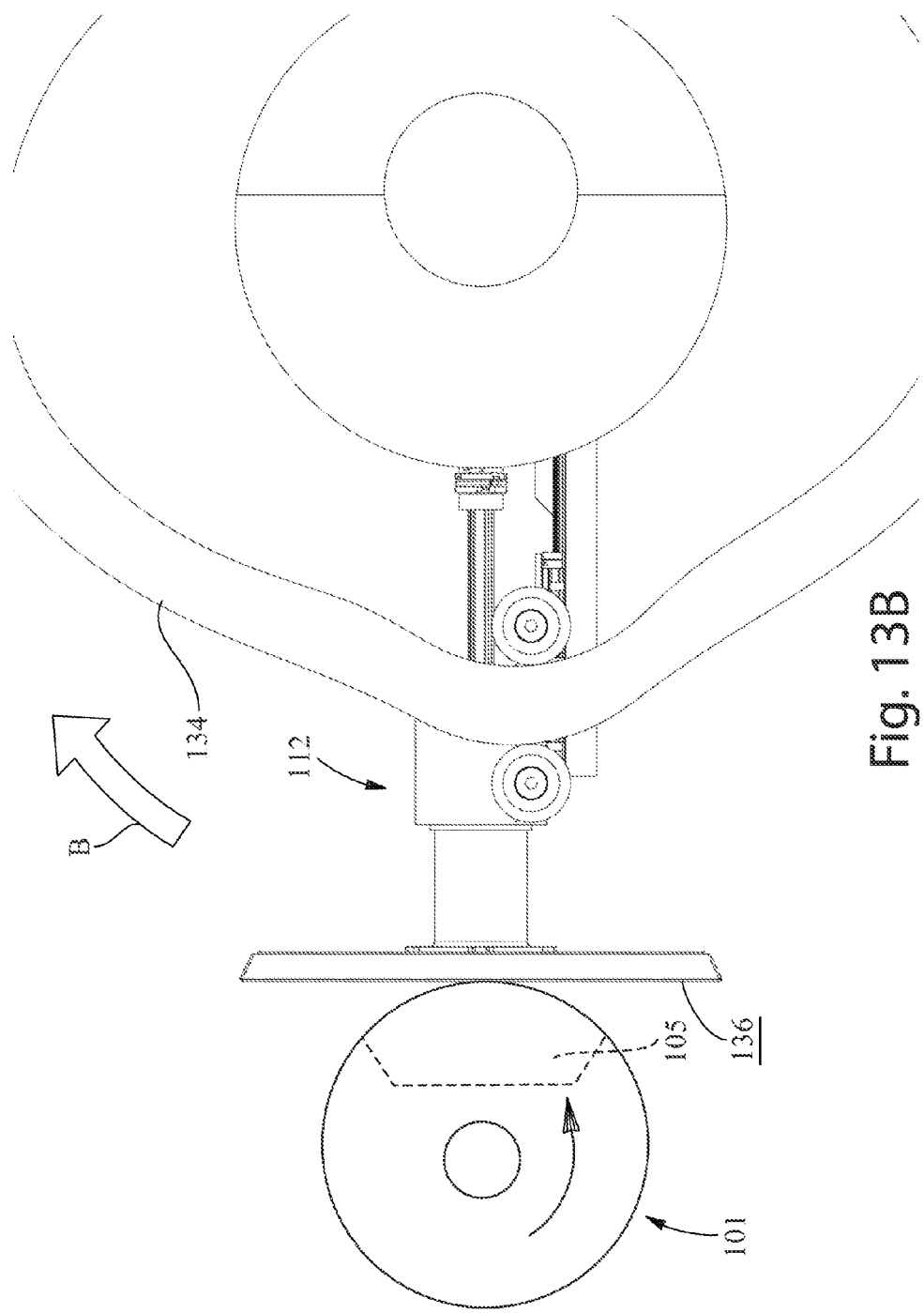
Figure 13C:
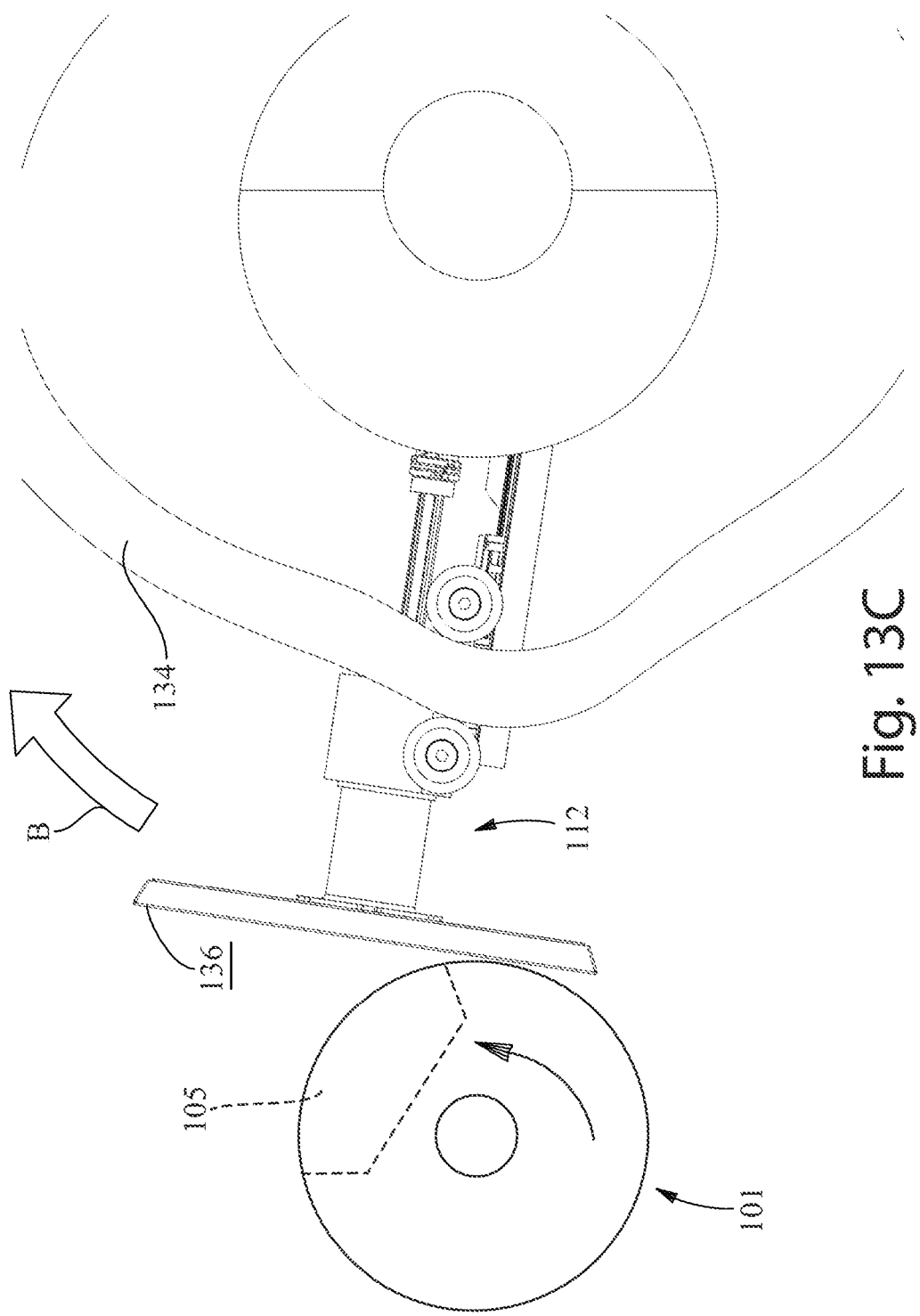

Referring to FIGS. 7, 8, and 10C, the transfer assembly 100 solves this gap problem, among others, in the middle portion of a related art transfer surface by providing the track 134 with the projections 158 and 160 therein at or proximate to the moving carrier members 104 and 106 or the heads 105 and 105'. By providing the projections 158 and 160, the transfer surfaces 136 of the transfer members 112 of the present disclosure may maintain a constant, or substantially constant (e.g., 0.1-2 mm or 0.1-3 mm), distance or minimum distance between themselves and the moving carrier members 104 and 106 or the heads 105 and 105' at the point or zone of discrete article transfer. FIGS. 10A-10C illustrate the progression of the transfer surface 136 when moving past the head 105' in the direction of arrow A. FIGS. 13A-13C illustrate the progression of the transfer surface 136 when moving past the head 105 in the direction of arrow B. Similar constant, or substantially constant, distances or minimum distances, as illustrated in FIGS. 10A-10C and 13A-13, would also apply to moving carrier members 104 and 106 if an apparatus 101 or 101' was not provided on the input or output sides of the transfer assembly 100 and the discrete articles were transferred directly from a moving carrier member 104 or 106 to the transfer member 112. In some forms, the distance may be constant, or substantially constant, then not constant, and then constant, or substantially constant again at the point or zone of discrete article transfers as the transfer surface 136 moves past one of the moving carrier members or one of the heads. The point or zone of discrete article transfer may be the point or zone at which a portion of the discrete article 102 leaves the first moving carrier member 104 or head 105 and transfers to the transfer surface 136. The point or zone of discrete article transfer may also be the point or zone at which a portion of the discrete article 102 leaves the transfer surface 136 and transfers to the second moving carrier member 106 or head 105'. The point or zone of discrete article transfer may also be where the moving carrier members, heads, and/or transfer surfaces are closest to each other in their respective rotations. Since the transfer surfaces 136 of the present disclosure are flat, or substantially flat, the transfer surfaces 136 generally may need to be moved radially outwardly and radially inwardly as portions of the transfer surfaces 136 pass through the discrete article transfer point or zone with the moving carrier members 104 and 106 or the heads 105 and 105'. The projections 158 and 160 constrain such radial movement of the transfer members 112 since the transfer members 112 are movably engaged with the track 134 and rotate about a path about the rotation axis 132 in correspondence with the track 134. As such, each of the transfer members 112 and, thereby, the transfer surfaces 136 may be moved or cammed consistently or variably radially outwardly relative to the rotation axis 132 from when, or about when, the leading edge of the transfer surface 136 is at or proximate to the point or zone of discrete article transfer until when, or about when, a midpoint or mid portion (in the machine direction of travel) of the transfer surface 136 is at or proximate to the point or zone of discrete article transfer. At such a time, the transfer surface 136 may then be moved or cammed consistently or variably radially inwardly until the trailing edge of the transfer surface 136 is at or past the point or zone of discrete article transfer or until the transfer member 112 has travelled over the projection 158 or 160 and back onto a non-projection portion 162 of the track 134.

In various forms, the angular velocity of the rotation about the first rotation axis 132 of the transfer members 112 may be or is constant, or substantially constant, in that the rotation of the drive shaft 148 and the wheel 138 may be constant. That being said, the tangential velocity of the transfer surfaces 136 changes when the transfer members 112 are moved radially outwardly and inwardly. Generally, if the transfer members 112 are moved radially outwardly, the tangential velocity of transfer surfaces 136 will increase, while if the transfer members 112 are moved radially inwardly, the tangential velocity of the transfer surfaces 136 will decrease owing to the transfer members 112 being rotated about the rotation axis 132. The tangential velocity of the transfer surfaces 136 at the point or zone of discrete article transfer may be constant, or substantially constant (e.g., within 0.1%-2%) and matched to the tangential velocity of the first or second moving carrier members 104 or 106 or the heads 105 or 105' during transfer. This is accomplished by maintaining a substantially constant radial displacement between the zone of discrete article transfer and the first rotation axis 132. The radial displacement of the transfer surface 136 is adjusted as the follower members 112 travel over the projections 158 and 160. By providing constant, or substantially constant, tangential velocities of the transfer surfaces 136 at the point or zone of discrete article transfer, smoother and matched speed discrete article transfers may be accomplished. The projections 158 and 160 may be designed so that a first projection provides a transfer surface 136 with a first tangential velocity at a first point or zone of discrete article transfer (i.e., pick-up location) and a second projection provides the same transfer surface 136 with a second tangential velocity at a second point of discrete article transfer (i.e., drop-off location). As such, the transfer assembly 100 may pick up a discrete article 102 from the first moving carrier member 104 or the head 105 having a first velocity or tangential velocity at a first point or zone of discrete article transfer and may drop off the discrete article 102 onto the second moving carrier member 106 or the head 105' having a second velocity or tangential velocity at a second point or zone of discrete article transfer. In an instance, the transfer assembly 100 may be configured to pick up the discrete articles from the second moving carrier member 106 or head 105' and transfer them to the first moving carrier member 104 or head 105. In such an instance, the direction of rotation of the transfer members 112 about the rotation axis 132 may be clockwise or counterclockwise.

Although the angular velocity and tangential velocity of the heads 105 and 105' may be variable, the angular velocity and tangential velocity of the heads 105 and 105' may be constant, or substantially constant at the point or zone of discrete article transfer. The angular velocity or tangential velocity of the heads 105 and 105' may be the same as, or substantially the same as, the angular or tangential velocity of the transfer members 112 at the point or zone of discrete article transfer. In other instances, the angular or tangential velocity of the heads 105 and 105' may be different than, greater than, or less than, the angular or tangential velocity of the transfer members 112 at the point or zone of discrete article transfer, as will be discussed in greater detail below.

The transfer assembly 100 may be used to transfer discrete articles 102 from the first moving carrier member 104 or the head 105 at a first pitch (i.e., spacing of discrete articles) to a second moving carrier member 106 or the head 105' at a second pitch (i.e., repitching). The transfer assembly 100 is capable of achieving suitable transfer of the discrete articles 102 as the pitch increases, decreases, or remains the same between the first and second moving carrier members 104 and 106 or between the heads 105 and 105'.

Transferring the discrete articles 102 from the head 105' to the second moving carrier member 106 or from the transfer member 112 directly to the second moving carrier member 106 may provide suitable and efficient bonding of the discrete articles 102 to the webs of front and rear belts 124 and 126 or to front and rear belts. In an instance where the transfer member 112 place the discrete articles 102 directly onto the second moving carrier member 106, the constant gap clearance, or substantially constant gap clearance, may be adjusted to provide uniform, or substantially uniform, bonding pressure between the transfer surface 136 and the second moving carrier member 106. The head 105' and the second moving carrier member 106 may also be adjusted to interfere with the discrete article 102 and create bonding pressure that will be constant, or substantially constant, across the area of the discrete article 102 or the area of a portion of the discrete article 102. This may be useful for creating suitable bonds between the discrete article 102 and the webs of front and rear belts 124 and 126 when a hot melt adhesive or other pressure sensitive adhesive is employed.

The transfer assembly 100, with a variable radius transfer member mechanism, may also be employed to improve transfer from transfer surfaces that are not flat. For example, a transfer surface that is arcuate may benefit from adjusting the radial position of the transfer surface during transfer from the first moving carrier member 104 or the head 105 or to the second moving carrier member 106 or the head 105'. Likewise, a transfer surface that has any non-flat surface can be adjusted radially to improve the transfer from the first moving carrier member 104 or the head 105 to the second moving carrier member 106 or the head 105'. A person of ordinary skill in the art will recognize that the variable radius techniques described herein may be used with related art transfer assemblies as well as the transfer assemblies disclosed herein. As such, those concepts are encompassed by the present disclosure.

Referring to FIGS. 13-18, a rotation assembly 170 for one or more of, or all of, the transfer members 112 of the transfer assemblies 100 discussed herein may be provided. Portions of the transfer assembly 100, some transfer members, and other components are eliminated in FIGS. 13-18 for clarity in illustrating the rotation assembly 170. The rotation assembly 170 can be viewed on the transfer assembly 100 in FIGS. 7 and 8. The rotation assembly 170 may be simpler and less costly to manufacture than a barrel cam-type rotation assembly, may have extended follower member life, and may reduce the pressure angle of the track 134. As discussed above, the transfer assembly 100 may comprise a frame 130 defining a first rotation axis 132, wherein the one or more transfer members 112 may rotate about the first rotation axis 132 (see e.g., FIGS. 3, 4, and 6-8). The rotation assembly 170 may rotate portions of the transfer member 112 about the second rotation axis 164 between the first position 116 and at least a second position 118. The first rotation axis 132 may be perpendicular, or substantially perpendicular (e.g., 0.5 to fifteen degrees), or transverse to the second rotation axis 164. In other instances, the first rotation axis 132 may extend in a first direction and the second rotation 164 axis may extend in a second, different direction. The first rotation axis 132 may or may not intersect the second rotation axis 164.

Referring to FIGS. 13-20, the rotation assembly 170 may comprise a torque transmitting assembly 174 comprising an input member (or input portion) 176 and an output member (or output portion) 178. The torque transmitting assembly 174 may comprise a 90 degree gearbox or another type of gearbox. In other instances, the torque transmitting assembly may not comprise a gearbox and instead may be another mechanism for achieving torque transmission between perpendicular, or substantially perpendicular, shafts, such as worm gearing, bevel gearing, hypoid gearing, helical gearing, belt drives, chain drives, hydraulic drives, and/or three-dimensional space mechanisms, for example. The input member 176 and the output member 178 may be an input shaft and an output shaft, respectively. The shafts may have any suitable length and/or dimensions. The input member 176 may extend in a direction parallel to or substantially parallel to the first rotation axis 132 and the output member 178 may extend in a direction parallel to, substantially parallel to, or coaxial to the second rotation axis 164.

Figure 19:
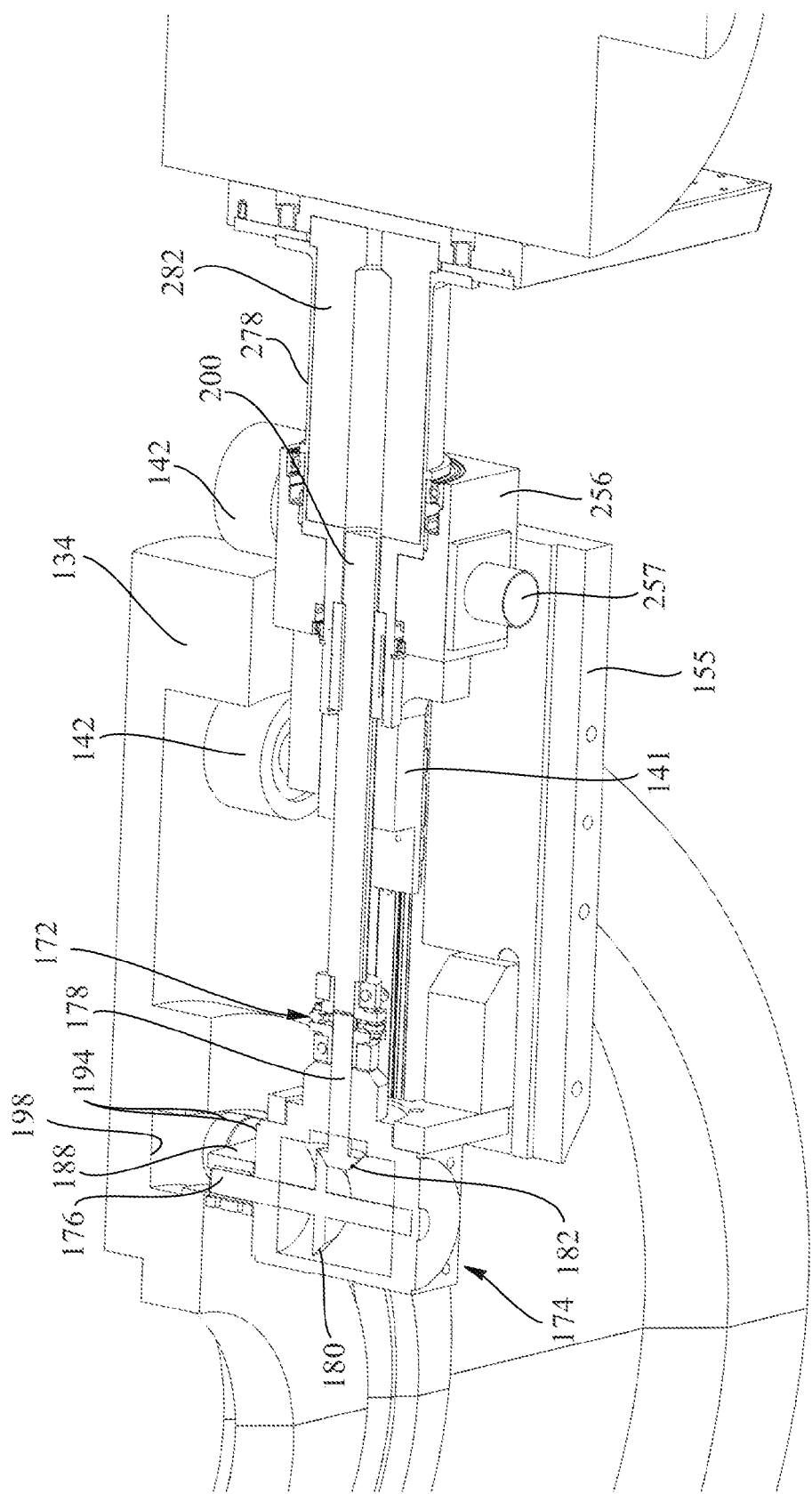
FIG. 19 is a cut away perspective view of the rotation assembly and the transfer member illustrating first and second gears in accordance with the present disclosure.
Figure 20:
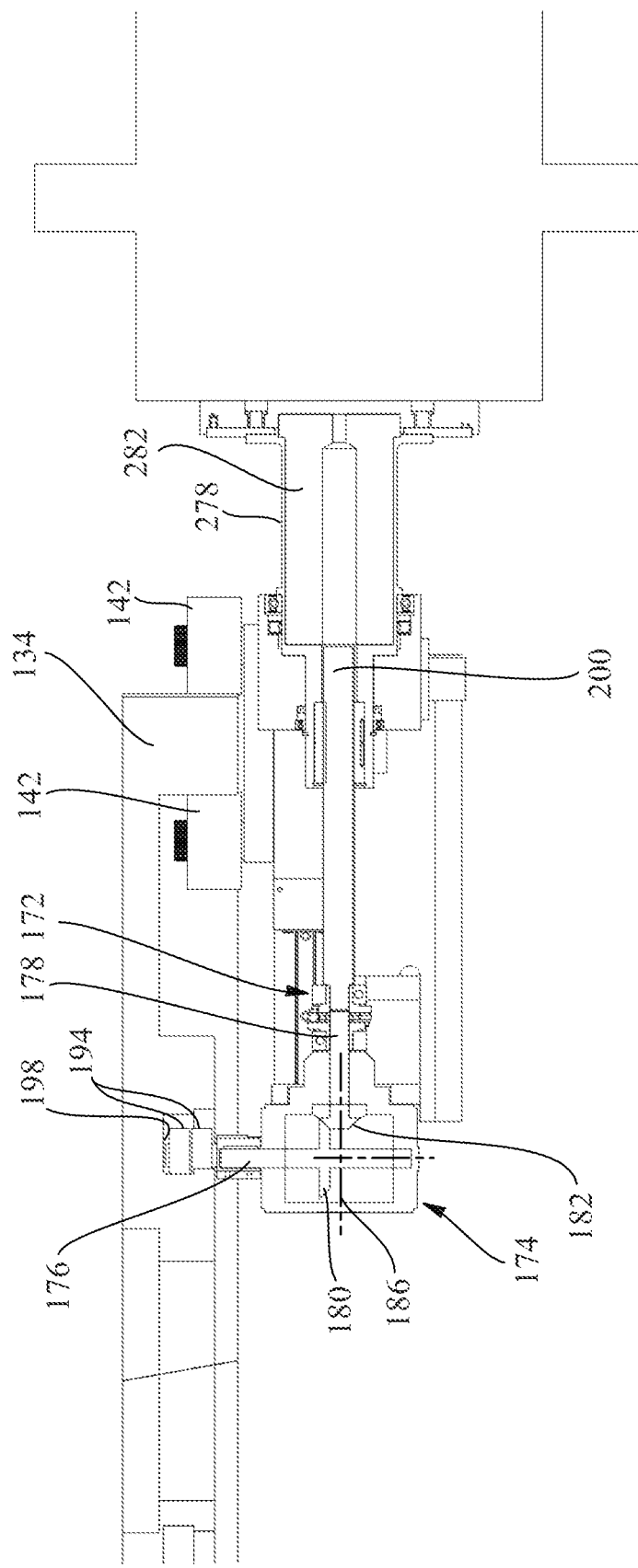
FIG. 20 is a cut away side view of the rotation assembly and the transfer member illustrating the first and second gears in accordance with the present disclosure.

Referring to FIGS. 19 and 20, the torque transmitting assembly 174 may comprise two or more gears. FIG. 19 is a partially cut away perspective view of the torque transmitting assembly 174, among other components, and FIG. 20 is a partially cut away top view of the torque transmitting assembly 174, among other components. The gears may each comprise teeth (not illustrated) meshingly engaged with each other. If two gears are provided, a first gear 180 may be operably engaged with the second gear 182 and may have a rotation axis 184 that is transverse, perpendicular, or substantially perpendicular to rotation axis 186 of the second gear 182. The torque transmitting assembly 174 may be a speed increasing assembly, such as a 1 to 1.5, 1 to 2, 1 to 2.5, or 1 to 3 gearbox, for example. Those of skill in the art will recognize that other speed increasing assemblies may also be used and that the speed may be increased any suitable amount. One example of a speed increasing assembly 174 is discussed in further detail below. In a form, the torque transmitting assembly 174 may be a speed decreasing or equal speed assembly, such as a 2 to 1, or a 1 to 1, gearbox, for example. Those of skill in the art will recognize that other speed decreasing assemblies may also be used and that the speed may be decreased any suitable amount.

The rotation assembly 170 may also comprise a link or bar 188 comprising a first end 190 operably coupled or fixedly attached to the input member 176 and a second end 192 comprising a follower member 194. The input member 176 may be operably coupled to the link 188 using a key 172 or other mechanical component or assembly configured to cause the input member 176 to rotate when the link 188 is rotated about its first end 190. Stated another way, the input member 176 may be non-rotatably attached to the link 188, such that when the link 188 is rotated about its first end 190, the input member 176 rotates in unison with the first end 190 of the link 188. The link 188 may be rotated about its first end 190 when the follower member 194 is moved radially relative to the first rotation axis 132 by a track 198, as discussed in greater detail herein. The follower member 194 may be a cam follower, which, in one form, may comprise a roller rotatably attached to or engaged with the second end 192 of the link 188. In various forms, the follower member may not be a roller and may be attached to or formed with the second end 192 of the link 188. The one or more of the follower members 194 may comprise materials such as metals, plastics, and/or polymers, for example, or coatings thereof, to permit relative movement between the one or more follower members 194 and the track 198 194 (also referred to as a second track 198) for the follower members. The follower members 142 and the track 134 may comprise similar features. This second track 198 may surround the first rotation axis 132 and be surrounded by the first track 134 described above. In any event, the "inner" track 198 may be engaged with the follower member(s) 194 of the rotation assembly 170. The track 198 may comprise or be coated with the same, similar materials, or different materials as the follower members 170, for example.

Referring again to FIGS. 13-18, the rotation assembly 170 may comprise a shaft or a shaft assembly 200 comprising a first end 202 engaged with or operably coupled to the output member 178 of the torque transmitting assembly 174 and a second end 204 engaged with or operably coupled to a portion of the transfer member 112. The first end 202 of the shaft 200 may be operably coupled to the output member 178 using the key 172 so that when the output member 178 is rotated, the shaft 200 may be rotated at least partially about the second rotation axis 164. Stated another way, the rotation of the output member 178 may drive the rotation of the shaft 200. A portion of, or all of, the shaft 200 may have a slot or groove (not illustrated) defined therein in a direction extending parallel to, or substantially parallel, to its longitudinal axis. A key (not illustrated) may extend from a portion of the transfer member 112 or from the output member 178 at or proximate to the point of coupling to the shaft 200. The key may allow the transfer member 112 to be moved radially inwardly and outwardly relative to the first rotation axis 132 as portions of the transfer member 112 rotate about the first rotation axis 132 about a path in correspondence with the first track 134, as discussed above. The shaft 200 may extend into a portion of the transfer member 112, such as the fluid manifold 256 and the housing 278, or the torque transmitting assembly 174 so that the distance between a shaft receiving portion of the transfer member 112 and the output member 178 (i.e., the length of the portion of the shaft 200 intermediate the shaft receiving portion of the transfer member 112 and the torque transmitting assembly 174) may be varied. The key may also allow the shaft 200 to be turned about the second rotation axis 164 by the output member 178. In essence, the key/slot feature allows the shaft 200 to be rotated about the second rotation axis 164 and to vary the distance of the portion of the shaft 200 intermediate the shaft receiving portion of the transfer member 112 and the torque transmitting assembly 174.

The shaft may comprise a shaft assembly 200 comprising a spline 206 and a spline receiving member 208. The spline receiving member 208 may be positioned on or engaged with a portion of the transfer member 112 or the output member 178 at or proximate to the point of engagement with an end portion of the spline 206. If the spline receiving member 208 is positioned on the output member 178, the output member 178 may be hollow such that the spline may extend therethrough. The spline 206 may be slidably engaged with the spline receiving member 208 such that the distance between the most proximal portion of the transfer member 112 and the output member 178 may be varied as the transfer member 112 is moved radially relative to the first rotation axis 132. The end of the spline 206 not engaged with the spline receiving member 208 may be engaged with or operably coupled to the output member 178 or to a portion of the transfer member 112. In such a form, as the transfer member 112 is moved radially outwardly or radially inwardly as it circumnavigates about the path of the first track 134, the length of the portion of the spline 206 intermediate the transfer member 112 and the output shaft 178 may be varied. The spline 206 and the spline receiving member 208 may allow the output member 178 to rotate the spline 206 about the second rotation axis 164 while the transfer member 112 is moved radially relative to the first rotation axis 132. Those of skill in the art will recognize that other shaft assemblies that allow adjustment of the length of the portion of the shaft between the transfer member 112 and the output member 178 are within the scope of the present disclosure.

Although not illustrated, a shaft assembly may comprise a shaft portion and a shaft receiving portion. The shaft may be slidably engaged with the shaft receiving portion in a telescoping fashion (not illustrated) to allow axial expansion and contraction of the shaft assembly relative to the first rotation axis. The shaft may be non-rotatably engaged with the shaft receiving portion such that the output member 178 may rotate the shaft and the shaft receiving portion.

Figure 14:
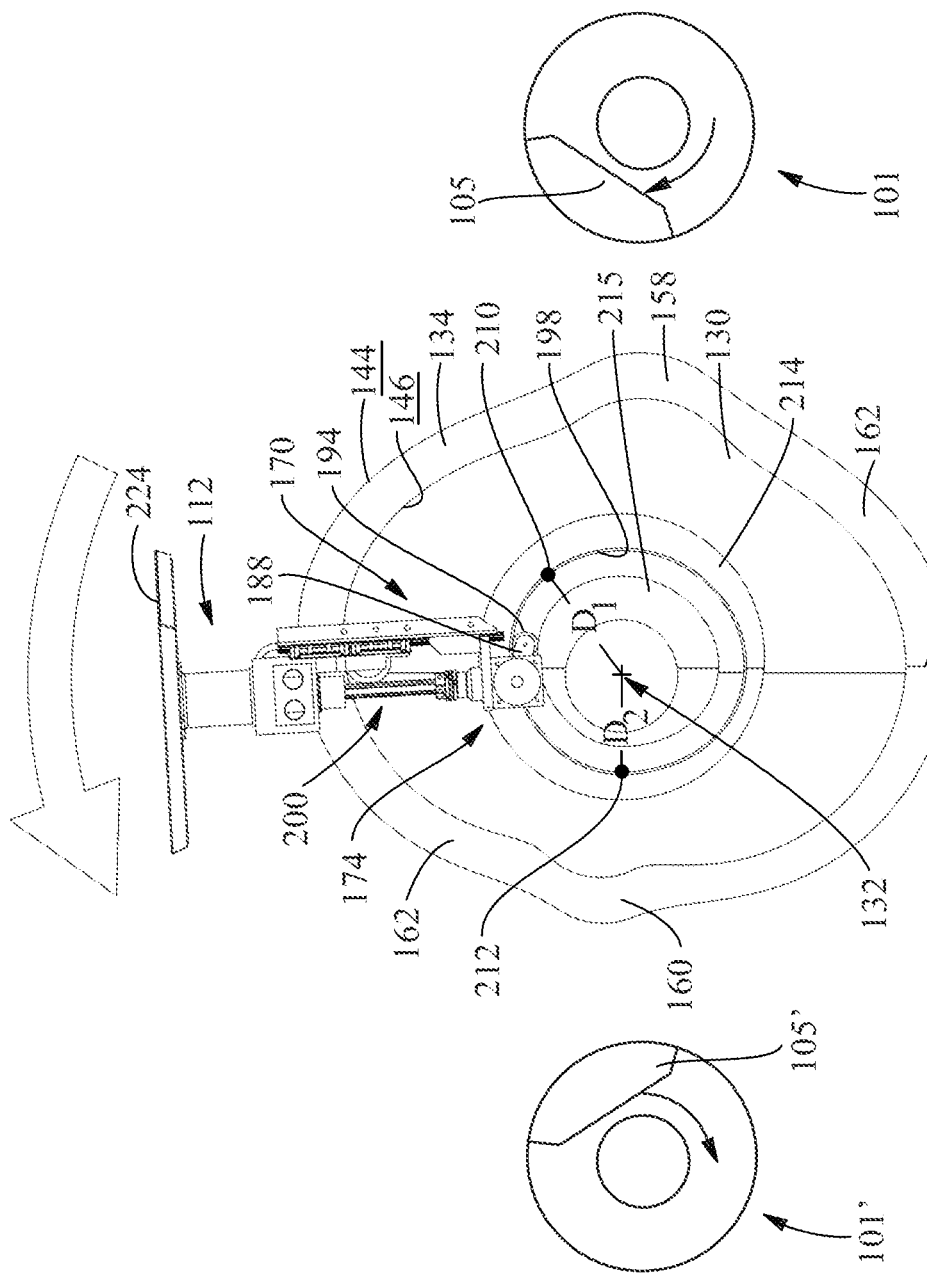
FIG. 14 is a front view of the two tracks, the rotation assembly, the apparatuses comprising heads, and a transfer member, wherein portions of the transfer member are moving from a first position into a second position in accordance with the present disclosure.

Referring to FIGS. 7, 8, 10, and 13-15, the rotation assembly 170 may be engaged with the track or second track 198 positioned on or in the frame 130 and surrounding the first rotation axis 132. The second track 198 may be surrounded by the first track 134 such that the second track 198 may be an inner track and the first track 134 may be an outer track relative to the first rotation axis 132. The inner track and the outer track may be referred to as a track, a first track, or a second track depending on which of the tracks is recited first. Referring to FIG. 14, a first point 210 at a first location on the second track 198 may be first distance, D1, away from the first rotation axis 132 and a second point 212 at a second location on the second track 198 may be a second distance, D2, away from the first rotation axis 132. The first distance, D1, may be different than the second distance, D2. Other points on the second track 198 may be other distances away from the first rotation axis 132. This distance variation of various points on the second track 198 relative to the first rotation axis 132 may allow the shaft or shaft assembly 200 to rotate about the second rotation axis 164, thereby moving a portion of the transfer member 112 between the first position 116 and at least the second position 118.

The second track 198 may be a cam track or a radial cam, for example. In an instance, although not the illustrated form, but similar to the first cam track 134, the second track 198 may extend outwardly from a front plane of the frame 130 and form a projection that surrounds the first rotation axis 132. In such a form, the second track 198 may be formed with the frame 130 or may be attached to the frame 130. The projection may comprise a first side surface, a second side surface, and a top surface. The first side surface may be positioned parallel to, or substantially parallel to (e.g., 0.5 to 15 degrees), the second side surface. The top surface of the projection may extend in a direction parallel to, or substantially parallel to, the plane of the frame 103 and in a direction perpendicular to, or substantially perpendicular to, the first and second side surfaces. The distance between the first side surface and the second side surface may be constant, substantially constant, or variable about the projection. Two follower members may be engaged with, attached to, or formed with the second end 192 of the link 188 and may each be movably engaged with one of the side surfaces of the projection. Two links, each comprising a follower member on their second end, may be provided if two follower members are provided, as will be recognized by those of skill in the art. The follower members may be biased toward the side surfaces of the projection.

Figure 15:
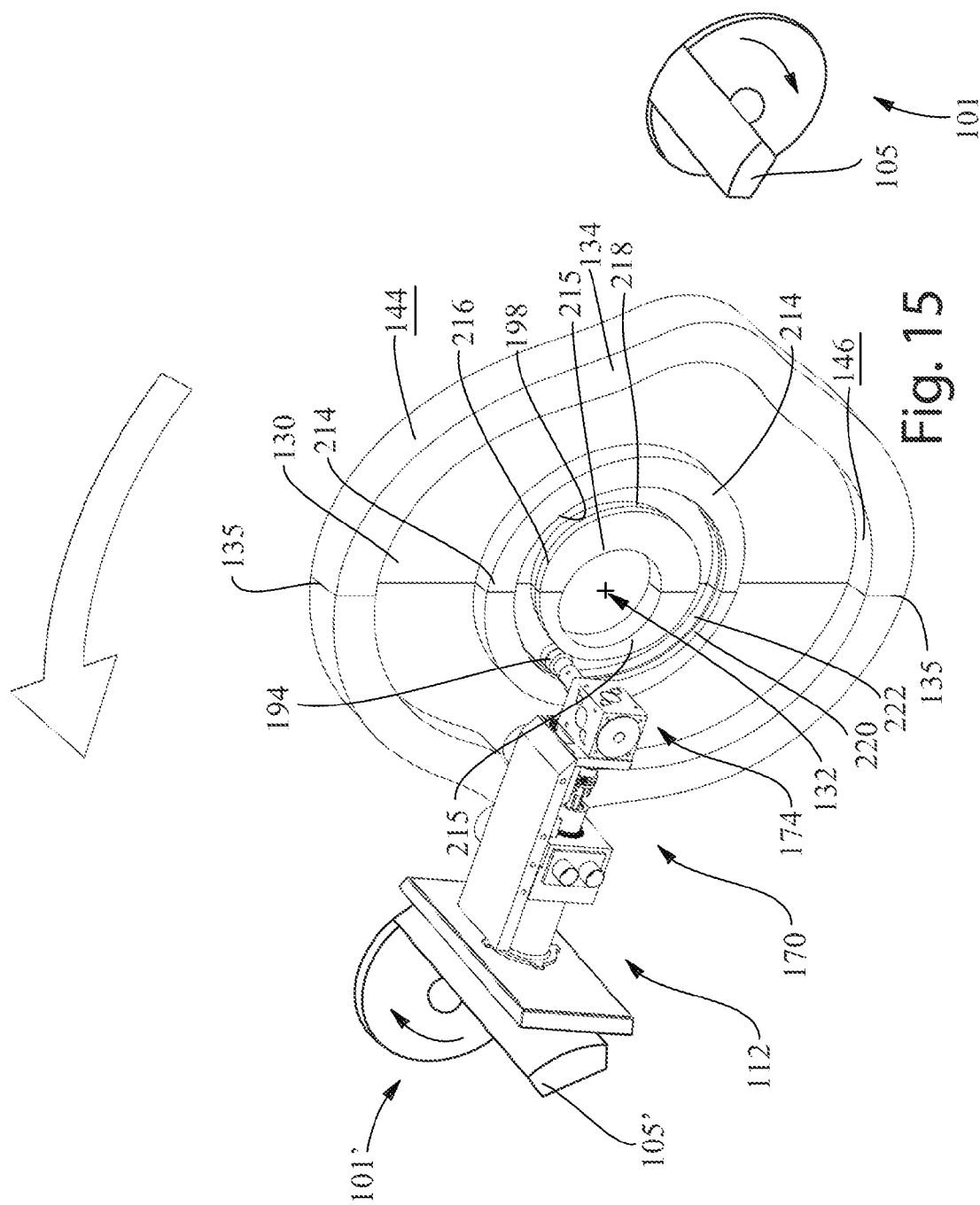
FIG. 15 is a front perspective view of the two tracks, the rotation assembly, the apparatuses comprising the heads, and the transfer member, wherein a portion of the transfer member is in a drop-off zone in a second position, in accordance with the present disclosure.

Referring to FIGS. 13-15, the second track 198 may be a cam track or groove defined in a front plane of the frame 130 and surrounding the first rotation axis 132. The cam track or groove may optionally be surrounded by a projection 214 positioned more radially outward from the first rotation axis 132 than the groove. The projection 214 may have a constant width or may have a variable width throughout its circumference. By providing the projection 214, the groove may be partially, or fully, defined in a front plane of the frame 130. The groove may also be formed intermediate the projection 214 and another projection 215 extending from the front plane of the frame 130. If the projection 214 is not provided, the groove may be fully defined in a front plane of the frame 130. In various forms, one or more of the follower members 194 may be at least partially positioned with the cam track or groove 198 and may engage side walls of the second cam track or groove 198 as the transfer member 112 rotates about the first rotation axis 132. Any of the follower members 194, regardless of whether the second track 198 is a projection or a groove, may be moveably engaged with the second track 198 and may circumnavigate about the first rotation axis 132 about a path in correspondence with the second track 198.

Referring to FIGS. 13-15, the groove of the second track 198 may have a first surface 216 and a second surface 218 on a portion of the groove most proximal to the rotation axis 132. The projection 214 may also have a first surface 220 and a second surface 222 on a portion of the projection most proximal to the rotation axis 132. The first surface 216 and the second surface 218 may extend different distances from the first rotation axis 132. Likewise, the first and second surfaces 220 and 222 may be positioned at different distances from the first rotation axis 132. A distance between the first surface 216 and the first surface 220 may be the same, or substantially the same, and, likewise, a distance between the second surface 218 and the second surface 222 may be the same, or substantially the same. Stated another way, the first surface 216 may be offset from the second surface 218 and the first surface 220 may be offset from the second surface 222. In such a form, the second end 198 of the link 188 may comprise a first follower member 194 and a second follower member 194. The follower members 194 may be rotatably engaged with the second end 198 of the link 188 using a pin, bolt, or other attachment mechanism or component. The follower members 194 may be positioned adjacent to each other and may each rotate about the pin or bolt, for example. The first follower member 194 may be engaged with the first surface 216 and the second follower member 194 may be engaged with the second surface 222. Surfaces 218 and 220 may not be engaged by the follower members 194 due to the offset of the surfaces 218 and 220 relative to the surfaces 216 and 222. By providing essentially two cam tracks in the groove and two follower members 194, each follower member may only turn in one direction. In other forms, the second track 198 may only have one surface on each side of the groove and only one follower member 194 may ride within the track 198.

Referring to FIGS. 7, 8, 10, and 13-20, when the one or more follower members 194 are moved radially relative to the first rotation axis 132 as they circumnavigate about the path in correspondence with the second track 198, the link 188 may be rotated in a clockwise or counterclockwise direction about its first end 190 thereby imparting a rotational force or torque to the input member 176. The torque transmitting assembly 174 may then impart the rotational force to the output member 178 and, thereby the shaft or the shaft assembly 200 owing to the gearing arrangement within the torque transmitting assembly 174. In a form, the input member 176 may be rotated with the first end 190 of the link 188 a first rotational distance and may impart a second rotational distance to the output member 178 and, thereby the shaft or shaft assembly 200, owing to the gearing arrangement within the torque transmitting assembly 174. The second rotational distance may be greater than the first rotational distance. The rotation of the shaft or the shaft of the shaft assembly 200 may cause the transfer member 112 to move between the first position 116 and the second position 118 about the second rotation axis 164. At least a portion of this rotation between the first position 116 and the second position 118 may occur when the first track 134 has radially expanded the distance between the transfer member 112 and the output member 178 or when the transfer member 112 has been moved radially outwardly by the first track 134 relative to the first rotation axis 132. The second rotation axis 164 may be an axis formed about a longitudinal axis of the shaft or the shaft of the shaft assembly 200. In one revolution of the transfer member 112 about the first rotation axis 132, the shaft or the shaft of the shaft assembly 200 may be rotated from the first position 116 into the second position 118 and back into the first position 116. The transfer surfaces 136 may be rotated between about 45 degrees to about 180 degrees, about 60 degrees to about 150 degrees, about 75 degrees to about 105 degrees, about 90 degrees (e.g., plus or minus 3 degrees), or 90 degrees, specifically reciting all 0.5 degree increments within the above-specified ranges and all ranges formed therein or thereby, when the transfer member 112 is moved between the first position 116 and the second position 118.

The second track 198 may vary the angle of the transfer member 112 rotating about the second rotation axis 164 due to the changing radius of the follower member 194. The second track 198 may also have dwell regions therein where the radius of the follower members 194 and the rotation angle of the transfer members 112 remain constant, or substantially constant. These dwell regions may be useful when the transfer member is in the first position 116 and in the second position 118 during the transfer of the discrete articles 102 from the first moving carrier member 104 or the head 105 to the second moving carrier member 106 or the head 105'.

Although the rotation assembly 170 is illustrated in use with the transfer assembly 100 as an example, the rotation assembly 170 may be applied to other transfer assemblies known to or developed by those of skill in the art and may function independently of the transfer assembly 100. Other transfer assemblies than the rotation assembly 170 of the present disclosure may be used with may not have transfer members that move radially relative to the first rotation axis 132. In one example, the rotation assembly 170 may be used with transfer members that have a varying angular position about the first rotation axis 132, for example.

The transfer members 112 may be cammed or moved radially outwardly to provide clearance for rotation of the transfer members 112 about the second rotation axis 164 with adjacent transfer members 112. In other instances, the spacing or shape of the transfer members 112 may not require increasing their radial position for rotation about the second rotation axis 164. In another form, the radius of the transfer members 112 may decrease to provide clearance for transfer member rotation about the second rotation axis 164. In another instance, the transfer members 112, or portions thereof, may tilt relative to first rotation axis 132 to allow clearance with adjacent transfer members 112 during rotation about the second rotation axis 164.

A method of transferring one or more discrete articles from a first moving carrier member or head of an apparatus to a second moving carrier member or head of an apparatus using a transfer assembly is provided. The transfer assembly may comprise a frame defining a first rotation axis and one or more transfer members each comprising a transfer surface configured to receive one or more of the discrete articles. The method may comprise rotating the one or more transfer members about the first rotation axis and selectively varying the radial distance of the one or more transfer surfaces relative to the first rotation axis as the one or more transfer member rotate about the first rotation axis. The method may also comprise rotating the one or more transfer surfaces, and other portions of the transfer members, about a second rotation axis between a first position and at least a second position using a track that surrounds the first rotation axis, one or more follower members circumnavigating about a path in correspondence with the track while the transfer member rotates about the first rotation axis, a torque transmitting assembly, a link comprising a first end operably coupled to a first portion of the torque transmitting assembly and a second end comprising the one or more follower members, and a shaft assembly operably engaged with a second portion of the torque transmitting assembly on a first end and engaged with a portion of the transfer member on a second end. The first portion or input portion of the torque transmitting assembly may be positioned parallel to, or substantially parallel to, the first rotation axis and the second portion or output shaft of the torque transmitting assembly may be positioned parallel to, or substantially parallel to, the second rotation axis. The method may comprise expanding and contracting the length of the shaft assembly between each transfer member and each output portion during the selectively varying of the radial distance of the one or more transfer surfaces relative to the first rotation axis. The method may also comprise rotating the one or more transfer surfaces at least partially between the first and second positions when the length of the shaft assemblies between the transfer members and the output portions are expanded and turning the discrete article through the rotation of the transfer surfaces between the first position and the second position. The transfer surfaces, and other portions of the transfer members, may be rotated from the first position into the second position in a first direction of rotation and may be rotated from the second position into the first position in a second direction of rotation. The first direction of rotation may be opposite to the second direction of rotation. In other instances, the first direction of rotation may be the same as the second direction of rotation. One or more of the discrete articles may be retained to or pushed from the transfer surfaces using a fluid pressure, such as a negative or a positive fluid pressure, for example.

The various discrete articles 102 (e.g., a chassis of an absorbent article) or flexible discrete articles 102 may be retained to the various transfer surfaces 136 of the transfer members 112 or the surfaces of the heads 105 and 105' of the present disclosure in many ways, including but not limited to, fluid pressure, mechanical attachment via pins or grippers, adhesives, such as pressure sensitive or low tack adhesives, static attraction, and/or magnetic attraction, for example. Fluid pressures and/or other forces may also be used to force or move the discrete articles 102 from the transfer surfaces 136 or surfaces of the heads 105 and 105' onto a moving carrier member, such as the second moving carrier member 106.

Referring to FIGS. 1, 4-6, 8, 9, 16, and 18, for example, the transfer assembly 100 may comprise a fluid system configured to retain the discrete articles 102 to one or more of the transfer surfaces 136 of the transfer members 112. Each of or one of the transfer members 112 may have one or more fluid ports 230 defined through the transfer surface 136 thereof, or through portions or zones of the transfer surface 136. The fluid ports 230 may have any suitable shape, such as elongate slots, circular or ovate openings, and/or rectangular, square, or triangular openings, for example. The fluid ports 230 may also have mesh, screen, or other porous materials extending thereover. The fluid ports 230 may be linear or non-linear, continuous or non-continuous. In a form, a first transfer member may have a transfer surface having a first pattern of fluid ports and a second transfer member may have a transfer surface having a second pattern of fluid ports. In other instances, the patterns on all of the transfer surfaces 136 may be the same. A positive or a negative (vacuum) fluid pressure may be applied to the fluid ports 230 through various fluid conduits and fluid lines. Some fluid ports, at various times, may not have any fluid pressure being applied thereto. The fluid pressures may initiate in one or more fluid movement devices or sources 232, 234, such as one or more fluid pumps, vacuum pumps, pressure blowers, or fans. The fluid may be air or other gas, for example. Some fluid ports 230 may be configured to provide a positive pressure, while at the same time, other fluid ports 230 of the same transfer member 112 may be configured to provide a negative pressure or no fluid pressure. In various instances, some of the fluid ports 230 may be configured to provide a first fluid pressure (positive or negative), while at the same time, other fluid ports 230 of the same transfer member 112 may be configured to provide a second fluid pressure (positive or negative). The first fluid pressure may be greater than or less than the second fluid pressure. In other instances, the fluid ports 230 in one transfer member 112 may have a different fluid pressure as the fluid ports 230 in another transfer member 112 on the same transfer assembly 100 owing to factors like the number of the fluid ports 230 or the areas of the fluid ports 230 on a particular transfer surface 136. For example, one fluid pressure may be applied at a pick-up location and another fluid pressure may be applied at a drop-off location. In other instances, the fluid pressure applied to the fluid ports 230 may vary in different fluid ports 230 or zones of the fluid ports 230 in a transfer member 112 at the pick-up location and at the drop-off location.

Referring to FIGS. 1 and 4-9, the fluid system used to provide the fluid pressure to the fluid ports 230 may comprise the first fluid movement device 232 and the second fluid movement device 234. The first and second fluid movement devices 232 and 234 may supply a positive fluid pressure and/or a negative fluid pressure to first and second fluid lines 236 and 238. The first and second fluid movement devices 232 and 234 may be controlled independently or controlled together for various applications. In an instance, only one fluid movement device may be provided. That single fluid movement device may be configured to supply the first and second fluid lines 236 and 238 with positive and/or negative fluid pressures. The fluid pressure and flow rates applied to the first and second fluid lines 236 and 238 may be equal or different. In an instance, the single fluid movement device may supply a positive pressure to the first fluid line 236 and a negative pressure to the second fluid line 238, for example.

Referring now to FIGS. 1 and 4-6, the apparatuses 101 and 101' will be discussed in greater detail. As stated herein, in certain instances, only one apparatus may be provided on either the input side or output side of the transfer assembly 100. If the apparatus 101 is provided only on the input side of the transfer assembly 100, the discrete articles 102 may be transferred from the first moving carrier 104 to a head 105 of the apparatus 100, then from the head 105 of the apparatus 101 to the transfer member 112, and then from the transfer member 112 directly to the second moving carrier member 106. If the apparatus 101' is provided only on the output side of the transfer assembly 100, the discrete articles 102 may be transferred directly from the first moving carrier member 104 to the transfer member 112, then from the transfer member 112 to the head 105' of the apparatus 101', and then from the head 105' to the second moving carrier member 106. In certain operations, more than one apparatus may also be provided on either the input side or the output side of the transfer assembly, or both. In other certain instances, the first and/or second moving carrier members 104 and 106 may be eliminated and only the apparatus 101 and/or 101' may be used.

Each of the apparatuses 101 and 101' may comprise one or more heads 105 and 105', respectively. Each apparatus 101 and 101' may have a rotation axis 107 and 107', respectively. The heads 105 and 105' may be rotated about the rotation axis 107 and 107', respectively, at a variable angular velocity or at a plurality of angular velocities. For example, each of the heads 105 and 105' may be rotated about a first, second, third, fourth or more angular velocities within one revolution of the head about the rotation axis 107 and 107', respectively.

Figure 21:
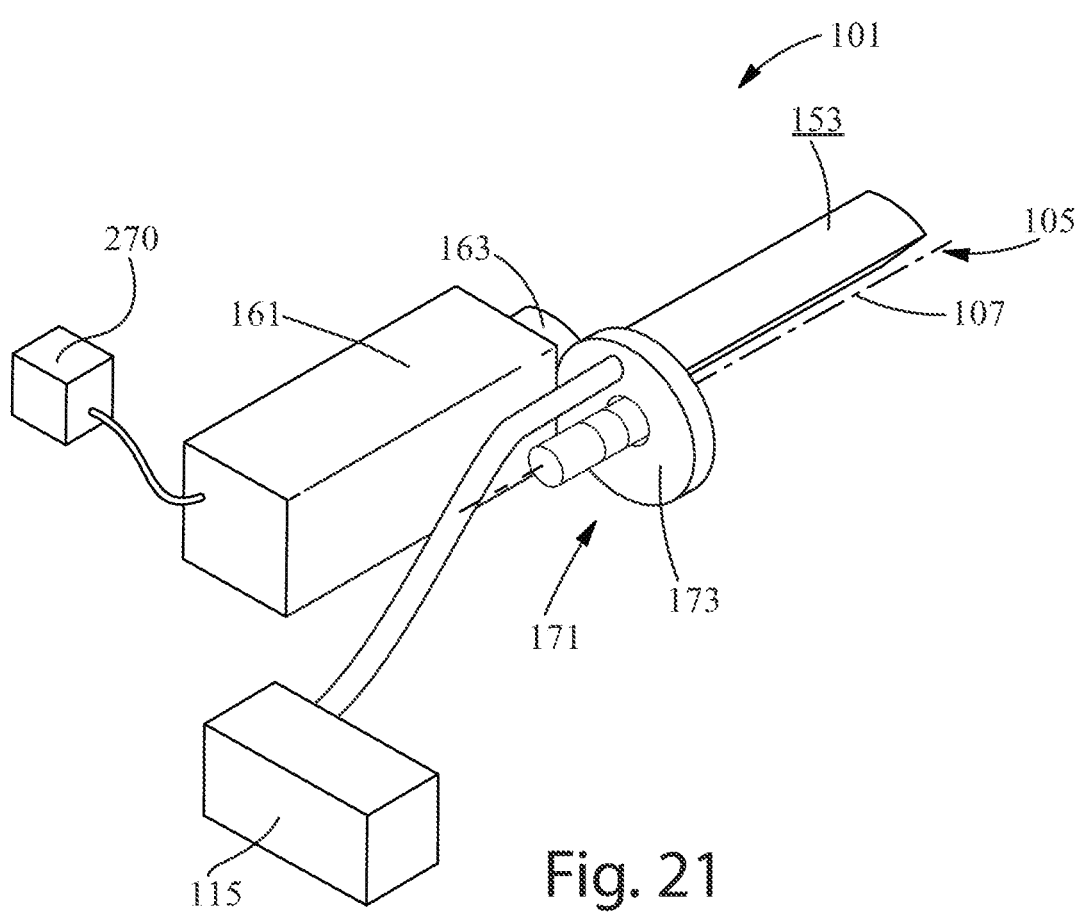
FIG. 21 is a perspective view of an example apparatus comprising a head in accordance with the present disclosure.
Figure 22:
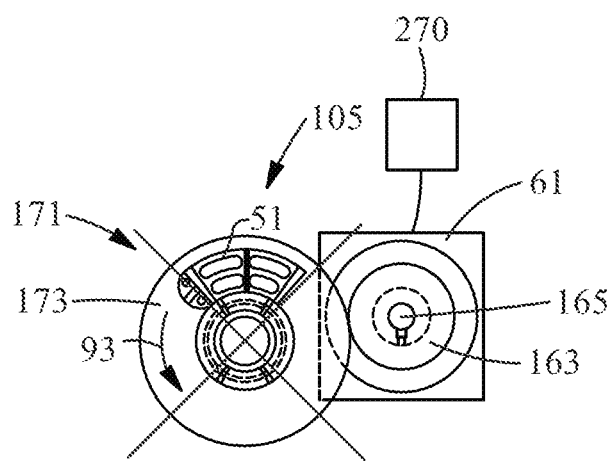
FIG. 22 is a front view of the example apparatus comprising the head of FIG. 21 in accordance with the present disclosure.

Referring to FIGS. 21 and 22, an example apparatus comprising a single head is illustrated. The apparatus 101 may comprise a motor 161 for transmitting rotational energy to a transfer device 171. The motor 161 may be operably linked or operably engaged with the transfer device 171 using any technique known to those skilled in the art such as, for example, a gear to gear connection, transmission belting and pulleys, gearboxes, direct couplings, and the like or any combinations thereof. For example, in FIG. 21 the transfer device 171 may comprise a driven gear 173 that is connected to a driving gear 163, which transmits rotational energy to the driven gear 173. In use, the driving gear 163 may engage and rotate the driven gear 173 which, in turn, may rotate a head 105 of the apparatus 101 about rotation axis 107. The apparatus 101' and the head 105' may be generally the same as, or very similar to, that described for the apparatus 101 and the head 105. In other instances, the apparatus 101' and/or the head 105' may be different in size, speed, and/or configuration, for example.

In some instances, the transfer device 171 may be formed with a portion of the head 105. The head 105 may comprise a surface 153 configured to receive a discrete article 102. The head 105 may be connected to the transfer device 171 by any technique known to those skilled in the art such as, for example, bolts, screws, pins, keys and matching key ways, connector parts such as shafting or brackets, adhesive bonding or gluing, welding and the like or combinations thereof. For instance, the head 105 shown in FIG. 21 may be connected directly to the driven gear 173 by fitting the end of the head 105 into a mating hole in the driven gear 173 and locking it into position with a pin. In other instances, the head 105 may be formed with the transfer device 171.

The dimensions of the head 105 may vary depending upon the desired output of the apparatus 101 and the size and shape of the discrete articles 102 being transferred. The head 105 may comprise a crescent-shaped member having an outer, peripheral arc length spanning from about 5 degrees to about 355 degrees, an outer radius ranging from about 10 mm to about 1,000 mm or about 25 mm to about 500 mm, and a width ranging from about 25 mm to about 1,000 mm or about 50 mm to about 750 mm, specifically reciting all 0.1 increments within the above-specified ranges and all ranges formed therein or thereby. Other suitable dimensions are also within the scope of the present disclosure. As the transfer device 171 rotates, the head 105 may travel in the direction indicated by arrow 93 as shown in FIG. 22. The head 105 may pass through a pick-up zone and a drop-off zone as it rotates about the rotation axis 107. In the pick-up zone, the head 105 may receive a discrete article 102 from the first moving carrier member 104 (if present) (on the input side of the transfer apparatus 100) and the head 105' may receive the discrete article 102 from the transfer member 112 (on the output side of the transfer apparatus 100). In the drop-off zone, the head 105 may provide a discrete article 102 to a transfer member 112 (on the input side of the transfer apparatus 100) and the head 105' may provide the discrete article 102 to the second moving carrier member (if present) (on the output side of the transfer apparatus 100).

The motor 161 may be configured to move the head 105 at a plurality of angular velocities throughout one full revolution of the head about the rotation axis 107.

One illustrated example of the motor 161 comprises, or is operably linked to, a rotatable circular driving gear 163 operably connected to an input shaft 165. In this example, the input shaft 165 is the output shaft of the motor 161. The transfer device 171 may be placed parallel to the motor 161 such that the driving gear 163 meshes with the driven gear 173 using gear set-ups known to those skilled in the art. In use, the motor 161 may rotate the input shaft 165, which rotates the driving gear 163, which, in turn, rotates the driven gear 173 and, thereby, rotates the head 105 about the rotation axis 107. A similar method of operation would apply to the apparatus 101' and the head 105'.

In other forms, the transfer device 171 may comprise any mechanism or mechanisms known to those skilled in the art by which rotational energy may be conducted from one shaft to another such as, for example, v-belts, timing belts, continuous chains and the like or combinations thereof. Further, the transfer device 171 may comprise any mechanism or mechanisms known to those skilled in the art by which input velocity can be variably modified to an output source such as, for example, cams, linkages, and the like or combinations thereof as long as the changes in rotational speed are substantially created by the motor 161. It will be further appreciated that the apparatuses 101 and 101' of the present disclosure may utilize one or, in the alternative, two, three, four or more combinations of heads 105 or 105'.

The heads 105 and 105' may comprise one or more gripping mechanism so that the surface of the heads 105 and 105' may engage a discrete article 102. The gripping mechanism(s) may comprise a fluid pressure (e.g., vacuum) that may be selectively imposed through fluid ports the head 105 leading to the surface 153 of the head 105. For instance, the fluid pressure may be activated when picking up a discrete article 102 and deactivated when releasing the discrete article 102. In other instances, a negative fluid pressure (i.e., vacuum) may be activated when picking up the discrete article 102 in a pick-up zone and a positive fluid pressure may be activated to "blow off" the discrete article 102 in a drop-off zone. In this manner, control may be maintained over the discrete articles 102 at all times during the transfer process. Alternatively, the gripping mechanism(s) may comprise any technique known to those skilled in the art for gripping and releasing discrete articles 102 such as, mechanical clamps, adhesives, electrostatic charges, electrical clamps, magnetic clamps, and the like or combinations thereof.

The motor 161 may comprise a programmable motor, such as a programmable rotary motor or a programmable linear motor. The use of a programmable motor may provide an inexpensive and adaptable method for receiving the discrete articles 102 at a first tangential and angular velocity and applying the articles at a second, different tangential and angular velocity. The variable angular velocity of the head 105 throughout one revolution of the head 105 about the rotation axis 107 may be produced by varying the current supplied to the motor 161. Since the transfer device 171 is operably coupled to the output of the motor 161, changes in the angular velocity and position of the motor 161 may directly correlate to changes in the angular velocity and position of the head 105. The current supplied to the motor 161 may be controlled using any of a variety of methods for programming motors known to those skilled in the art such as, standard cam curve functions, a reference data table containing reference points, desired motor encoder points, and the like or combinations thereof.

The programmable motors used to drive the heads 105 and 105' may provide variable angular velocities to the heads 105 and 105', including periods where the angular velocity remains constant for a fixed duration. These constant angular velocity dwell times may be advantageous when picking up and transferring a discrete article, particularly when the pick-up and transfer occurs over substantial arc lengths of contact. Alternatively, one or more of the constant speed regions may be changed to a controlled variable speed region. This may enable the discrete article 102 to be picked up at a variable speed, which, when the discrete article 102 is elastic, would allow tensions to be varied incrementally therein which may be desirous in certain product features. In another example, the constant speed of the motor 161 in a drop-off zone may be such that the corresponding speed of the head 105 is different from, such as less than, the speed of the second moving carrier member 106 at transfer. Such speed variations may generate tension in the discrete article 102 by incrementally transferring the discrete article 102 in a controlled manner from the head 105' traveling at a first tangential speed to the second moving carrier member 106 moving at a second tangential speed or linear speed when the second moving carrier member is a linear conveyor.

It will be further appreciated that the tangential and angular velocities of the head 105 outside of the pick-up and drop-off zones may be tailored to aid the performance of secondary processes including adhesive application, printing of identification or registration marks, application of bonding aids, moisture addition, and the like and combinations thereof. Such changes in the tangential and angular velocities may be beneficial by presenting specific velocity profiles or even additional periods of constant velocity, which may allow for more precise interaction with the secondary processes being performed.

Programmable motors may be purchased from any number of suppliers of programmable motors such as Rockwell Automation, located in Milwaukee, Wis. Further, the program inputs to the motors can be generated by one of ordinary skill in the art if provided with the analytical representation of the desired output function. For instance, the creation of the electronic cam profile for the motor may be developed by first determining the key input variables. Some key input variables are based on desired product features, the base design of the apparatus 101 and the desired cycle speed of the apparatus 101. Secondly, the radius of the outer surface of the head 105 is determined Once the radius is determined, the required cam inputs of rotational velocities, distances traveled and time available for acceleration may be calculated, which serve as the input to the cam profile generator. Additional details regarding these calculations are disclosed, for example, in U.S. Pat. No. 6,450,321 to Blumenthal et al.

Figure 23:
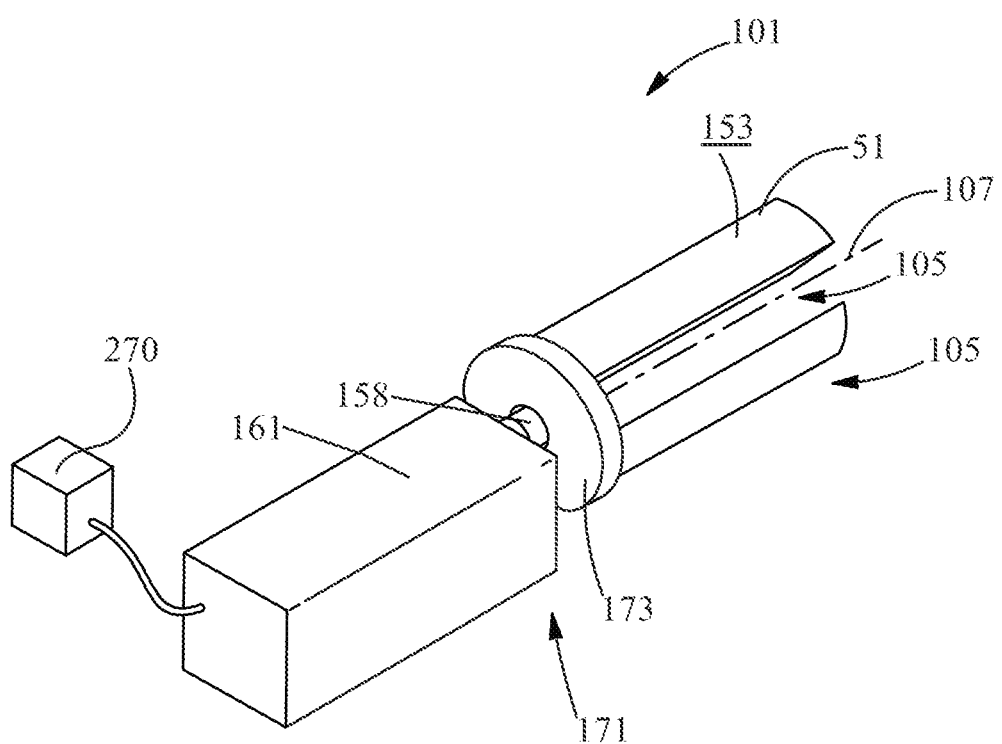
FIG. 23 is a perspective view of another example apparatus comprising two heads in accordance with the present disclosure.
Figure 24:
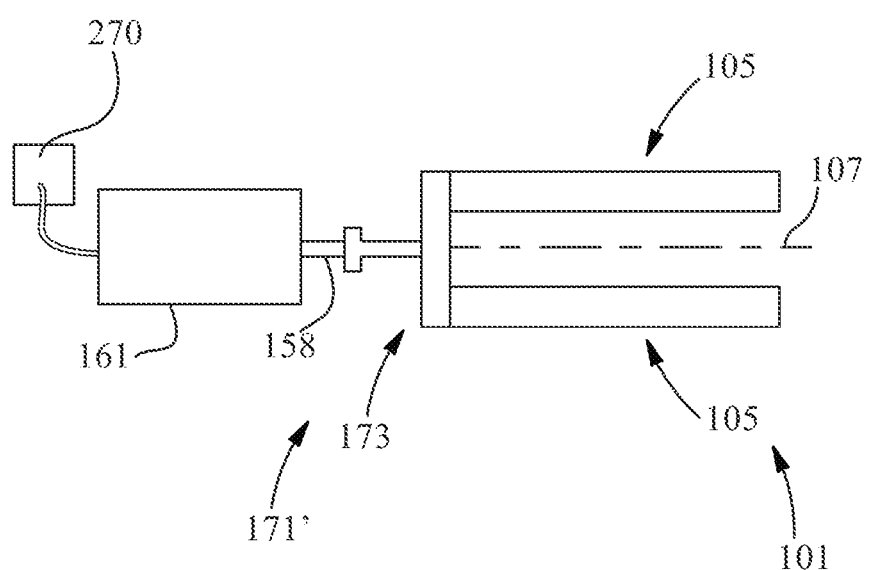
FIG. 24 is a side view of the example apparatus comprising the two heads of FIG. 23 in accordance with the present disclosure.

Referring to FIGS. 23 and 24, another example form of an apparatus 101 of the present disclosure is illustrated. The apparatus 101 may comprise one or more heads 105 engaged with or formed with a base 173, and a motor or programmable motor 161. The base 173 may be directly engaged with a drive shaft 158 of the motor or programmable motor 161. This is known as direct drive. The base 173 and the drive shaft 158 may together be known as the transfer device 171. The base 173 is directly driven by the drive shaft 158 of the programmable motor 161. Stated another way, when the drive shaft 158 is rotated, the base 173 is rotated about an axis of rotation 107. The heads 105, owing their engagement with the base 173, are then are orbited about the axis of rotation 107. In some instances, another apparatus, similar to the apparatus 101 may be provided opposite to apparatus 101, such that they can work on unison. In such an instance, the rotation axes of each apparatus may be positioned coaxially with the heads extending between the motors of the apparatuses.

Figure 25:
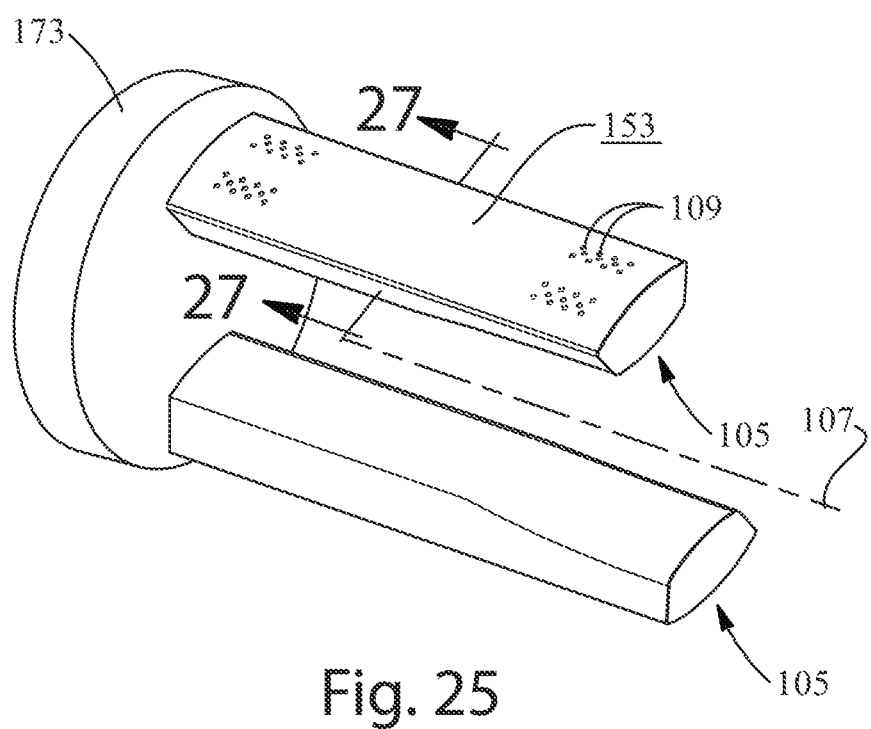
FIG. 25 is a perspective view of a portion of the apparatus comprising the two heads of FIG. 23 in accordance with the present disclosure.

FIG. 25 illustrates a portion of the apparatus 101 comprising a base 173 and two heads 105 extending from the base. The rotation axis of the heads 105 is indicated as 107. The heads 105 may each have fluid ports 109 defined therein, such that one or more fluid pressures may be provided at the surface 153 of the heads 105.

Figure 26:
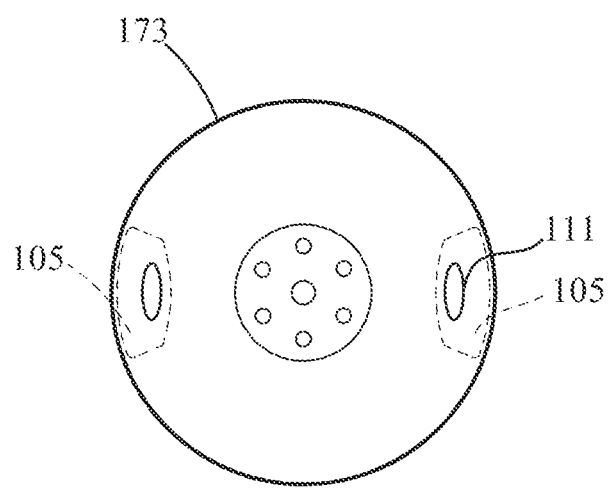
FIG. 26 is a rear view of the portion of the apparatus comprising the two heads of FIG. 25 in accordance with the present disclosure.
Figure 27:
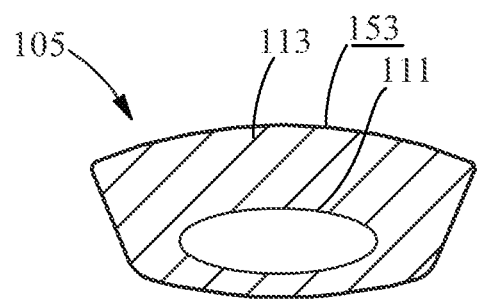
FIG. 27 is a cross-sectional view of the portion of the apparatus comprising the two heads taken about line 27-27 of FIG. 25 in accordance with the present disclosure.

Referring to FIGS. 26 and 27, the heads 105 may each define one or more fluid cavities 111 therein. The surface 153 may define one or more fluid ports 109 therein. The one or more fluid ports 109 may be in at least partial fluid communication with the one or more fluid cavities 111 so that fluid pressure (positive and/or negative) may be applied to discrete articles 102 positioned on the surface 153 of the heads 105 in locations where the discrete articles 102 overlap the one or more fluid ports 109. The one or more fluid cavities 111 may be in fluid communication with one or more fluid pumps (see e.g., fluid pump 115 in FIG. 21) configured to provide a positive and/or negative fluid pressure to the fluid cavities 111. In a form, one fluid pump may be configured to provide a positive fluid pressure and another fluid pump may be configured to provide a negative fluid pressure. One or more of the fluid pumps may be in fluid communication with a manifold on the apparatus which is in fluid communication with at least some of the fluid cavities 111. In such an instance, positive and/or negative fluid pressure may be provided by the manifold to the at least some fluid cavities 111 as desired and as will be recognized by those of skill in the art.

Referring to FIG. 27, an example cross-sectional view of the head 105 taken about line 27-27 of FIG. 7 is illustrated. A fluid cavity 111 is formed within the head 105 and is in fluid communication with the fluid ports 109 (see FIG. 25). An optional support material 113 may be positioned within the head 105 and at least partially surround the fluid cavity 111. The support material 113 may comprise a low density material, a low density foam, a plastic material, a non-foam material, or a foam material, for example. The support material may have channels in it so that the fluid cavity 111 may be in fluid communication with the fluid ports 109. The support material, in some instances, may also merely be portions of the head and made of the same materials as the head.

Each programmable motor may be in electrical communication with a motor control system. The motor control system may comprise an amplifier and/or a controller. Example motor control systems 270 are illustrated in FIGS. 21-24. The motor control system 270 may regulate, control, and/or vary the speed at which the programmable motor runs throughout an orbit, or partial orbit, of the head 105 causing the head 105 to increase or decrease in speed based on where it is in its rotation.

Figure 28A:
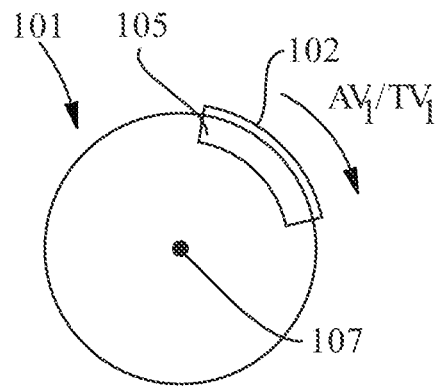
FIG. 28A is a schematic illustration of an example apparatus comprising a head, wherein the head is being rotated about a rotation axis at a first angular velocity, AV1, and at a first tangential velocity, TV1 in accordance with the present disclosure.
Figure 28B:
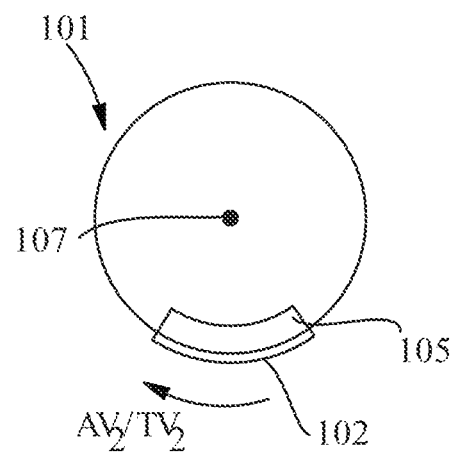
FIG. 28B is a schematic illustration of the example apparatus comprising the head of FIG. 28A, wherein the head is being rotated about the rotation axis at a second angular velocity, AV2, and at a second tangential velocity, TV2, in accordance with the present disclosure.
Figure 28C:
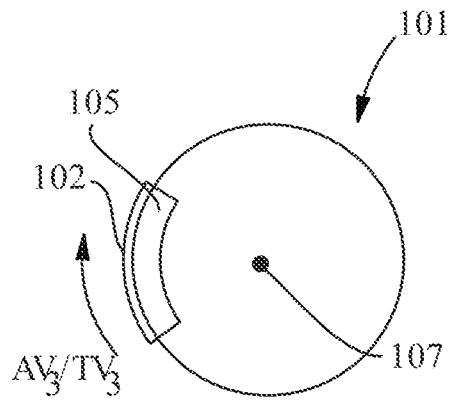
FIG. 28C is a schematic illustration of the example apparatus comprising the head of FIG. 28A, wherein the head is being rotated at a third angular velocity, AV3, and at a third tangential velocity, TV3, in accordance with the present disclosure.

A portion of the apparatus 101 (or 101') comprising the head 105 (or 105) is illustrated in FIGS. 28A-28C. The head 105 of the apparatus 101 is shown in different positions of rotation about the rotation axis 107 and engaged with a discrete article 102. During one revolution of the head 105 about the rotation axis 107, the head 105 may have a first angular velocity, AV1 (FIG. 28A), a second angular velocity, AV2 (FIG. 28B), and a third angular velocity, AV3 (FIG. 28C). The first, second, and third angular velocities may all be different. Alternatively, at least one of the first, second, and third angular velocities may be different than the other two. In other instances, the head 105 may have more than three different angular velocities within one revolution about the rotation axis 107. By rotating the head 105 at a plurality of angular velocities within one revolution about the rotation axis 107, the head 105 may be able to pick up the discrete article 102 while moving at the first angular velocity, AV1, accelerate or decelerate to the second angular velocity, AV2, and then drop off the discrete article 102 at the third angular velocity, AV3. The first and third angular velocities may be same or different. In an instance, the first and third angular velocities may be constant, or substantially constant, throughout a pick-up zone or a drop-off zone, while the second angular velocity, AV2, may be variable. The second angular velocity, AV2, may be used when the head 105 is outside of a pick-up zone or a drop-off zone for the discrete article 102.

Again referring to FIGS. 28A-28C, a surface of the head 105 (or 105) may have a plurality of tangential velocities within one revolution of the head 105 about the rotation axis 107. The tangential velocities may be TV1 (FIG. 28A), TV2 (FIG. 28B), and TV3 (FIG. 28C). All of the tangential velocities may be the same or different. In an instance, at least one of the tangential velocities may be different than the other two tangential velocities. By rotating the surface of the head 105 at a plurality of tangential velocities within one revolution about the rotation axis 107, the surface of the head 105 may be able to pick up the discrete article 102 while moving at the first tangential velocity, TV1, accelerate or decelerate to the second tangential velocity, TV2, and then drop off the discrete article 102 at the third angular velocity, TV3. The first and third tangential velocities may be same or different. In an instance, the first and third tangential velocities may be constant or substantially constant throughout a pick-up zone or a drop-off zone, while the second tangential velocity may be variable. The second tangential velocity, TV2, may be used when the head 105 is outside of a pick-up zone or a drop-off zone for the discrete article 102.

Figure 29A:
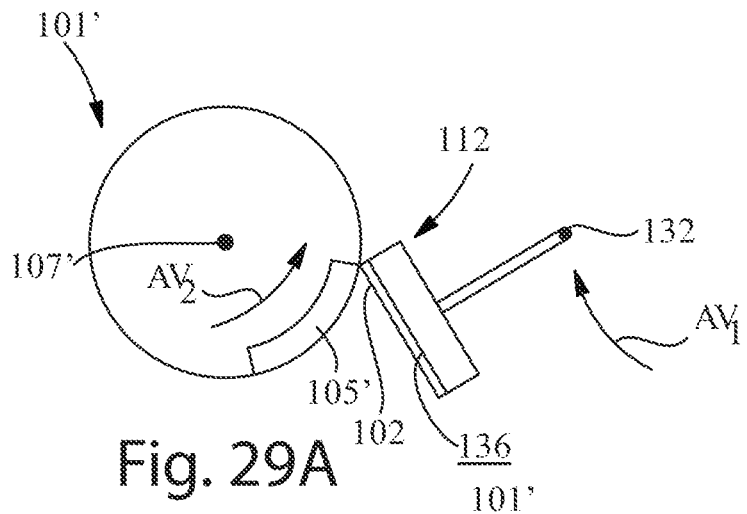
FIGS. 29A-29C are illustrative examples of a discrete article being transferred from a transfer surface of a transfer member of a transfer apparatus to a surface of a head of an apparatus, with the angular velocity, AV1, of the transfer surface being constant, or substantially constant, and with the angular velocity, AV2, of the surface being the same as or substantially the same as the angular velocity, AV1 of the transfer surface at the point of discrete article transfer and/or within the zone of discrete article transfer in accordance with the present disclosure.
Figure 29B:
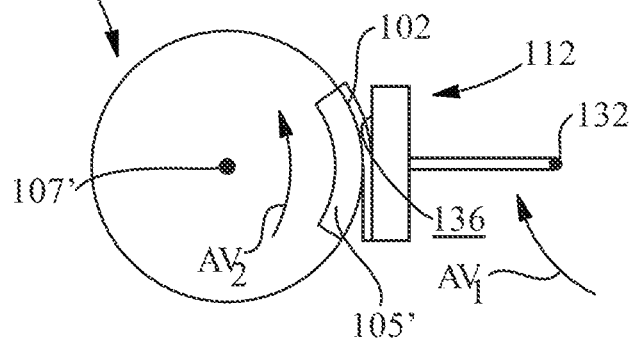
Figure 29C:
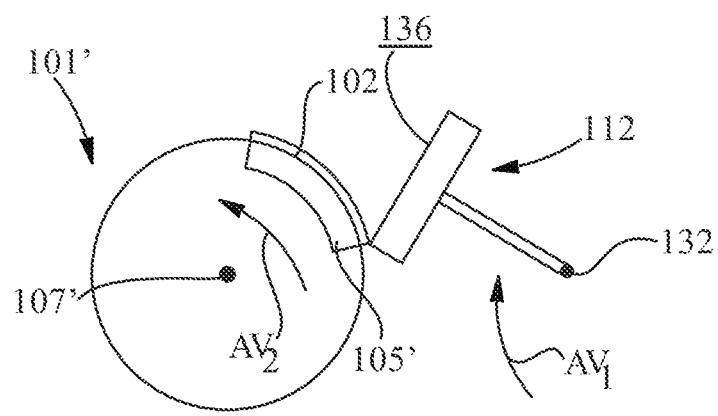

FIGS. 29A-29C schematically illustrate the transfer of a discrete article 102 progressing through a drop-off zone between a transfer member 112 of the transfer assembly 100 and a head 105' of the apparatus 101', as an example, although a similar concept would apply at a discrete article pick-up zone when the head 101 is transferring the discrete article 102 to the transfer member 112. The transfer member 112 is rotating about the rotation axis 132 of the transfer assembly 100 and the head 105' is rotating about the rotation axis 107'. In FIGS. 29A-29C, the transfer member 112 may have a constant, or substantially constant, angular velocity, AV1, at the point or zone of discrete article transfer. The head 105' may have an angular velocity, AV2, that may be constant, or substantially constant, at the point or zone of discrete article transfer. The angular velocity, AV1, may be equal to, or substantially equal to, the angular velocity, AV2 at the point or zone of discrete article transfer. In other instances, the angular velocity, AV1, may be less than, greater than, or different than the angular velocity, AV2, at the point or zone of discrete article transfer. FIG. 29A illustrates the beginning of an example discrete article transfer. FIG. 29B illustrates a middle portion of the example discrete article transfer. FIG. 29C illustrates the end of the example discrete article transfer. It is to be noted that the constant, or substantially constant, minimum gap or distance may be provided intermediate the surface 136 of the transfer member 112 and a surface of the head 105' to ensure smooth and reliable transfer without fold-over of portions of the discrete article 102. The constant, or substantially constant, minimum gap or distance is described in further detail above.

Figure 30A:
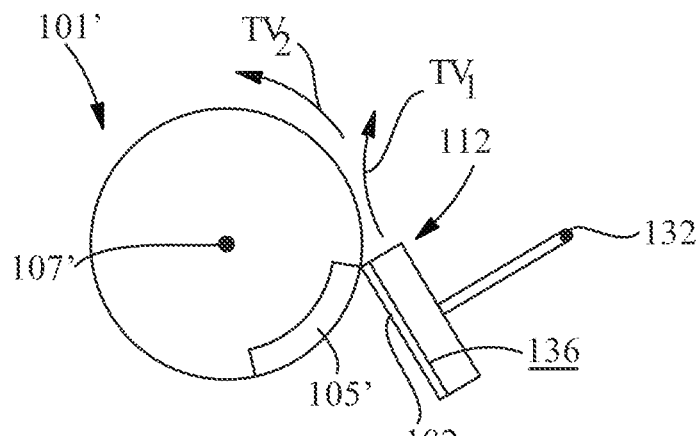
FIGS. 30A-30C are illustrative examples of a discrete article being transferred from a transfer surface of a transfer member of a transfer apparatus to a surface of a head of an apparatus, with the tangential velocity, TV1, of the transfer surface being constant, or substantially constant, and with the tangential velocity, TV2, of the surface being the same as or substantially the same as the tangential velocity, TV1, of the transfer surface at the point of discrete article transfer and/or within the zone of discrete article transfer in accordance with the present disclosure.
Figure 30B:
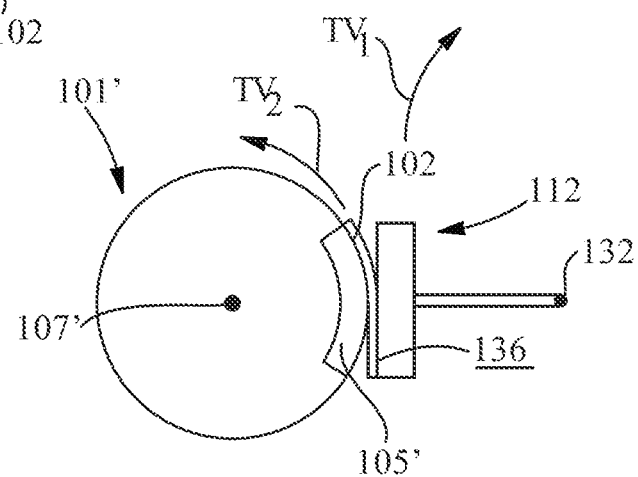
Figure 30C:
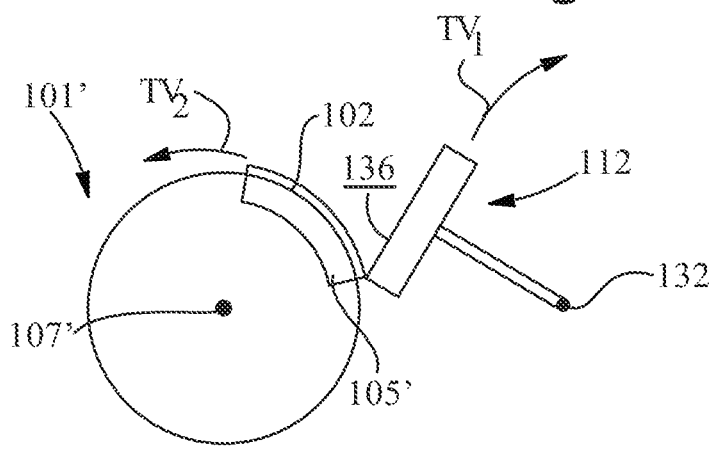

FIGS. 30A-30C schematically illustrate the transfer of a discrete article 102 progressing through a drop-off zone between the transfer member 112 of the transfer assembly 100 and a head 105' of the apparatus 101', as an example, although a similar concept would apply at a discrete article pick-up zone when the head 105 transfers the discrete article 102 to the transfer member 112. The transfer member 112 is rotating about the rotation axis 132 of the transfer assembly 100 and the head 105' is rotating about the rotation axis 107'. In FIGS. 30A-30C, the transfer surface 136 of the transfer member 112 may have a constant, or substantially constant, tangential velocity, TV1, at the point or zone of discrete article transfer. The head 105' may have a tangential velocity, TV2, that may be constant, or substantially constant, at the point or zone of discrete article transfer. The tangential velocity, TV1, may be equal to, or substantially equal to, the tangential velocity, TV2, at the point or zone of discrete article transfer. In other instances, the tangential velocity, TV1, may be less than, greater than, or different than the tangential velocity, TV2, at the point or zone of discrete article transfer. FIG. 30A illustrates the beginning of an example discrete article transfer. FIG. 30B illustrates a middle portion of the example discrete article transfer. FIG. 30C illustrates the end of the example discrete article transfer. It is to be noted that the constant, or substantially constant, minimum gap or distance may be provided intermediate the surface 136 of the transfer member 112 and a surface of the head 105' to ensure smooth and reliable transfer without fold-over of portions of the discrete article 102. The constant, or substantially constant, minimum gap or distance is described in greater detail above.

Figure 31A:
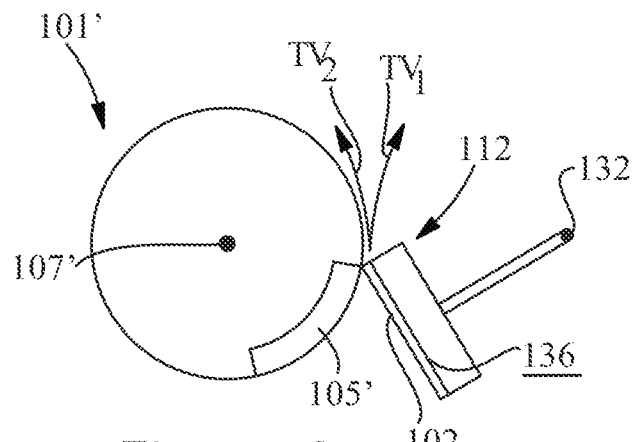
FIGS. 31A-31C are illustrative examples of a discrete article being transferred from a transfer surface of a transfer member of a transfer apparatus to a surface of a head of an apparatus, with the tangential velocity, TV1, of the transfer surface being constant, or substantially constant, and with the tangential velocity, TV2, of the surface being constant, or substantially constant, wherein the constant, or substantially constant, tangential velocity, TV2, of the head is greater than the constant, or substantially constant, tangential velocity, TV1, of the transfer surface at the point of discrete article transfer and/or within the zone of discrete article transfer in accordance with the present disclosure.
Figure 31B:
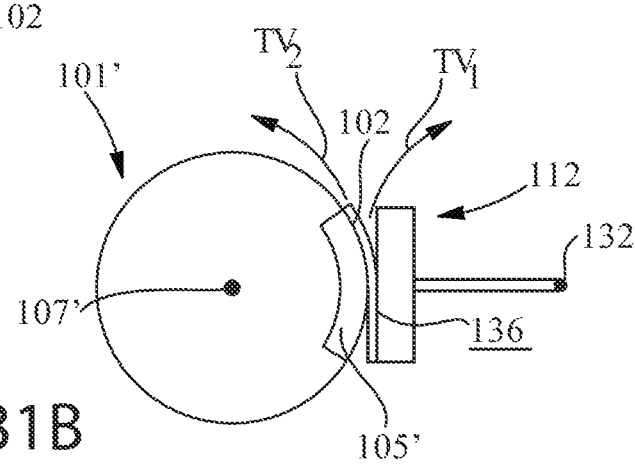
Figure 31C:
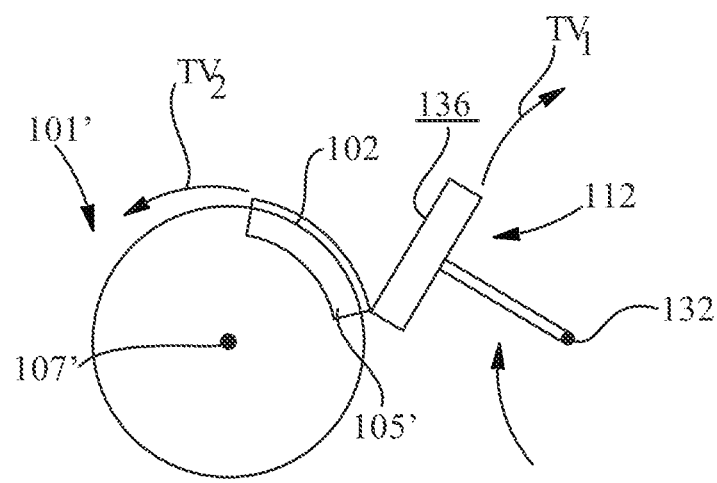

FIGS. 31A-31C schematically illustrate the transfer of a discrete article 102 progressing through a drop-off zone between the transfer member 112 of the transfer assembly 100 and a head 105' of the apparatus 101', as an example, although a similar concept would apply at a discrete article pick-up zone when the head 105 transfers the discrete article 102 to the transfer member 112. The transfer member 112 is rotating about the rotation axis 132 of the transfer assembly 100 and the head 105' is rotating about the rotation axis 107'. In FIGS. 31A-31C, the transfer surface 136 of the transfer member 112 may have a constant, or substantially constant, tangential velocity, TV1, at the point or zone of discrete article transfer. The surface of the head 105' may have a tangential velocity, TV2, that may be constant, or substantially constant, at the point or zone of discrete article transfer. Alternatively, the tangential velocity, TV2, of the surface of the head 105' may be variable at the point or zone of discrete article transfer. The tangential velocity, TV1, may be less than, the tangential velocity, TV2, at the point or zone of discrete article transfer to tension the discrete article being transferred. The tangential velocity, TV2, of the surface of the head 105' may be at least about 2% to about 35%, at least about 2% to about 30%, at least about 5% to about 25%, at least about 3% to about 25%, at least about 3%, at least about 5%, at least about 10%, or at least about 15%, specifically reciting all 0.1% increments within the specified ranges and all ranges formed therein or thereby, greater than the tangential velocity, TV1, of the transfer surface 136 at the point or zone of discrete article transfer to tension the discrete article 102 being transferred. Tensioning of the discrete articles being transferred may allow for multiple product sizes to be run using the same transfer assembly 100. The tensioning essentially may create a situation of controlled slippage of the discrete articles from one component to another component where a shorter discrete article can be transferred to a larger head. Further, the tensioning may at least partially remove wrinkles in the discrete articles being transferred. Also, the tensioning may at least partially improve control of the discrete articles during transfer, as the tensioning may at least partially limit the discrete articles from being disturbed by moving air or other factors that negatively impact the transfer.

FIG. 31A illustrates the beginning of an example discrete article transfer, including tensioning of the discrete article 102. FIG. 31B illustrates a middle portion of the example discrete article transfer, including tensioning of the discrete article 102. FIG. 31C illustrates the end of the example discrete article transfer, including tensioning of the discrete article 102. It is to be noted that the constant, or substantially constant, minimum gap or distance may be provided intermediate the surface 136 of the transfer member 112 and a surface of the head 105' to ensure smooth and reliable transfer without fold-over of portions of the discrete article 102. The constant, or substantially constant, minimum gap or distance is described in greater detail above.

Figure 32A:
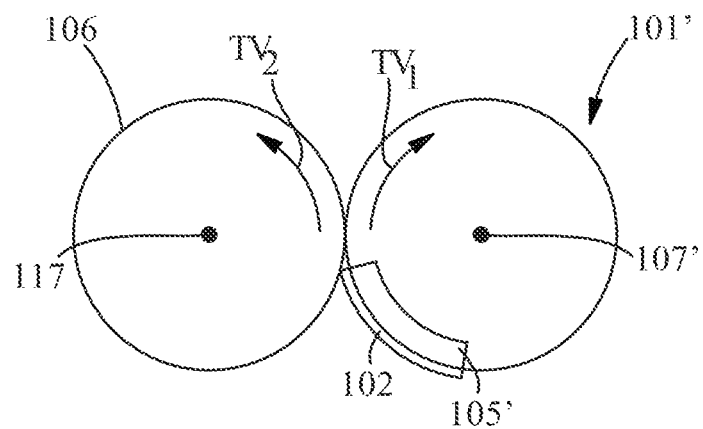
FIGS. 32A-32C are illustrative examples of a discrete article being transferred from a surface of a head of an apparatus to a moving or rotating carrier member in accordance with the present disclosure.
Figure 32B:
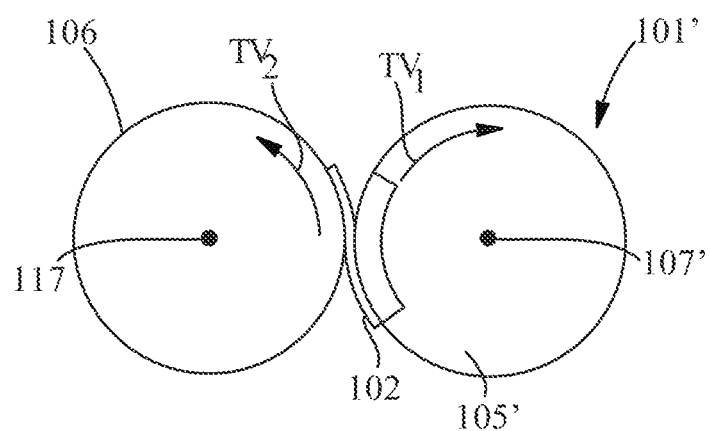
Figure 32C:
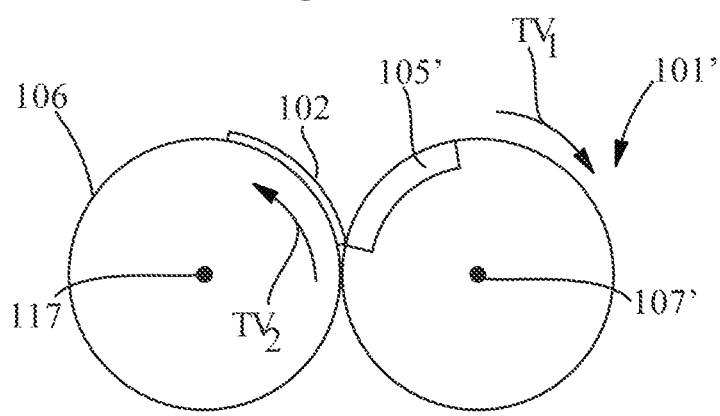

FIGS. 32A-32C schematically illustrate transfer of a discrete article 102 from the head 105' of the apparatus 101' to the second moving carrier member 106 (or to webs moving over the second moving carrier member). The head 105' rotates about the rotation axis 107' of the apparatus 101', while the second moving carrier member 106 rotates about rotation axis 117. A surface of the head 105' has a first tangential velocity, TV1, at the point or zone of discrete article transfer. The first tangential velocity, TV1, may be constant, or substantially constant at the point or zone of discrete article transfer. A surface of the moving carrier member 106 may have a second tangential velocity, TV2, at the point or zone of discrete article transfer. The second tangential velocity, TV2, may be equal to, substantially equal to, greater than, or less than, the first tangential velocity, TV1, at the point or zone of discrete article transfer. If the second tangential velocity, TV2, is greater than the first tangential velocity, TV1, at the point or zone of discrete article transfer, the discrete article 102 may be tensioned during the transfer. The second tangential velocity, TV2, may be at least about 2% to about 35%, at least about 2% to about 30%, at least about 5% to about 25%, at least about 3% to about 25%, at least about 3%, at least about 5%, at least about 10%, or at least about 15%, specifically reciting all 0.1% increments within the specified ranges and all ranges formed therein or thereby, greater than the first tangential velocity, TV1, at the point or zone of discrete article transfer to tension the discrete article 102 being transferred. On the input side of the transfer assembly 100, a surface of the first moving carrier member 104 may have a tangential velocity that is slower than the tangential velocity of a surface of the head 105 to tension the discrete article at the point or zone of discrete article transfer.

Figure 33A:
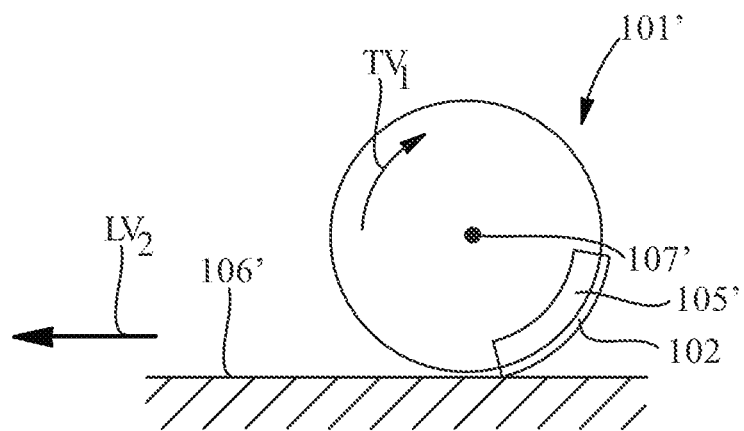
FIGS. 33A-33C are illustrative examples of a discrete article being transferred from a surface of a head of an apparatus to a generally linear conveyor in accordance with the present disclosure.
Figure 33B:
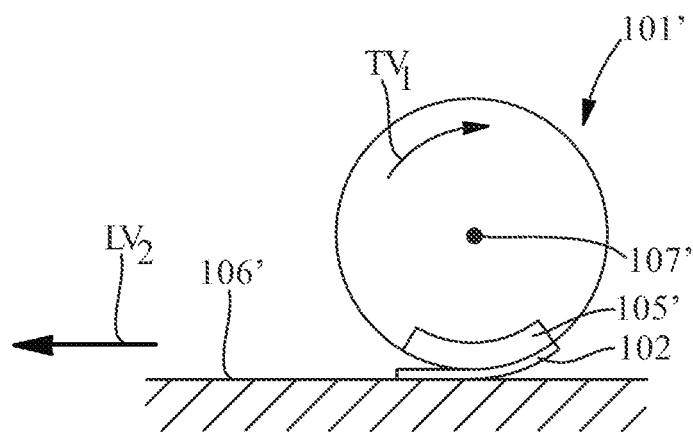
Figure 33C:
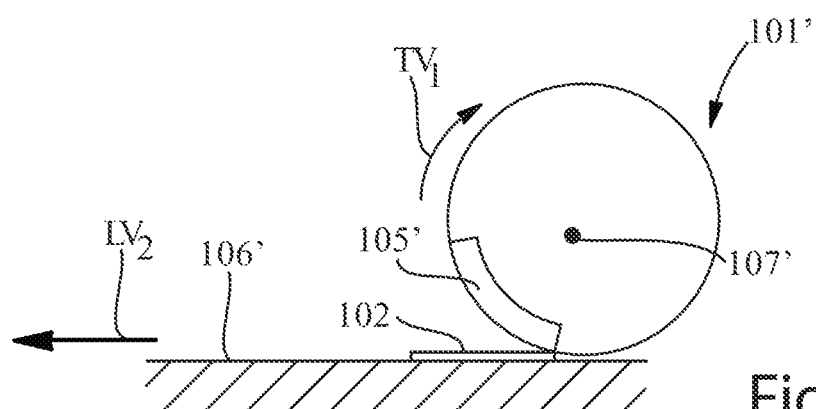

FIGS. 33A-33C schematically illustrate transfer of a discrete article 102 from the head 105' of the apparatus 101' to a linear conveyor 106'. The head 105' rotates about the rotation axis 107' of the apparatus 101'. A surface of the head 105' has a first tangential velocity, TV1 at the point or zone of discrete article transfer. The first tangential velocity, TV1, may be constant, or substantially constant at the point or zone of discrete article transfer. A surface of the linear conveyor 106' may have a linear velocity, LV2. The linear velocity, LV2, may be equal to, substantially equal to, greater than, or less than the first tangential velocity, TV1, at the point or zone of discrete article transfer. The linear velocity, LV2, may be at least about 2% to about 35%, at least about 2% to about 30%, at least about 5% to about 25%, at least about 3% to about 25%, at least about 3%, at least about 5%, at least about 10%, or at least about 15%, specifically reciting all 0.1% increments within the specified ranges and all ranges formed therein or thereby, greater than the first tangential velocity, TV1, at the point or zone of discrete article transfer to tension the discrete article 102 being transferred. On the input side of the transfer assembly 100, a surface of a linear conveyor may have a tangential velocity that is slower than the tangential velocity of a surface of the head 105 to tension the discrete article at the point or zone of discrete article transfer.

In a form, a method of transferring discrete articles between a transfer assembly comprising one or more transfer members and an apparatus comprising one or more heads is provided. The discrete articles may be transferred from a transfer surface of the transfer member to a surface of the head of the apparatus (output side of transfer assembly) and/or may be transferred from the surface of the head of the apparatus to the transfer surface of the transfer member (input side of transfer assembly). The transfer assembly may comprise a frame defining a first rotation axis and at least one transfer member each comprising a transfer surface configured to receive one or more of the discrete articles. The method may comprise rotating the transfer member of the transfer assembly about the first rotation axis at a substantially constant angular velocity, maintaining the transfer surface at a substantially constant minimum distance away from a surface of the head at a point or zone of discrete article transfer, and rotating the head of the apparatus about a second rotation axis at a plurality of angular velocities. A first angular velocity of the head may be constant, or substantially constant, at the point or zone of discrete article transfer. Alternatively, the first angular velocity of the head may be variable at the point or zone of discrete article transfer.

A tangential velocity of the transfer surface of the transfer member may be constant, or substantially constant, at the point or zone of discrete article transfer. A tangential velocity of the surface of the head of the apparatus may be the same as, or substantially the same as (e.g., +/–2%), the constant, or substantially constant, tangential velocity of the transfer surface at the point or zone of discrete article transfer. In some instances, the tangential velocity of the surface of the head of the apparatus may also be variable at the point or zone of discrete article transfer and/or may be different than the constant, or substantially constant, tangential velocity of the transfer surface at the point or zone of discrete article transfer.

The method may comprise rotating the head of the apparatus about the second rotation axis (e.g., rotation axis 107) at a second angular velocity when the head is outside of a zone of discrete article transfer. The second rotation axis may be parallel to, substantially parallel to, or transverse to, the first rotation axis of the transfer assembly. The second angular velocity of the head may be different than or the same as the first angular velocity of the head.

In an instance, the discrete articles may be transferred from the transfer surface of the transfer member to the surface of the head on an output side of the transfer assembly. The method may comprise rotating the head about the second rotation axis at a third, different angular velocity when the surface of the head is transferring the discrete articles to a discrete article conveying device, such as the second moving carrier member 106 or the linear conveyor 106'. A tangential velocity of the surface of the head may match, or substantially match, a tangential velocity or linear speed of the discrete article conveying device at a second point of discrete article transfer. The method may comprise rotating the head about the second rotation axis between the first, second, and third angular velocities in one revolution of the head.

The surface of the head may comprise an arcuate portion or may be fully arcuate. The transfer surface may be flat, substantially flat, or may comprise one or more flat portions. The transfer surface may also be arcuate or comprise one or more arcuate portions in some instances. The method may comprise moving the flat or substantially flat transfer surface radially inwardly and radially outwardly relative to the first rotation axis of the transfer assembly at the point of discrete article transfer to maintain the substantially constant minimum distance or gap between the surface of the head and the transfer surface. The transfer surface of the transfer member may also be rotated about a third rotation axis (e.g., rotation axis 164) between a first position and a second position. The first rotation axis (e.g., rotation axis 132) of the transfer assembly may extend in a first direction and the third rotation axis of the transfer assembly may extend in a second, different direction. The first rotation axis of the transfer assembly may be parallel to, or substantially parallel to (e.g., +/–5 degrees), the second rotation axis (e.g., rotation axis 107) of the apparatus, and the third rotation axis of the transfer assembly may be perpendicular to, or substantially perpendicular to (e.g., +/–5 degrees), the first and second rotation axes.

The transfer surface of the transfer assembly may be rotated between about 80 degrees and about 100 degrees, about 90 degrees, or 90 degrees, about the third rotation axis of the transfer assembly between the first position and the second position. Other degrees of rotation between the first position and the second position are also specified herein, but not again set forth here for brevity.

The method may further comprise using a radial displacement mechanism operably engaged with a portion of the transfer member to maintain the transfer surface at the substantially constant minimum distance away from the surface of the head of the apparatus at the point or zone of discrete article transfer. The method may also comprise maintaining a substantially constant pressure between the transfer surface and the surface of the head of the apparatus at the point or zone of discrete article transfer.

In a form, a method of transferring discrete articles between a transfer assembly and an apparatus comprising one or more heads is provided. The transfer assembly may comprise a frame defining a first rotation axis and at least one transfer member each comprising a transfer surface configured to receive one or more of the discrete articles. The method may comprise rotating the transfer member of the transfer assembly about the first rotation axis at a constant, or substantially constant, angular velocity and maintaining the transfer surface at a constant, or substantially constant, minimum distance away from a surface of the head at a point or zone of discrete article transfer. A tangential velocity of the transfer surface may be constant or substantially constant at the point or zone of discrete article transfer. The method may further comprise rotating the head of the apparatus about a second rotation axis at a variable angular velocity. A first angular velocity of the head may be constant, substantially constant, or variable, at the point or zone of discrete article transfer. A tangential velocity of the surface of the head may be the same as, or substantially the same as (e.g., +/–2%), the constant, or substantially constant, tangential velocity of the transfer surface at the point or zone of discrete article transfer. The tangential velocity of the surface of the head, in other instances, may be different than the constant, or substantially constant, tangential velocity of the transfer surface at the point or zone of discrete article transfer.

The transfer surface may be flat, substantially flat, or may comprise a flat portion. In other instances, the transfer surface may be arcuate or comprise one or more arcuate portions. The surface of the head may comprise one or more arcuate portions or may be arcuate. The surface of the head may be configured to receive one of the discrete articles. The first rotation axis of the transfer assembly may be parallel to, or substantially parallel to, the second rotation axis of the apparatus. The method may comprise rotating the transfer member about a third rotation axis of the transfer assembly between a first position and a second position. The transfer member may be rotated between about 80 degrees and about 100 degrees, about 90 degrees, or 90 degrees, about the third rotation axis between the first position and the second position. Other degrees of rotation between the first and second positions are specified herein, but are not again set forth for brevity. The first rotation axis of the transfer assembly and the second rotation axis of the apparatus may be perpendicular to, or substantially perpendicular to, the third rotation axis of the transfer assembly.

In a form, a method may comprise transferring discrete articles between a transfer assembly and an apparatus comprising at least one head. The transfer assembly may comprise a frame defining a first rotation axis and at least one transfer member each comprising a transfer surface configured to receive one or more of the discrete articles. The transfer surface may be flat, substantially flat, or may comprise one or more flat or substantially flat portions. In other instances, the transfer surface may be arcuate or may comprise one or more an arcuate portions. The method may comprise rotating the transfer member of the transfer assembly about the first rotation axis at a constant, or substantially constant, angular velocity, maintaining the transfer surface at a constant, or substantially constant, minimum distance away from a surface of the head at a point or zone of discrete article transfer, and rotating the head of the apparatus about a second rotation axis at a variable angular velocity. A first angular velocity of the head may be constant, substantially constant, or variable at the point or zone of discrete article transfer. The surface of the head may be arcuate or may comprise an arcuate portion. The first rotation axis of the transfer assembly may be parallel to, or substantially parallel to, the second rotation axis of the apparatus. The method may comprise rotating the transfer member about a third rotation axis of the transfer assembly between a first position and a second position. The first rotation of the transfer assembly axis may extend in a first direction. The third rotation axis of the transfer assembly may extend in a second, different direction. The transfer member may be rotated about the third rotation axis between about 80 degrees and about 100, about 90 degrees, or 90 degrees, between the first position and the second position. Other degrees increments between the first and second positions are specified herein, but not set forth again for brevity.

A first tangential velocity of the transfer surface of the transfer member may be constant, or substantially constant, at the point or zone of discrete article transfer. A second tangentially velocity of the surface of the head may be constant, substantially constant, or variable at the point or zone of discrete article transfer. The first and second tangentially velocities may be the same, substantially the same, or different at the point or zone of discrete article transfer.

In a form a method of transferring discrete articles from a transfer assembly to an apparatus comprising one or more heads is provided. The transfer assembly may comprise a frame defining a first rotation axis and at least one transfer member each comprising a transfer surface configured to receive one of the discrete articles. The method may comprise rotating the transfer member of the transfer assembly about the first rotation axis, maintaining the transfer surface at a substantially constant minimum distance away from a surface of the head at a point or zone of discrete article transfer. The transfer surface of the transfer member may be moved at a first constant, or substantially constant, tangential velocity at the point or zone of discrete article transfer. The method may further comprise rotating the head of the apparatus about a second rotation axis. The surface of the head may be moved at a second constant, or substantially constant, tangential velocity at the point or zone of discrete article transfer. The second constant, or substantially constant, tangential velocity of the head may be greater than the first constant, or substantially constant, tangential velocity of the transfer surface at the point or zone of discrete article transfer to tension the discrete articles being transferred. The second constant, or substantially constant, tangential velocity may be at least about 2% to about 35%, at least about 2% to about 30%, at least about 5% to about 25%, at least about 3% to about 25%, at least about 3%, at least about 5%, at least about 10%, or at least about 15%, specifically reciting all 0.1% increments within the specified ranges and all ranges formed therein or thereby, greater than the first tangential velocity at the point or zone of discrete article transfer to tension the discrete article being transferred.

The transfer member may be rotated about the first rotation axis of the transfer assembly at a constant, or substantially constant, angular velocity. The head may be rotated about the second rotation axis of the apparatus at a variable angular velocity. The rotating the head about the second rotation axis step may comprise rotating the head about the second rotation axis between a first angular velocity, a second angular velocity, and at least a third angular velocity, or between a plurality of angular velocities, in one revolution of the head. The first, second, and third angular velocities may all be different. In other instances, at least one of the first, second, and third angular velocities may be different than the other two angular velocities.

The transfer surface of the transfer member may be rotated about a third rotation axis of the transfer assembly between a first position and a second position. The third rotation axis may not be parallel to the first rotation axis of the transfer assembly and, instead, may be perpendicular, or substantially perpendicular, to the first rotation axis. The transfer surface may be rotated between about 80 degrees and about 100 degrees, about 90 degrees, or 90 degrees, between the first position and the second position. Other degree increments between the first position and second position are described herein, but not set forth again for brevity.

The transfer surface may be flat, substantially flat, or may comprise one or more flat portions. The transfer surface may also be arcuate, in other instances. The surface of the head may be arcuate or may comprise one or more arcuate portions. The method may comprise moving the flat or substantially flat transfer surface radially inwardly and radially outwardly relative to the first rotation axis of the transfer assembly at the point or zone of discrete article transfer to maintain the substantially constant minimum distance. The method may comprise using a radial displacement mechanism operably engaged with a portion of the transfer member to maintain the transfer surface at the constant, or substantially constant, minimum distance away from the surface of the head of the apparatus at the point or zone of discrete article transfer. The method may also comprise maintaining a constant, or substantially constant, pressure between the transfer surface of the transfer member and the surface of the head of the apparatus at the point or zone of discrete article transfer.

In a form, a method of transferring discrete articles from a transfer assembly to an apparatus comprising one or more heads is provided. The transfer assembly may comprise a frame defining a first rotation axis and at least one transfer member each comprising a transfer surface configured to receive one or more of the discrete articles. The method may comprise rotating the transfer member of the transfer assembly about the first rotation axis of the transfer assembly at a constant, or substantially constant, angular velocity and maintaining the transfer surface at a constant, or substantially constant, minimum distance away from a surface of the head at a point or zone of discrete article transfer. The transfer surface may be moved at a first constant, or substantially constant, tangential velocity at the point or zone of discrete article transfer. The method may comprise rotating the head of the apparatus about a second rotation axis at a variable angular velocity or at a plurality of angular velocities. The surface of the head may be moved at a second constant, or substantially constant, tangential velocity at the point or zone of discrete article transfer. The second constant, or substantially constant, tangential velocity of the head may be greater than the first constant, or substantially constant, tangential velocity of the transfer surface at the point or zone of discrete article transfer to tension the discrete article being transferred. The second constant, or substantially constant, tangential velocity may be at least about 2% to about 35%, at least about 2% to about 30%, at least about 5% to about 25%, at least about 3% to about 25%, at least about 3%, at least about 5%, at least about 10%, or at least about 15%, specifically reciting all 0.1% increments within the specified ranges and all ranges formed therein or thereby, greater than the first constant, or substantially constant, tangential velocity at the point or zone of discrete article transfer to tension the discrete article being transferred.

The rotating of the head of the apparatus step may comprise rotating the head about the rotation axis of the apparatus between a first angular velocity, a second angular velocity, and a third angular velocity, or between a plurality of angular velocities, in one revolution of the head. The first, second, and third angular velocities may all be different. In other instances, at least one of the first, second, and third angular velocities may be different than the other two.

The transfer surface may be flat, substantially flat, or may comprise one or more flat portions. In other instances, the transfer surface may be arcuate or comprise one or more arcuate portions. The surface of the head may be arcuate or may comprise one or more arcuate portions.

The method may further comprise moving the flat or substantially flat transfer surface radially inwardly and radially outwardly relative to the first rotation axis of the transfer assembly at the point or zone of discrete article transfer to maintain the constant, or substantially constant, minimum distance. The method may also comprise using a radial displacement mechanism operably engaged with a portion of the transfer member to maintain the transfer surface at the constant, or substantially constant, minimum distance away from the surface of the head of the apparatus at the point or zone of discrete article transfer. The method may additionally comprise maintaining a constant, or substantially constant, pressure between the transfer surface and the surface of the head of the apparatus at the point or zone of discrete article transfer.

In a form, a method of transferring discrete articles from a transfer assembly to an apparatus comprising one or more heads is provided. The transfer assembly may comprise a frame defining a first rotation axis and one or more transfer members each comprising a transfer surface configured to receive one or more of the discrete articles. The transfer surface may be flat, substantially flat, or may comprise one or more flat portions. The transfer surface may also be arcuate, or comprise arcuate portions, in some instances. The method may comprise rotating the transfer member of the transfer assembly about the first rotation axis and maintaining the transfer surface at a constant, or substantially constant, minimum distance away from a surface of the head at a point or zone of discrete article transfer. The transfer surface may be moved at a first constant, or substantially constant, tangential velocity at the point or zone of discrete article transfer. The method may comprise rotating the head of the apparatus about a second rotation axis. The surface of the head may be moved at a second constant, or substantially constant, tangential velocity at the point or zone of discrete article transfer. The surface of the head, in other instances, may also be moved at a variable tangential velocity at the point or zone of discrete article transfer. The second constant, or substantially constant, tangential velocity of the head may be greater than the first constant, or substantially constant, tangential velocity of the transfer surface at the point or zone of discrete article transfer to tension the discrete articles being transferred.

In all of the methods described herein, the methods may comprise retaining one or more of the discrete articles to the transfer surfaces or to the surfaces of the heads through fluid pressures, static, magnetic, adhesives, and/or adhesive attraction, for example.

The transfer members, apparatuses comprising the heads, wheels, rotation assemblies, and/or any other part or component that rotates about a rotation axis may comprise aluminum, steel, plastic, titanium, carbon fiber composite, and/or other high strength/light weight material. By using high strength/light weight materials, the amount of mass rotating about a rotation axis may be reduced compared to related art transfer assemblies or apparatuses. This reduction in mass may allow the overall transfer apparatuses of the present disclosure to operate at a higher throughput of discrete articles per minute.

The overall transfer apparatuses of the present disclosure may process or transfer over 800 discrete articles per minute, alternatively, over 900 discrete articles per minute, alternatively, over 1,000 discrete articles per minute, alternatively, over 1,100 discrete articles per minute, alternatively, over 1,200 discrete articles per minute, and alternatively, over 1,300 discrete articles per minute. In other instances, the overall transfer apparatuses of the present disclosure may process or transfer between 600 and 1500 discrete articles per minute, specifically including each whole number within the specified range.

Any of the methods and apparatuses described herein may be used in conjunction with the inventive concepts disclosed in European Patent Application No. EP12162251.8, entitled METHOD AND APPARATUS FOR MAKING PERSONAL HYGIENE ABSORBENT ARTICLES, and filed on Mar. 29, 2012.

Any of the transfer surfaces (e.g., 136), carrier members (e.g., 104, 106), and/or the heads (e.g., heads 105, 105') may comprise one or more resilient materials thereon. The resilient materials may comprise one or more foams, rubbers, silicon rubbers, polymers, and/or polyurethane. The resilient materials may cover the entire surfaces of the transfer surfaces, the carrier members, and/or the heads, or may cover less than the entire surfaces of the transfer surfaces, the carrier members, and/or the heads. The resilient members may be provided to achieve better transfer of discrete articles by allowing one component to apply a force to another component during transfer. Stated another way, the resilient members may be provided to allow for interference transfer between at least some of the various components discussed in this paragraph. In some forms, the resilient members may have a Shore A hardness of between about 20 and about 80, specifically reciting all 0.5 Shore A hardness increments within the specified range.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. A method of transferring discrete articles from a transfer assembly to an apparatus comprising a head, wherein the transfer assembly comprises a frame defining a first rotation axis and a transfer member comprising a transfer surface configured to receive one of the discrete articles, the method comprising:
   rotating the transfer member of the transfer assembly about the first rotation axis;
   maintaining the transfer surface at a substantially constant minimum distance away from a surface of the head at a point of discrete article transfer, wherein the transfer surface is moved at a first substantially constant tangential velocity at the point of discrete article transfer; and
   rotating the head of the apparatus about a second rotation axis, wherein the surface of the head is moved at a second substantially constant tangential velocity at the point of discrete article transfer, and wherein the second substantially constant tangential velocity of the head is greater than the first substantially constant tangential velocity of the transfer surface to tension the discrete articles being transferred at the point of discrete article transfer.

2. The method of claim 1, wherein the transfer member is rotated about the first rotation axis at a substantially constant angular velocity, and wherein the head is rotated about the second rotation axis at a variable angular velocity.

3. The method of claim 1, wherein the rotating the head about the second rotation axis step comprises rotating the head about the second rotation axis between a first angular velocity, a second angular velocity, and a third angular velocity in one revolution of the head, wherein the first, second, and third angular velocities are all different.

4. The method of claim 1, wherein the transfer surface is rotated about a third rotation axis that is not parallel to the first rotation axis between a first position and a second position, and wherein the transfer surface is rotated between about 80 degrees and about 100 degrees between the first position and the second position.

5. The method of claim 1, wherein the transfer surface is substantially flat, and wherein the surface of the head comprises an arcuate portion.

6. The method of claim 1, wherein the second substantially constant tangential velocity of the head is at least 3% greater than the first substantially constant tangential velocity of the transfer surface.

7. The method of claim 1, wherein the second substantially constant tangential velocity of the head is between about 3% and about 25% greater than the first substantially constant tangential velocity of the transfer surface.

8. The method of claim 1, wherein the transfer surface is substantially flat, the method comprising moving the substantially flat transfer surface radially inwardly and radially outwardly relative to the first rotation axis at the point of discrete article transfer to maintain the substantially constant minimum distance.

9. The method of claim 1, wherein the transfer surface is substantially flat, the method comprising using a radial displacement mechanism operably engaged with a portion of the transfer member to maintain the transfer surface at the substantially constant minimum distance away from the surface of the head of the apparatus at the point of discrete article transfer.

10. The method of claim 1, comprising maintaining a substantially constant pressure between the transfer surface and the surface of the head of the apparatus at the point of discrete article transfer.

11. A method of transferring discrete articles from a transfer assembly to an apparatus comprising a head, wherein the transfer assembly comprises a frame defining a first rotation axis and a transfer member comprising a transfer surface configured to receive one of the discrete articles, the method comprising:
   rotating the transfer member of the transfer assembly about the first rotation axis at a substantially constant angular velocity;
   maintaining the transfer surface at a substantially constant minimum distance away from a surface of the head at a point of discrete article transfer, wherein the transfer surface is moved at a first substantially constant tangential velocity at the point of discrete article transfer; and
   rotating the head of the apparatus about a second rotation axis at a variable angular velocity, wherein the surface of the head is moved at a second substantially constant tangential velocity at the point of discrete article transfer, and wherein the second substantially constant tangential velocity of the head is greater than the first substantially constant tangential velocity of the transfer surface.

12. The method of claim 11, wherein the second substantially constant tangential velocity of the head is greater than the first substantially constant tangential velocity of the transfer surface to tension the discrete articles being transferred at the point of discrete article transfer.

13. The method of claim 11, wherein the rotating the head of the apparatus step comprises rotating the head about the second rotation axis between a first angular velocity, a second angular velocity, and a third angular velocity in one revolution of the head, wherein the first, second, and third angular velocities are all different.

14. The method of claim 11, wherein the transfer surface is substantially flat, and wherein the surface of the head comprises an arcuate portion.

15. The method of claim 11, wherein the second substantially constant tangential velocity of the head is at least 3% greater than the first substantially constant tangential velocity of the transfer surface.

16. The method of claim 11, wherein the second substantially constant tangential velocity of the head is between about 2% and about 25% greater than the first substantially constant tangential velocity of the transfer surface.

17. The method of claim 11, wherein the transfer surface is substantially flat, the method comprising moving the substantially flat transfer surface radially inwardly and radially outwardly relative to the first rotation axis at the point of discrete article transfer to maintain the substantially constant minimum distance.

18. The method of claim 11, wherein the transfer surface is substantially flat, the method comprising using a radial displacement mechanism operably engaged with a portion of the transfer member to maintain the transfer surface at the substantially constant minimum distance away from the surface of the head of the apparatus at the point of discrete article transfer.

19. The method of claim 11, comprising maintaining a substantially constant pressure between the transfer surface and the surface of the head of the apparatus at the point of discrete article transfer.

20. A method of transferring discrete articles from a transfer assembly to an apparatus comprising a head, wherein the transfer assembly comprises a frame defining a first rotation axis and a transfer member comprising a transfer surface configured to receive one of the discrete articles, wherein the transfer surface is substantially flat, the method comprising:

rotating the transfer member of the transfer assembly about the first rotation axis;

maintaining the transfer surface at a substantially constant minimum distance away from a surface of the head at a point of discrete article transfer, wherein the transfer surface is moved at a first substantially constant tangential velocity at the point of discrete article transfer; and rotating the head of the apparatus about a second rotation axis, wherein the surface of the head is moved at a second substantially constant tangential velocity at the point of discrete article transfer, and wherein the second substantially constant tangential velocity of the head is greater than the first substantially constant tangential velocity of the transfer surface to tension the discrete articles being transferred at the point of discrete article transfer.

21. The method of claim 20, wherein the transfer surface or the surface of the head comprises a resilient material.

* * * * *